(12) United States Patent
Siddiqi et al.

(10) Patent No.: US 7,994,304 B2
(45) Date of Patent: *Aug. 9, 2011

(54) METHODS AND COMPOSITIONS FOR SEQUENCING A NUCLEIC ACID

(75) Inventors: Suhaib Siddiqi, Burlington, MA (US); Hernan Orgueira, Cambridge, MA (US); Edyta Olejnik, Brookline, MA (US); Subramanian Marappan, Brookline, MA (US); Philip R. Buzby, Brockton, MA (US); Atanu Roy, Woburn, MA (US)

(73) Assignee: Helicos Biosciences Corporation, Cambridge, MA (US)

( * ) Notice: Subject to any disclaimer, the term of this patent is extended or adjusted under 35 U.S.C. 154(b) by 425 days.

This patent is subject to a terminal disclaimer.

(21) Appl. No.: 11/929,084

(22) Filed: Oct. 30, 2007

(65) Prior Publication Data

US 2008/0227970 A1    Sep. 18, 2008

Related U.S. Application Data

(63) Continuation of application No. 11/803,339, filed on May 14, 2007, which is a continuation-in-part of application No. 11/603,945, filed on Nov. 22, 2006, which is a continuation-in-part of application No. 11/496,275, filed on Jul. 31, 2006, now abandoned, which is a continuation-in-part of application No. 11/496,274, filed on Jul. 31, 2006, now abandoned, which is a continuation-in-part of application No. 11/496,262, filed on Jul. 31, 2006, now abandoned, which is a continuation-in-part of application No. 11/295,155, filed on Dec. 6, 2005, now Pat. No. 7,476,734, which is a continuation-in-part of application No. 11/295,406, filed on Dec. 5, 2005, now abandoned, which is a continuation-in-part of application No. 11/286,626, filed on Nov. 22, 2005, which is a continuation-in-part of application No. 11/286,516, filed on Nov. 22, 2005.

(51) Int. Cl.
    *C07H 21/04* (2006.01)

(52) U.S. Cl. .............. 536/24.3; 536/22.1; 536/23.1; 536/24.33; 536/25.3; 536/25.32; 514/42; 514/43; 514/52

(58) Field of Classification Search .............. None
    See application file for complete search history.

(56) References Cited

U.S. PATENT DOCUMENTS

2005/0227231 A1    10/2005    Tcherkassov

OTHER PUBLICATIONS

Kocher et al. PNAS (1989), vol. 86, pp. 6196-6200.*

* cited by examiner

*Primary Examiner* — Patrick T Lewis
(74) *Attorney, Agent, or Firm* — Thomas Meyers; Adam Schoen; Brown Rudnick LLP

(57) ABSTRACT

The invention provides a family of tethered nucleotide analogs useful in sequencing nucleic acids containing a homopolymer region comprising, for example, two or more base repeats, and to sequencing methods using such tethered nucleotide analogs.

24 Claims, 47 Drawing Sheets

Analog C*pCp C5 Parg
HPLC repurified (PB)
5 C template.
100 nM for 5 min per addition (EB)

VIA (X=H), VIB (X=PO₃⁻)

| FIG. 7A |
| FIG. 7B |
| FIG. 7C |

XXV

XXVII

XIXX

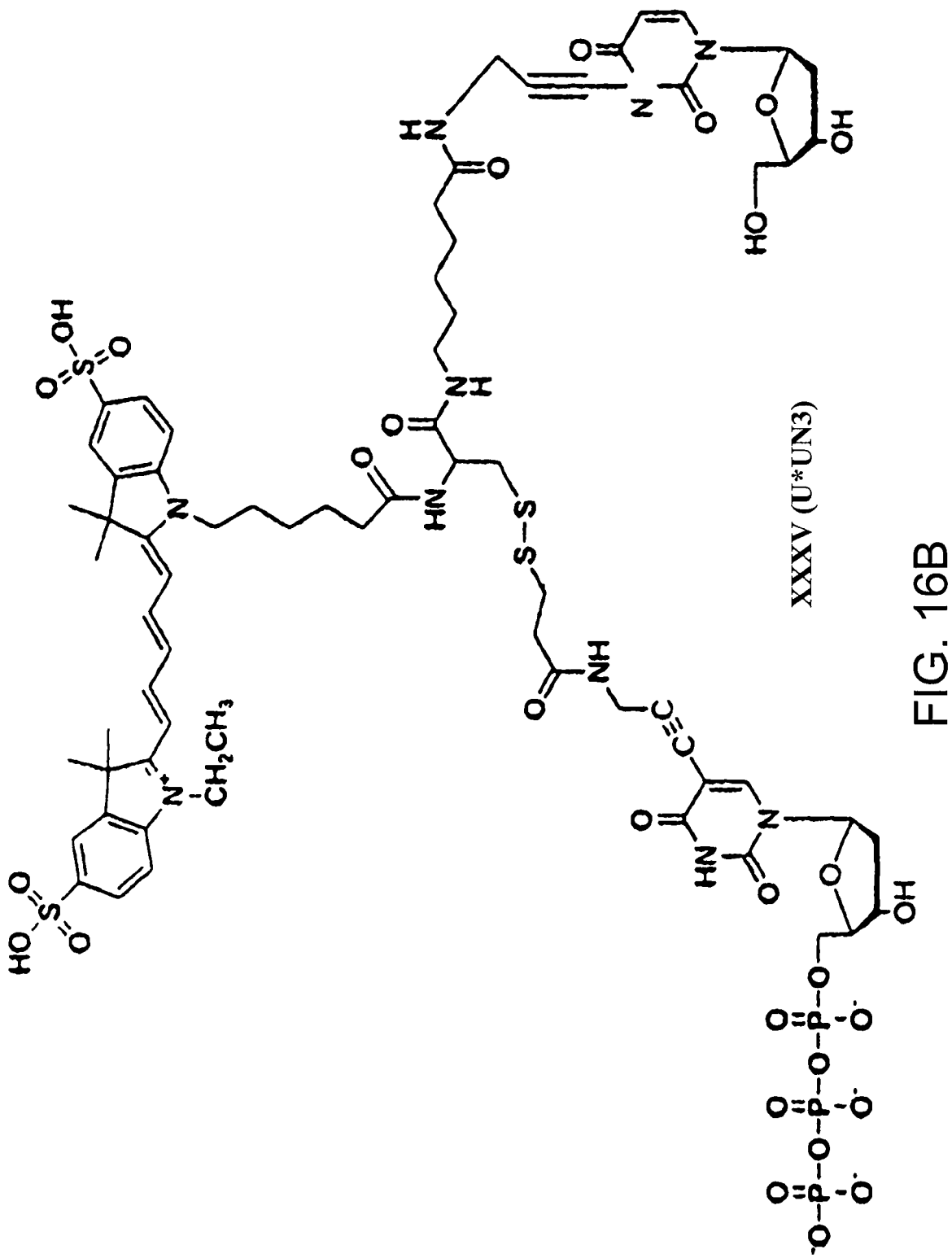
FIG. 16B XXXV (U*UN3)

XXXVI (C*pUN3)

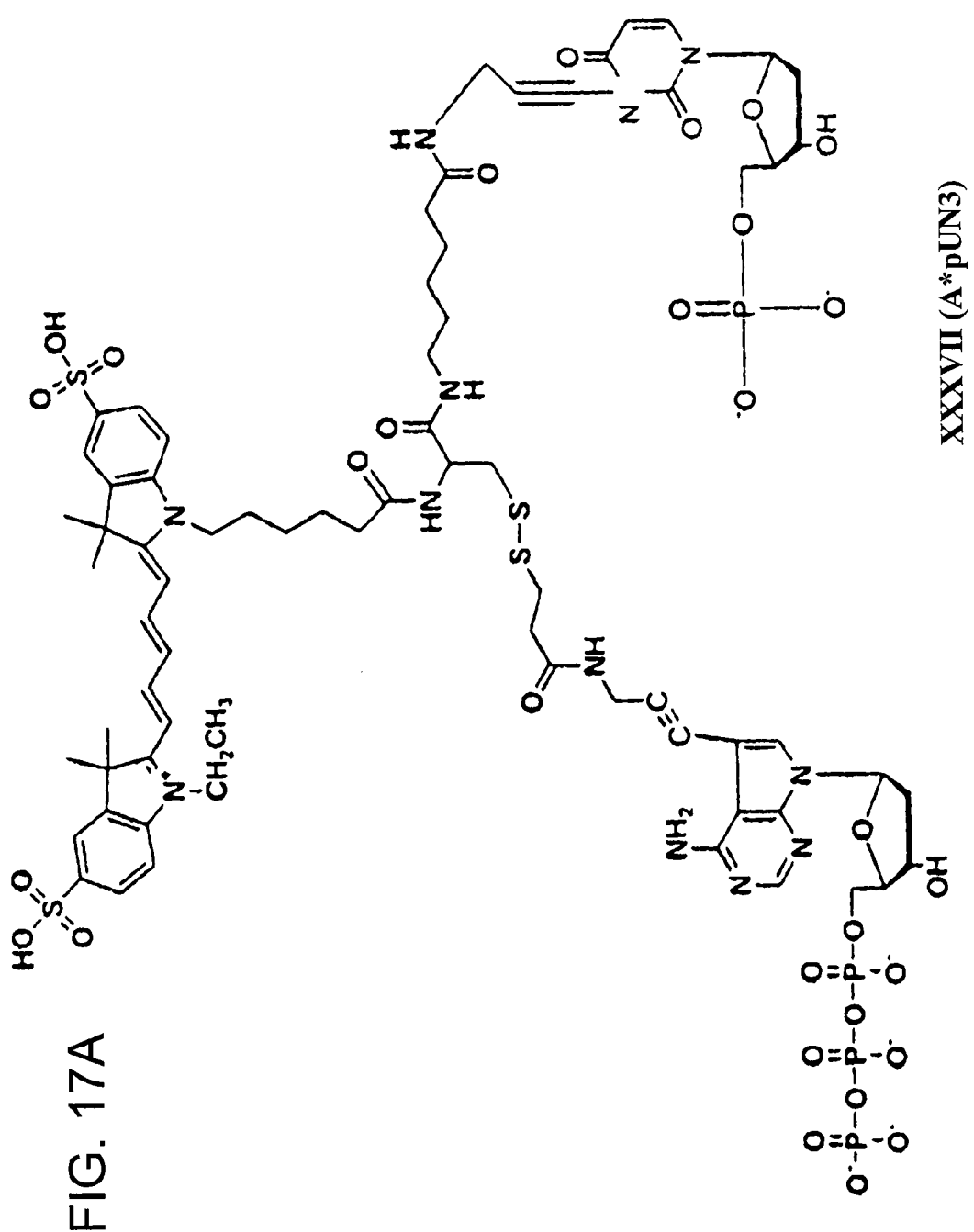

XXXVIII (G*pUN3)

XLI (C*sCpC5Parg Alexa 647)

METHODS AND COMPOSITIONS FOR SEQUENCING A NUCLEIC ACID

CROSS-REFERENCE TO RELATED APPLICATIONS

This application is a continuation of U.S. Ser. No. 11/803,339, filed May 14, 2007, which is a continuation-in-part of U.S. Ser. No. 11/603,945, filed Nov. 22, 2006, which is a continuation-in-part of U.S. Ser. No. 11/496,275, filed Jul. 31, 2006, which is a continuation-in-part of U.S. Ser. No. 11/496,274, filed Jul. 31, 2006, which is a continuation-in-part of U.S. Ser. No. 11/496,262, filed Jul. 31, 2006, which is a continuation-in-part of U.S. Ser. No. 11/295,155, filed Dec. 6, 2006, which is a continuation in part of U.S. Ser. No. 11/295,406, filed Dec. 5, 2005, which is a continuation-in-part of U.S. Ser. No. 11/286,626, filed Nov. 22, 2005, which is a continuation-in-part of U.S. Ser. No. 11/286,516, filed Nov. 22, 2005, all of which are herein incorporated by reference in their entireties.

FIELD OF THE INVENTION

The invention relates to labeled nucleotide triphosphate analogs and methods for polynucleotide sequencing using nucleotide triphosphate analogs.

BACKGROUND

Nucleic acid sequencing-by-synthesis has the potential to revolutionize the understanding of biological structure and function. Traditional sequencing technologies rely on amplification of sample-based nucleic acids and/or the use of electrophoretic gels in order to obtain sequence information. More recently, single molecule sequencing has been proposed as a way to obtain high-throughput sequence information that is not subject to amplification bias. See, Braslavsky, Proc. Natl. Acad. Sci. USA 100: 3960-64 (2003).

Sequencing-by-synthesis involves the template-dependent addition of nucleotides to a support-bound template/primer duplex. The added nucleotides are labeled in a manner such that their incorporation into the primer can be detected. A challenge that has arisen in single molecule sequencing involves the ability to sequence through homopolymer regions (i.e., portions of the template that contain consecutive identical nucleotides). Often the number of bases present in a homopolymer region is important from the point of view of genetic function. As most polymerases used in sequencing-by-synthesis reactions are highly-processive, they tend to add bases continuously as the polymerase traverses a homopolymer region. Most detectable labels used in sequencing reactions do not discriminate between more than two consecutive incorporations. Thus, a homopolymer region will be reported as a single, or sometimes a double, incorporation without the resolution necessary to determine the exact number of bases present in the homopolymer.

One solution to the problem of determining the number of bases present in a homopolymer is proposed in co-owned, U.S. Pat. No. 7,169,560. That method involves controlling the kinetics of the incorporation reaction such that, on average, only a predetermined number of bases are incorporated in any given reaction cycle. The present invention provides an alternative solution to this problem.

SUMMARY OF THE INVENTION

The invention provides methods, compounds and compositions that allow the introduction of a single base at a time in a template-dependent sequencing reaction. The invention allows template-dependent sequencing-by-synthesis through all regions of a target nucleic acid, including homopolymer regions. Thus, the invention also allows for the determination of the number of nucleotides present in a homopolymer region.

The invention contemplates introducing an inhibitor of second nucleotide incorporation in proximity to the active site of incorporation of a first nucleotide. Accordingly, the invention contemplates proximity inhibition in which the concentration of an inhibitor is increased in proximity to the active site of the polymerase, such that a single nucleotide is incorporated but subsequent incorporation is prevented until the inhibition is released.

In one aspect, the invention provides a family of labeled nucleotide triphosphate analogs called virtual terminators. Each virtual terminator comprises three basic components: a Nucleotide 5'-Triphosphate (NTP) or a NTP analog (including ribose NTPs and non-ribose NTPs, such as acyNTPs as shown below), a "tether" or linker that includes a label (such as a fluorescent molecule), and an inhibitor or blocker. The compositions described herein are useful in any sequencing reaction, but are especially useful in single molecule sequencing-by-synthesis reactions. Single molecule reactions are those in which the duplex to which nucleotides are added is individually optically resolvable. An acyNTP analog is one having a variation on the following generalized structure:

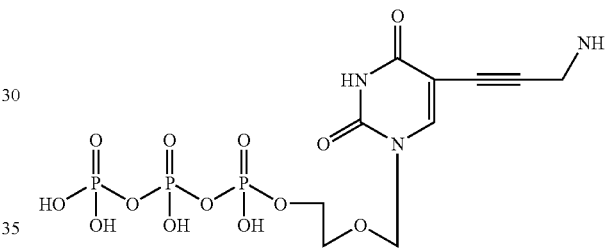

In general, a nucleotide analog of the invention comprises an inhibitor that is tethered to a NTP or a NTP analog to be incorporated in a template-dependent sequencing-by-synthesis reaction. The linker or tether between the NTP or NTP analog to be incorporated and the inhibitor preferably is cleavable so that the inhibitor can be removed after incorporation of the proper base-paired nucleotide. The inhibitor portion can be a specific inhibitor or a non-specific inhibitor of second nucleotide incorporation. In non-specific inhibition, a nucleotide to be incorporated in a sequencing-by-synthesis reaction is linked to a moiety that sterically hinders incorporation of a subsequent nucleotide. In specific inhibition, the inhibitor is itself a competitive inhibitor of polymerase-catalyzed nucleotide addition. In one embodiment, the inhibitor is a nucleotide that is itself unincorporated but that blocks incorporation downstream of the next complementary nucleotide. In one preferred embodiment, a specific nucleotide analog comprises a nucleotide to be incorporated (NTP), a tether moiety, and a non-incorporatable nucleoside or nucleotide portion (inhibitor). The nucleoside or nucleotide may contain either a deoxyribose or ribose sugar or sugar equivalent.

The tethered nucleotide analogs of the invention comprise an optically-detectable label, for example, a fluorescent label. Labels can be attached to the tethered nucleotide analogs at any position using conventional chemistries such that the label is removed from the incorporated base upon cleavage of the cleavable linker or tether. Examples of useful labels are described in more detail below. In a preferred embodiment, the label is bound to the tether moiety.

A tether or linker between the NTP or NTP analog to be incorporated and the inhibitor is from about 4 to about 50 atoms in length, exclusive of the label. Finally, the tether contains a cleavable linkage that allows removal of the blocking portion of the molecule.

The base portion of the nucleotide to be incorporated is selected from the standard Watson-Crick bases and their analogs and variants. In the case of the specific inhibitor, the base portion of the blocking nucleotide is also selected from the standard Watson-Crick bases and their analogs and variants. The incorporated nucleotide and blocking base can be the same or different. Ideally, the blocker is not normally incorporated by a polymerase. Examples include nucleotide monophosphates, diphosphates, bisphosphates or a nucleotide that when, containing the triphosphate portion, includes a modification that renders the analog biologically nonfunctional with a polymerase normally attached at the C5' carbon of the sugar.

In a specific embodiment, the invention provides a tethered nucleotide analog comprising a nucleotide to be incorporated linked to a nucleotide comprising a traditional Watson-Crick base (adenine, guanosine, cytosine, thymidine, or uridine), a sugar for example, a ribose or deoxyribose sugar, and at least one phosphate.

The invention also provides methods for sequencing nucleic acids. In certain methods, a nucleic acid duplex, comprising a template and a primer, is positioned on a surface such that the duplex is individually optically resolvable. A sequencing-by-synthesis reaction is performed under conditions to permit addition of the labeled nucleotide triphosphate analog to the primer while preventing another nucleotide or nucleotide analog from being added immediately downstream. After incorporation has been detected, inhibition is removed to permit another nucleotide to be added to the primer. Methods of the invention allow detection and counting of consecutive nucleotides in a template homopolymer region.

In an embodiment, a method is provided that sequencing nucleic acid polymer templates comprising a) contacting a field of template molecules and primers annealed thereto with a nucleotide triphosphate analog comprising a fluorophore label in the presence of a polymerase to extend said primers by covalent attachment of a said base analog; b) washing the field to remove non-covalently attached base analog; c) detecting fluorescent signals from fluorophores bonded to said templates to determine that an analog has bound thereto; d) applying conditions in the field to sever said severable bond thereby separating said fluorophore from said NTP and leaving a chemical scar; e) repeating steps a) through d); f) conducting multiple cycles of contacting the field of template molecules and primers annealed thereto with an unlabeled nucleotide triphosphate or analog thereof in the presence of a polymerase to extend said primers by covalent attachment of one or more said unlabeled nucleotide triphosphates when the next base on said template is the complement of said nucleotide triphosphate; and g) after at least four unlabeled base addition cycles, repeating steps a) through e).

Specific structures and methods are described below.

DETAILED DESCRIPTION OF THE INVENTION

Figure 1:
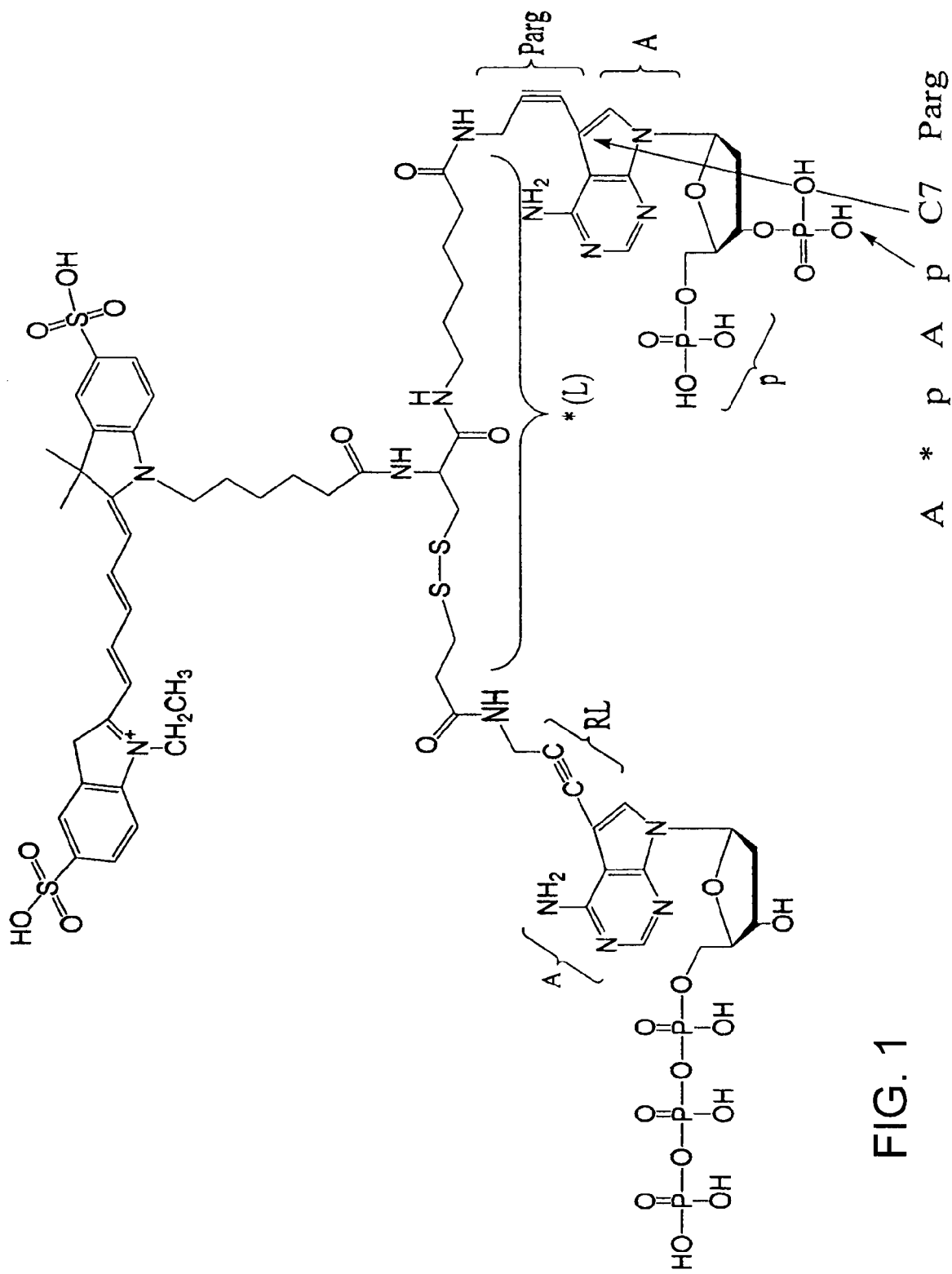
FIG. 1 depicts an exemplary nucleotide analog, and the nomenclature scheme used throughout this disclosure. Starting on the left, the first letter "A", refers to the 7-deaza adenine (the adenine-like structure where C-7 takes the place of N-7) which forms part of the NTP. The symbol "*" following the first letter A refers to the structure including the tether and the label. The next letter ("p") refers to the identity of the chemical moiety on the 5' carbon of the nitrogenous base, here phosphate. The next "A" refers to the nitrogenous base (A, G, C, T or U) tethered to the NTP, and here refers to the adenine analog 7-deaza adenine. "C7" indicates the position in the tethered nitrogenous base where it is attached to the connector (the group bridging between the tether and the nitrogenous base), and refers to the C7 carbon of the 7-deaza adenine. The next symbol, e.g. "Parg," depicts the connector (i.e. propargyl or propynyl).

At least in part, the invention is directed to labeled nucleoside triphosphate analogs, herein referred to as "tethered" analogs, and methods of using such analogs in template-dependent sequencing-by-synthesis. Analogs of the invention comprise a nucleoside triphosphate ("NTP"), or an NTP analog, a tether that may include a label, and an inhibitor. As a consequence of the inhibitor-tether chemical structure, such analogs block or significantly inhibit enzymatic incorporation of second and subsequent NTP analog molecules once a single molecule is added to a growing nucleotide sequence. This property serves to minimize reading through when sequencing DNAs comprising homopolymeric sequence. After data collection involving fluorophore detection, the NTP analog is chemically changed to remove the fluorophore label and most of the structure of the tether, permitting addition of another NTP analog in the next cycle.

Specific examples of these analogs are provided below for illustrative purpose and in order to demonstrate methods of synthesis. However, the skilled artisan will appreciate that numerous variations are possible, consistent with the scope of the appended claims.

I. Nucleotide Analogs

Nucleotide analogs of the invention have the generalized structure of Formula I:

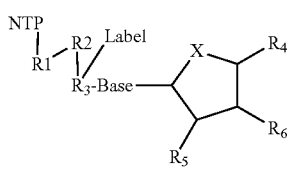

I wherein:

NTP is a nucleoside triphosphate or analog thereof recognizable by a polymerase enzyme and capable of incorporating onto the 3' end of a primer portion of a nucleic acid duplex molecule.

The designation "X" can be O, N, S, or $CH_2$. The R1 group is a linker, which may be any suitable moiety for linking the NTP to the label and inhibitor. Preferred linkers are alkyl, alkynyl, aryl groups and substituted versions of them. The R2 designation represents a cleavable bond or group, such as a disulfide bond, amide bond, thioamide, bond, ester bond, thioester bond, vicinal diol bond, or hemiacetal. Other cleavable bonds include enzymatically-cleavable bonds, such as peptide bonds (cleaved by peptidases), phosphate bonds (cleaved by phosphatases), nucleic acid bonds (cleaved by endonucleases), and sugar bonds (cleaved by glycosidases). The R3 designation is a linker between the cleavable bond or group and the nitrogenous base (or analog) of the blocker nucleotide analog. That linker may be the same as or different from the R1 linker and may include an amide, ester, ether, alkyl, alkynyl, or aryl portion and substituted versions of them. The R4 designation can be SH, OH, or one of the following:

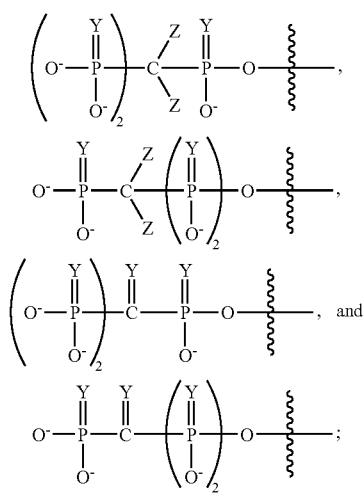

Y, at each occurrence, independently is O or S;

and Z represents H or a halogen. Finally, R5 and R6 independently can be OH, and $PO_4$.

The nitrogenous base portion of the nucleoside triphosphate can be a purine, a pyrimidine, or a purine or pyrimidine analog. The base portion can also be, for example, naturally-occurring and synthetic derivatives of a base, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine. When base portion of the NTP are depicted using the shorthand A, G, C, T or U, each letter refers to the representative base and/or analogs thereof, e.g A includes adenine or adenine analogs, e.g. 7-deaza adenine).

The nitrogenous base of the NTP can be bonded at any chemically appropriate position to the linker. Independently, the nitrogenous base NB can be bonded at any chemically appropriate position to the tether-nitrogenous base connector $R_1$. For example, the base can be deaza A or deaza G and $R_1$ is linked to the C-7 or C-8 positions of the deaza A or G. In other embodiments, the base can be T, C, or U and $R_1$ can be linked to the N-3 or C-5 positions of T, C, or U. The $R_1$ linker can also be attached at the N4 or 06 positions on the base.

The label is preferably an optically-detectable label. Such optically-detectable labels include for example, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5' 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbellif-eroneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'tetramethyl-6-carboxyrhodamine (TAMRA); tetramethyl rhodamine; tetramethyl rhodamine isothiocyanate (TRITC); riboflavin; rosolic acid; terbium chelate derivatives; Cyanine-3 (Cy3); Cyanine-5 (Cy5); Cyanine-5.5 (Cy5.5), Cyanine-7 (Cy7); IRD 700; IRD 800; Alexa 647; La Jolla Blue; phthalo cyanine; and naphthalo cyanine. Preferred labels are fluorescent dyes, such as Cy5 and Cy3. Labels other than fluorescent labels are contemplated by the invention, including other optically-detectable labels. Labels can be attached to the nucleotide analogs of the invention at any position using standard chemistries such that the label can be removed from the incorporated base upon cleavage of the cleavable linker or tether.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like.

Nucleotide analogs described herein permit template-dependent incorporation of a single nucleotide. The term base pair encompasses not only the standard AT, AU or GC base pairs, but also base pairs formed between nucleotides and/or nucleotide analogs comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the nucleotide analog inosine and adenine, cytosine or uracil.

Upon cleavage of the cleavable bond, R2, the incorporated nucleotide will have a residual chemical group that comprises some portion of the linker R1. In certain analogs, as shown below, the residual portion of the linker is minimized in order that the incorporated nucleotide appears chemically as close as possible to a natural nucleotide. In some analogs the residual portion of the linker, or "scar", contains a reactive moiety that must be chemically neutralized. For example, upon cleavage of a disulfide bond, the residual —SH group is "capped", for example by use of iodoacetamide, to produce and unreactive —S—CH$_2$—CONH$_2$ group. Upon cleavage, preferred analogs of the invention produce a residual that is unreactive and does not need to be chemically neutralized. This increases the ease with which a subsequent base can be incorporated during sequencing of a nucleic acid polymer template. For example, conditions include the use of TCEP, DTT and/or other reducing agents for cleavage of a disulfide bond. A selectively severable bond that includes an amido bond can be cleaved for example by the use of TCEP or other reducing agents, and/or photolysis. A selectively severable bond that includes an ester bond can be cleaved for example by acidic or basic hydrolysis.

An exemplary mechanism of cleavage of the cleavable bond of an analog of the invention and the resulting the "short scar" elimination is shown below:

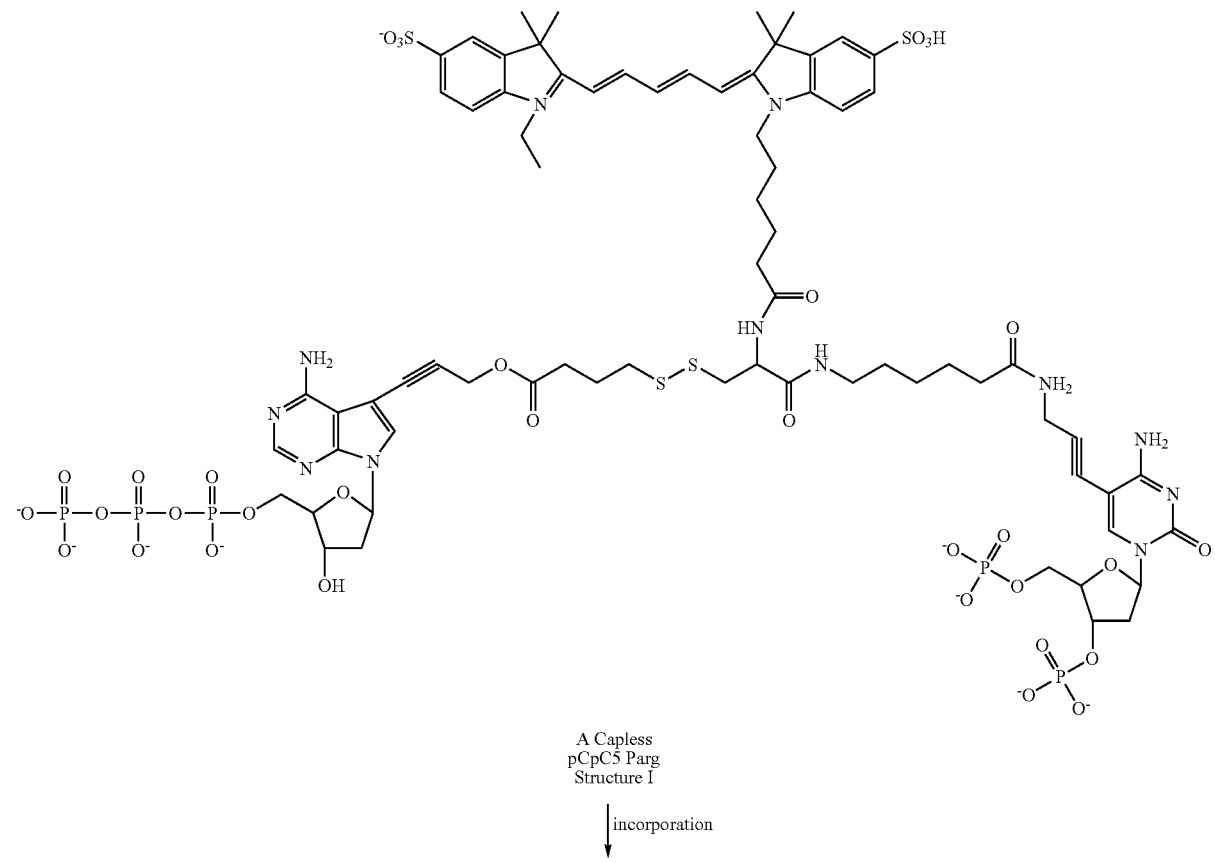

A Capless
pCpC5 Parg
Structure I

↓ incorporation

-continued

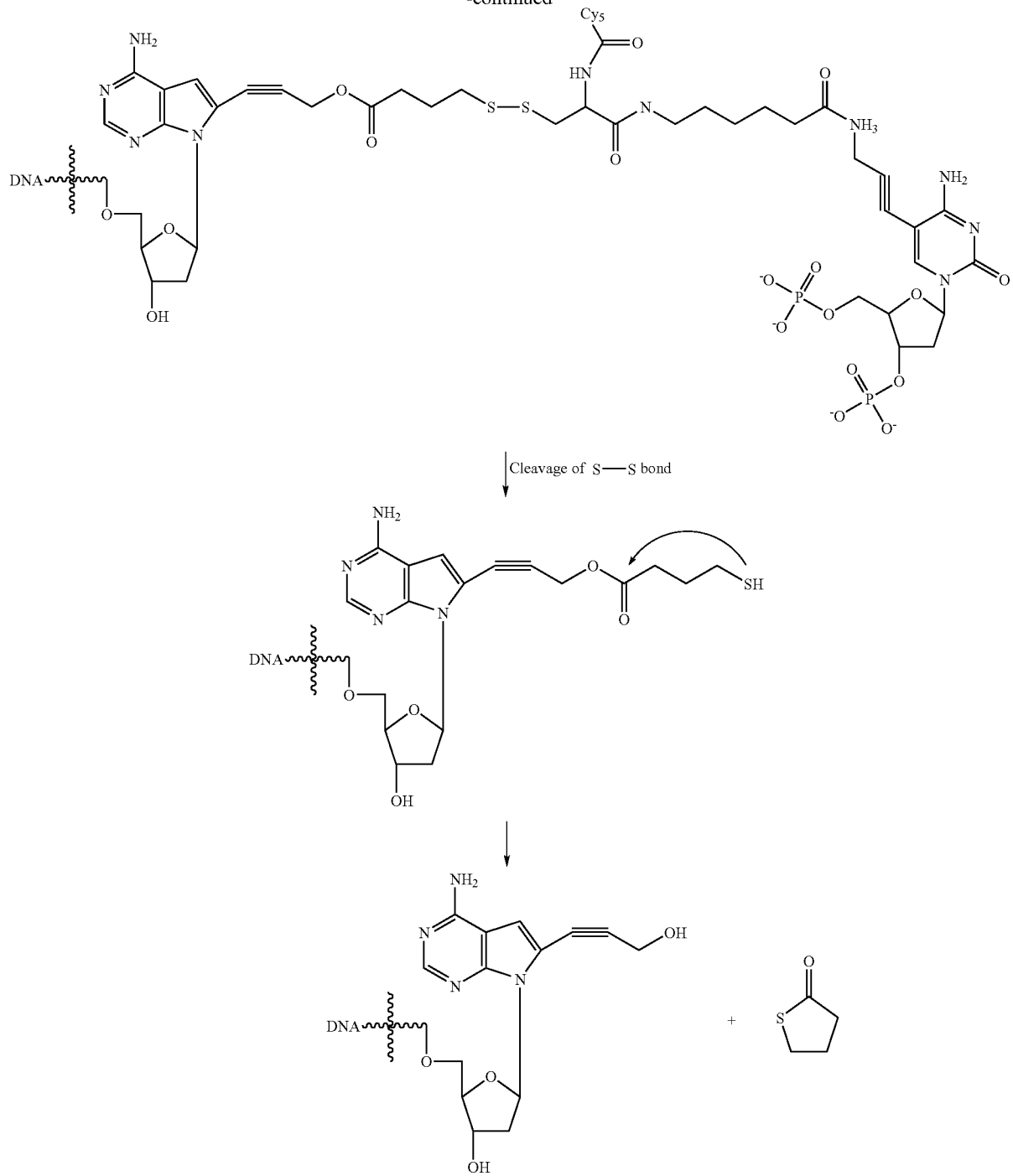

FIG. 1 depicts an exemplary nucleotide analog of the invention and the abbreviated nomenclature used throughout this disclosure in reference to the nucleotide analogs of the invention. In the claims that follow, the tether refers to all structure bridging from the NTP and the NTP-tether moiety, inclusive of the fluorophore (depicted for example, in FIG. 1 as Cy5), to the tether-nitrogenous base connector $R_1$. The remaining structure (depicted, for example, as pApC7 Parg in FIG. 1) is the inhibitor.

Figures 5, 5A:
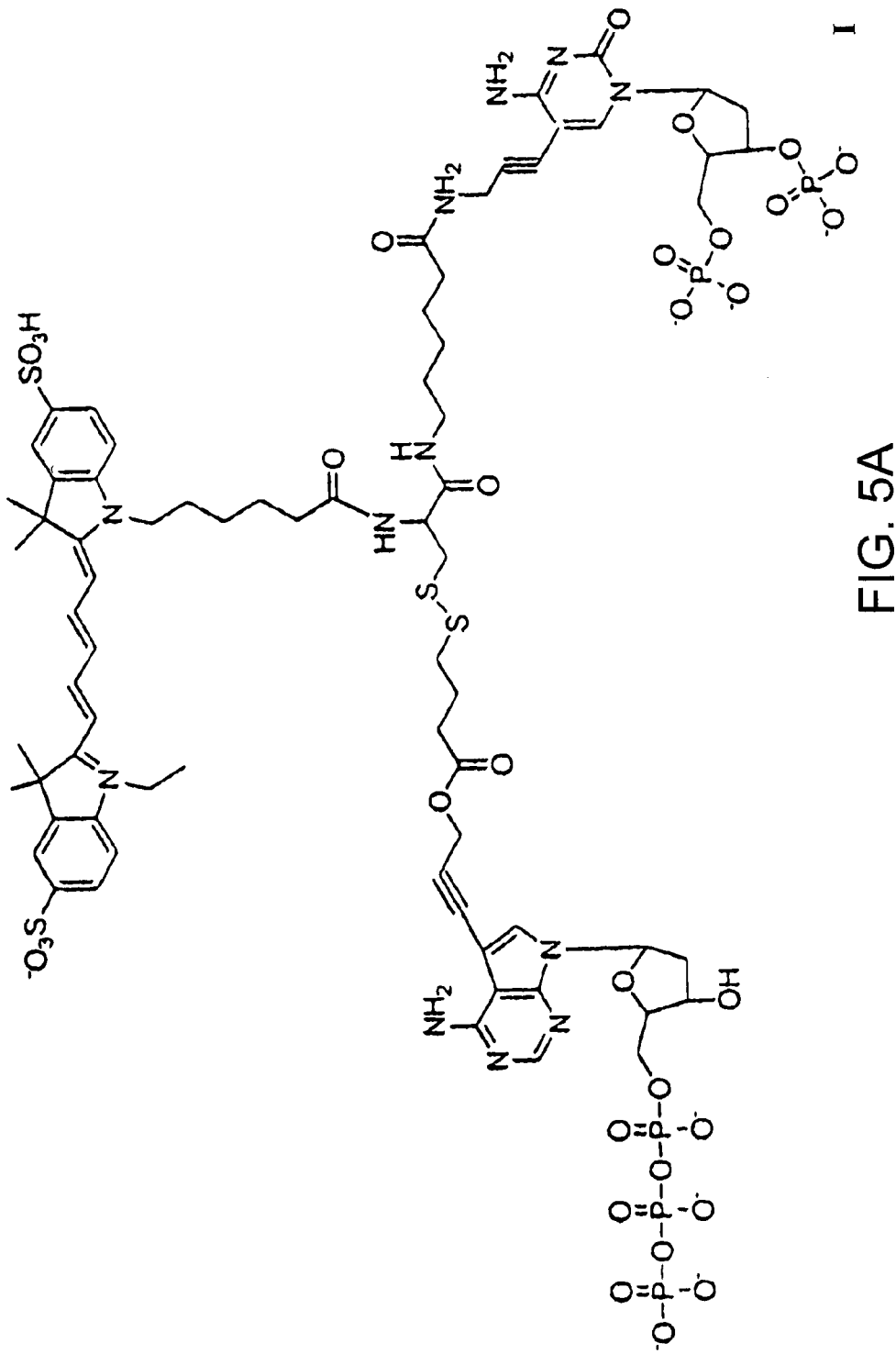
FIGS. 5-18 depict various nucleotide analogs of the invention.
Figure 5B:
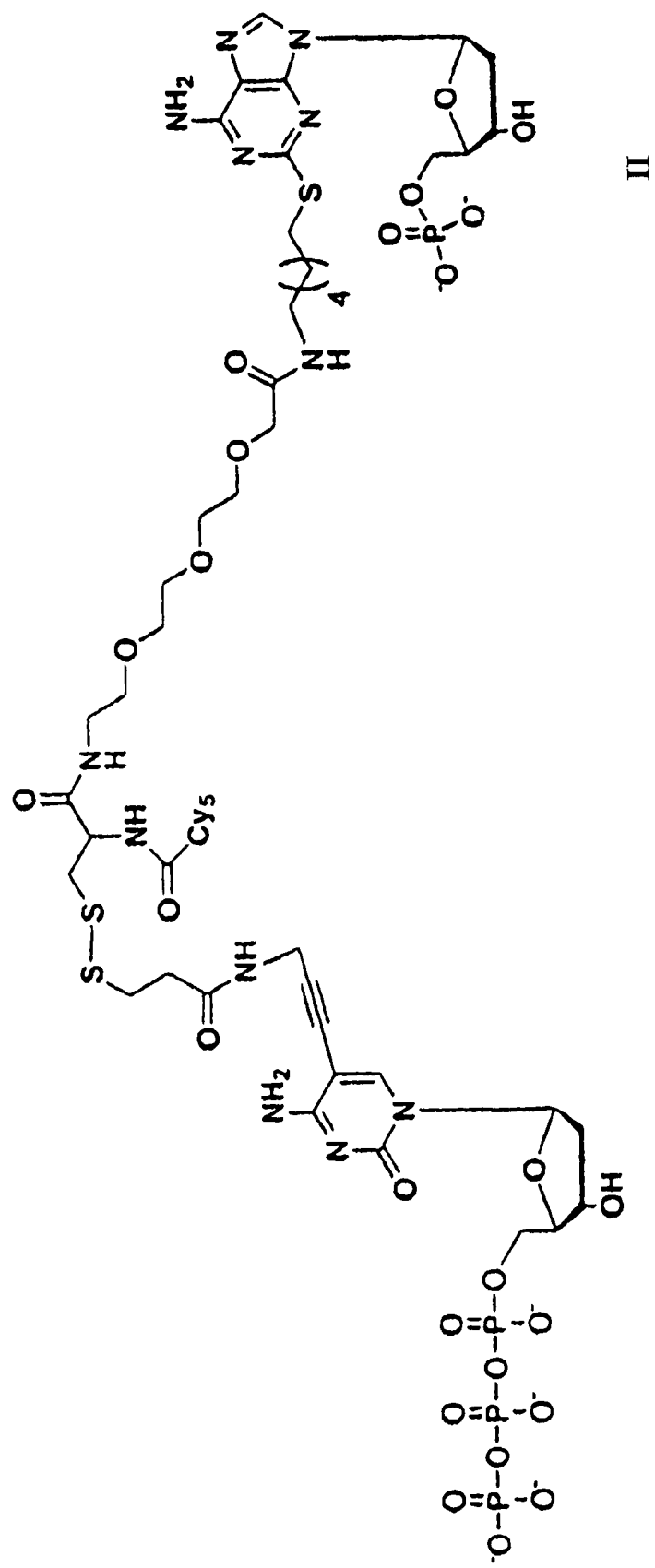
Figure 5C:
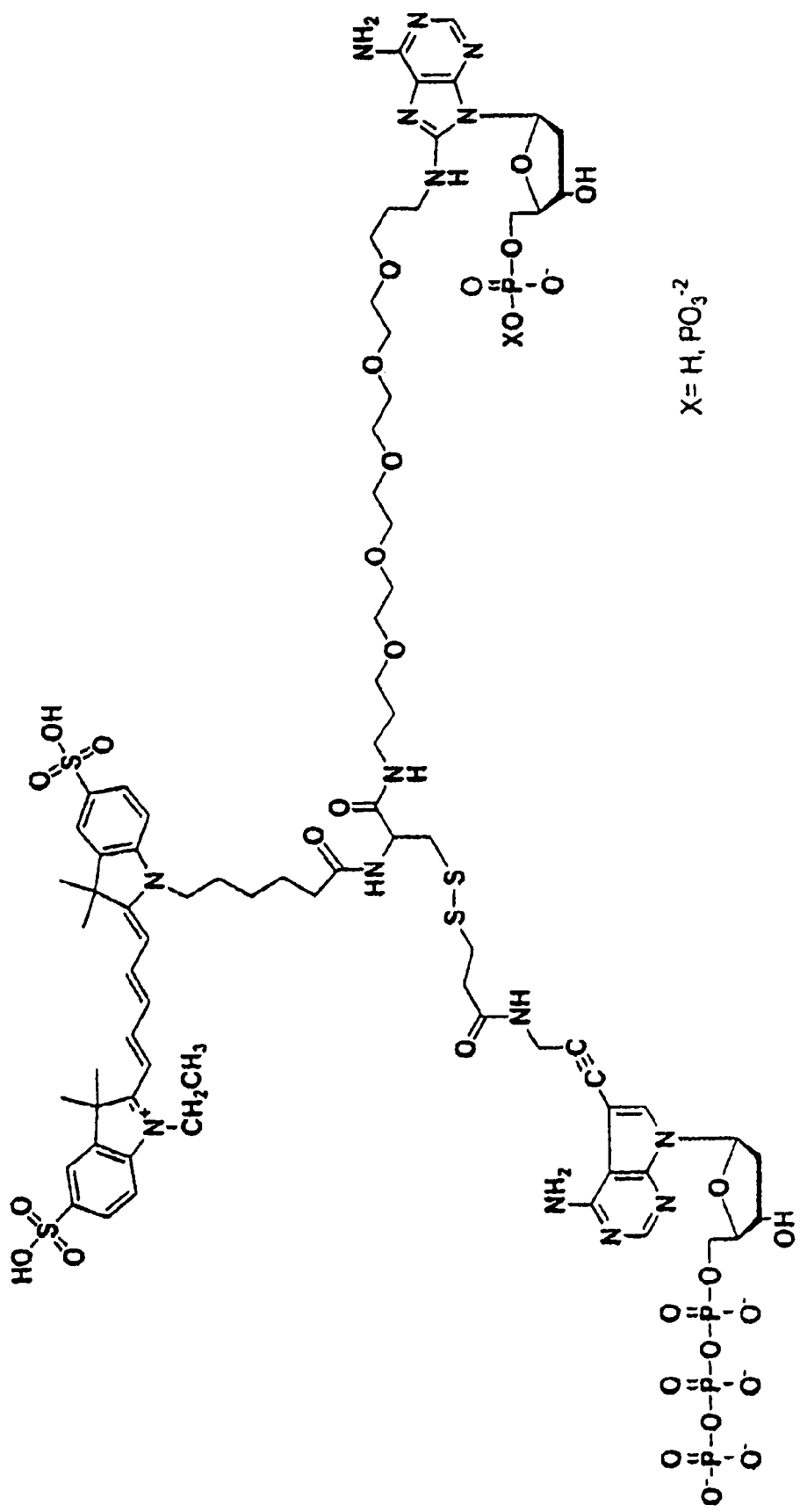
Figure 6A:
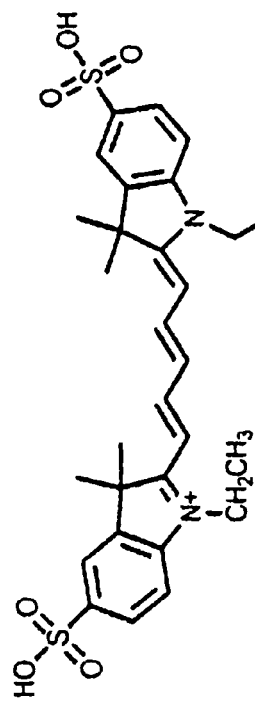
Figure 6A:
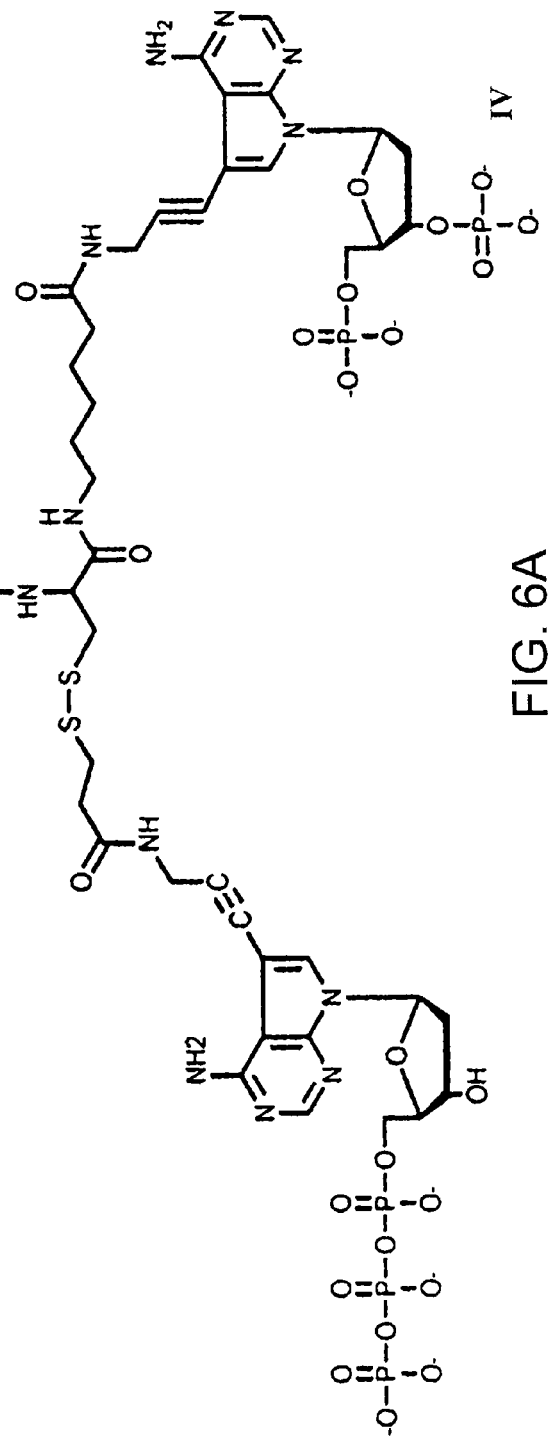
Figure 6B:
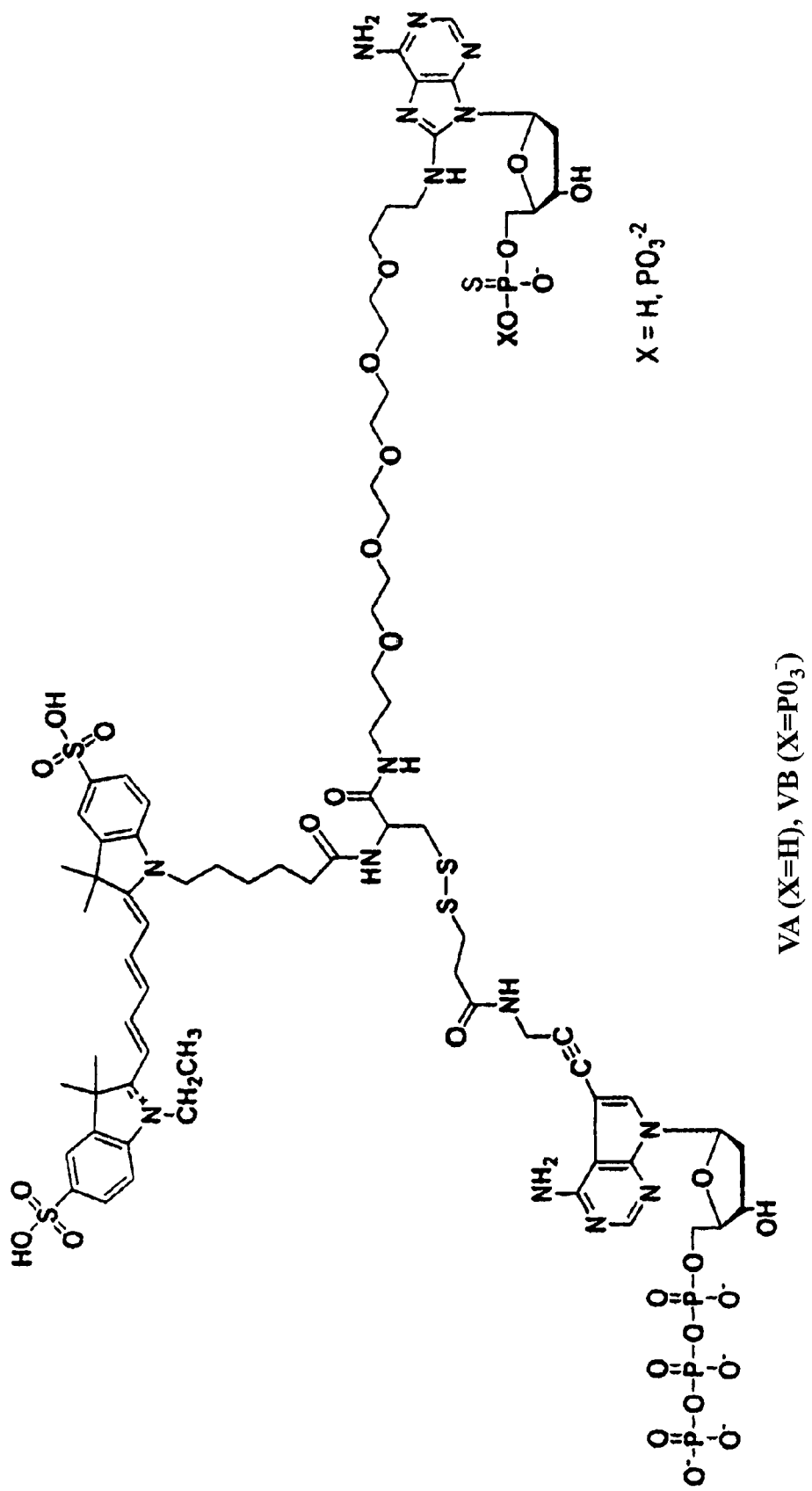
Figure 6C:
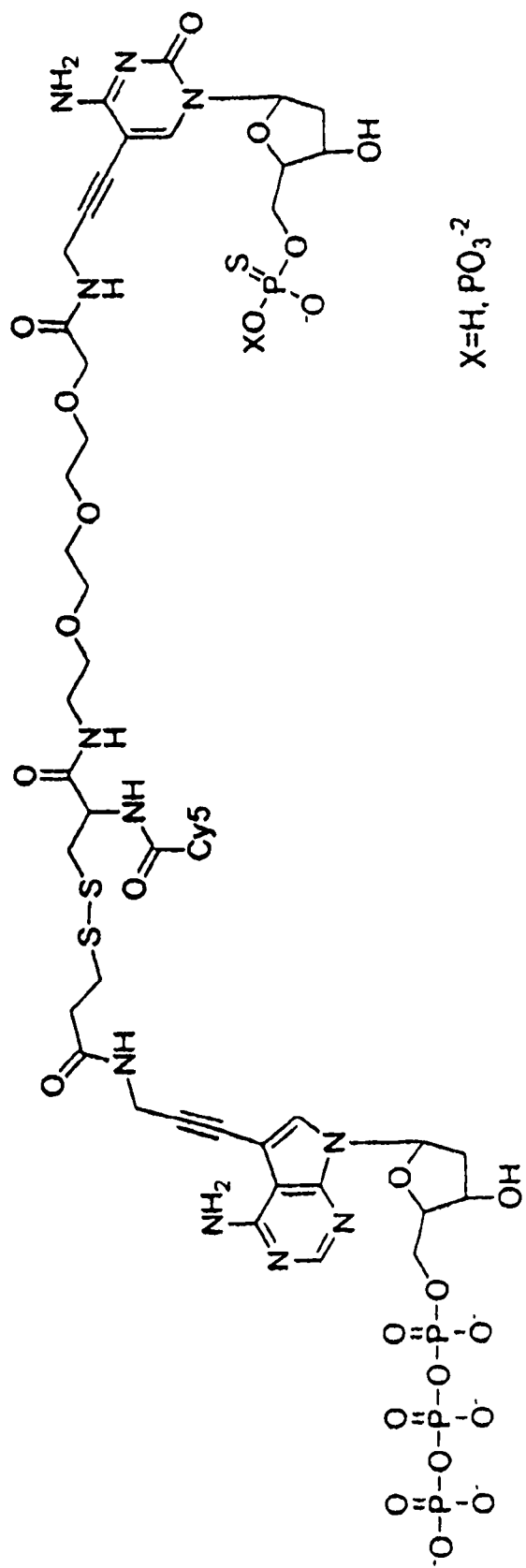

Table I correlates disclosed compounds with the abbreviation exemplified in FIG. 1:

| Nucleotide Analog | Abbreviation |
|---|---|
| Compound I in FIG. 5 | A*pCp C5 Parg Capless; A refers to 7-dezea adenine; C refers to cytosine; p preceding C refers to —$PO_4^{-2}$ at $R_4$ position; the p following C refers to —$PO_4^{-2}$ at $R_2$ position; C5 refers to the Parg (propargyl or propynyl) connector bonded at the $5^{th}$ carbon of C. |

-continued

Figures 7, 7A:
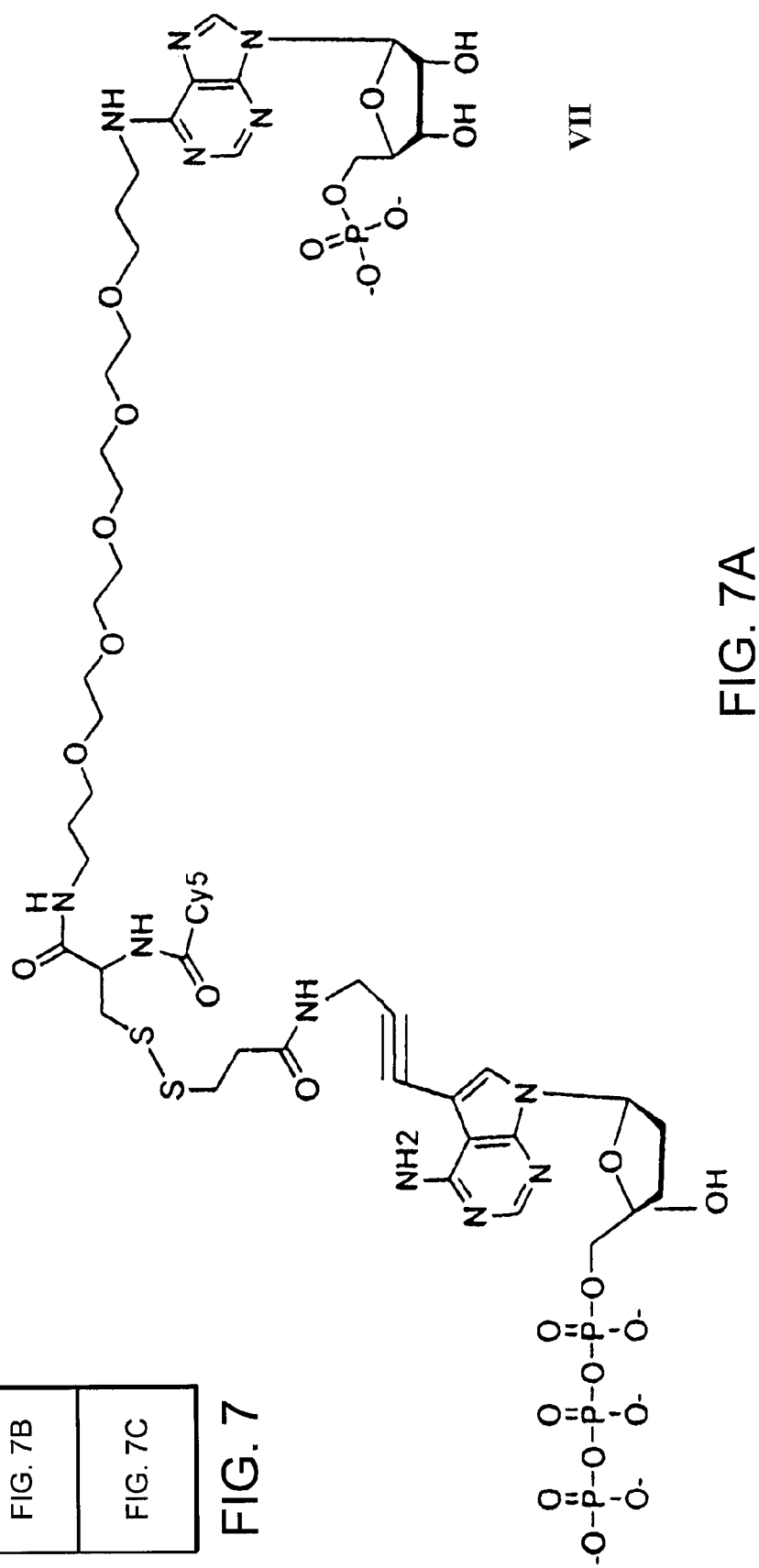
Figure 7B:
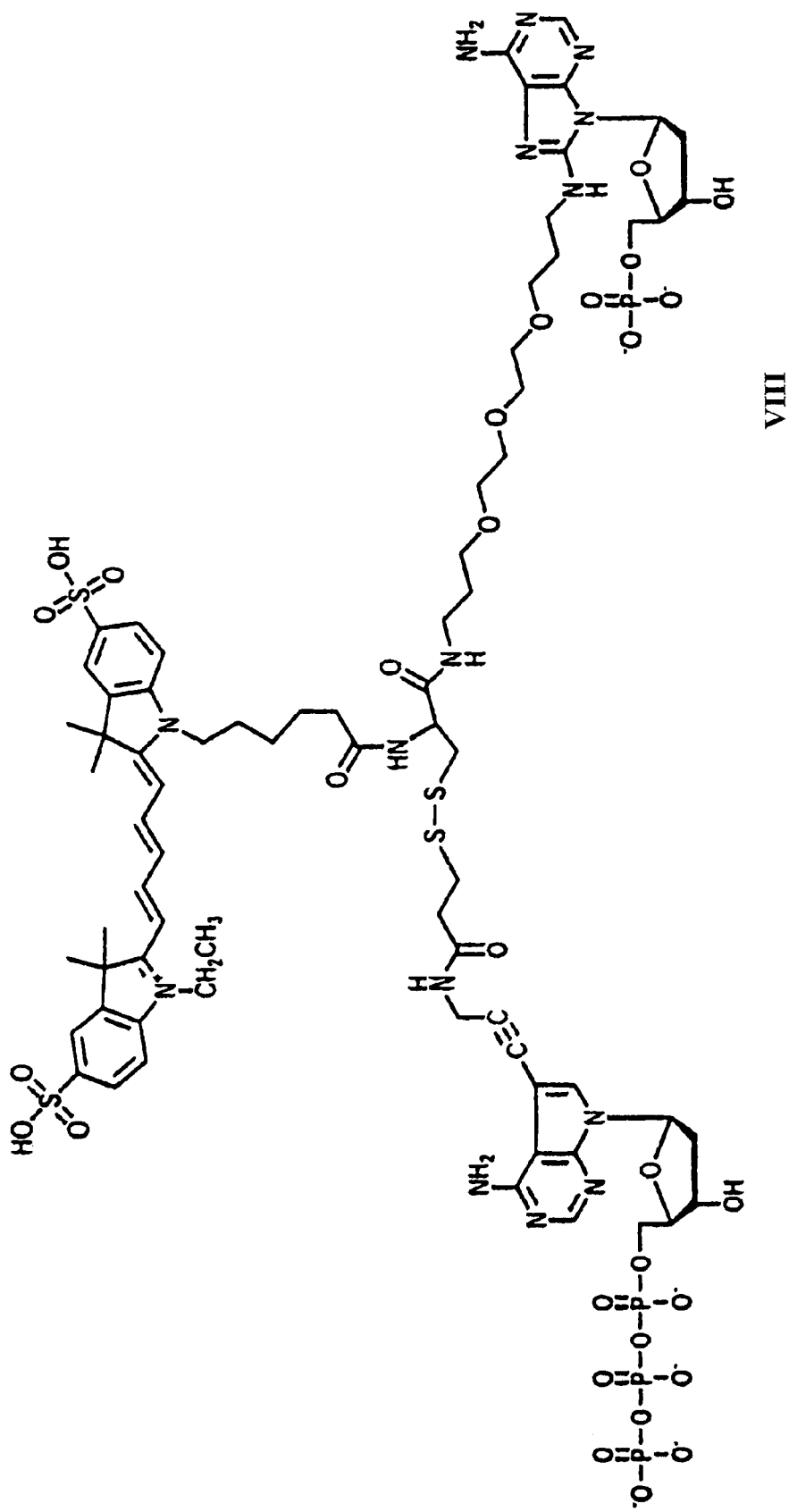
Figure 7C:
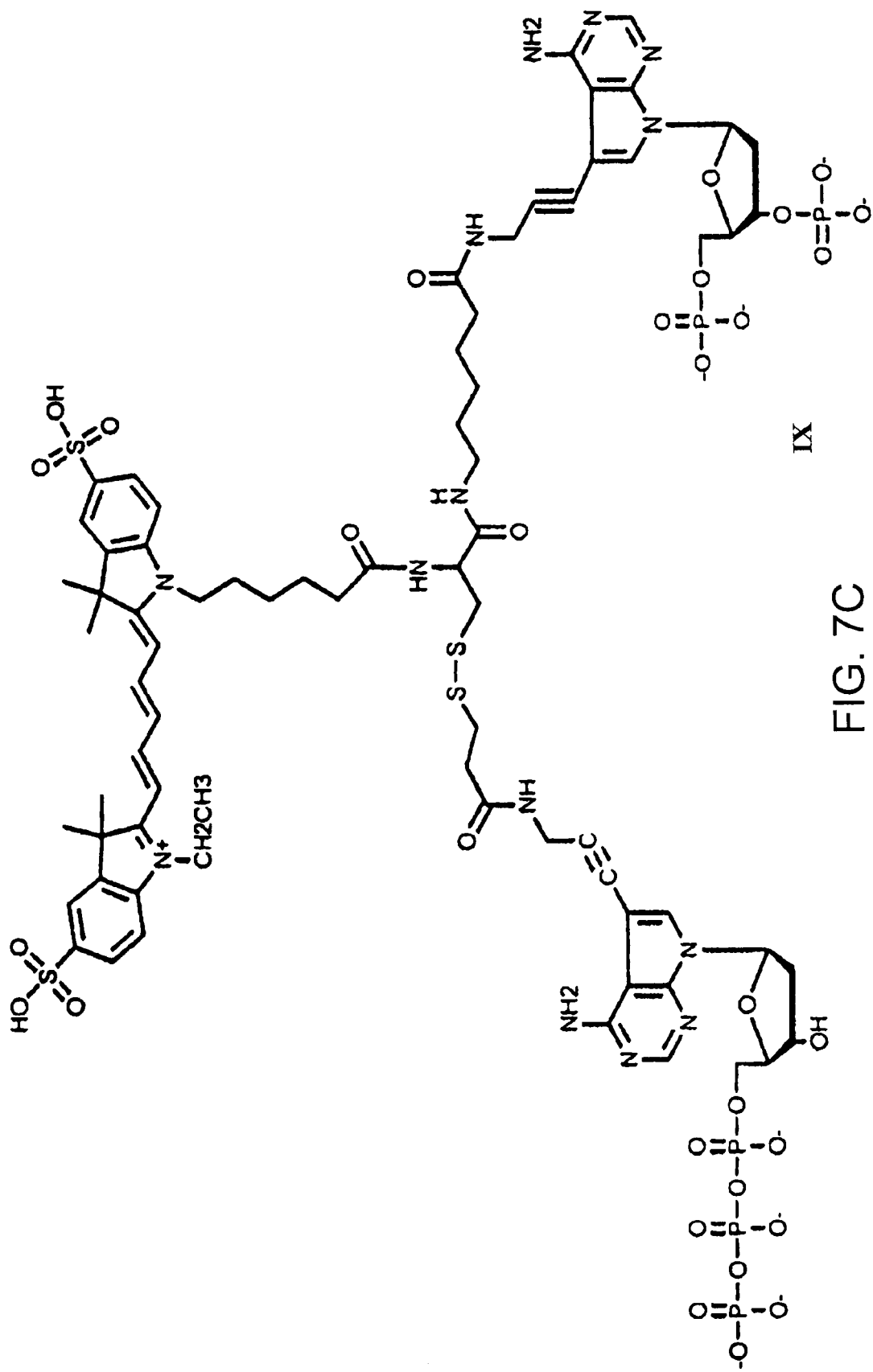
Figures 8, 8A:
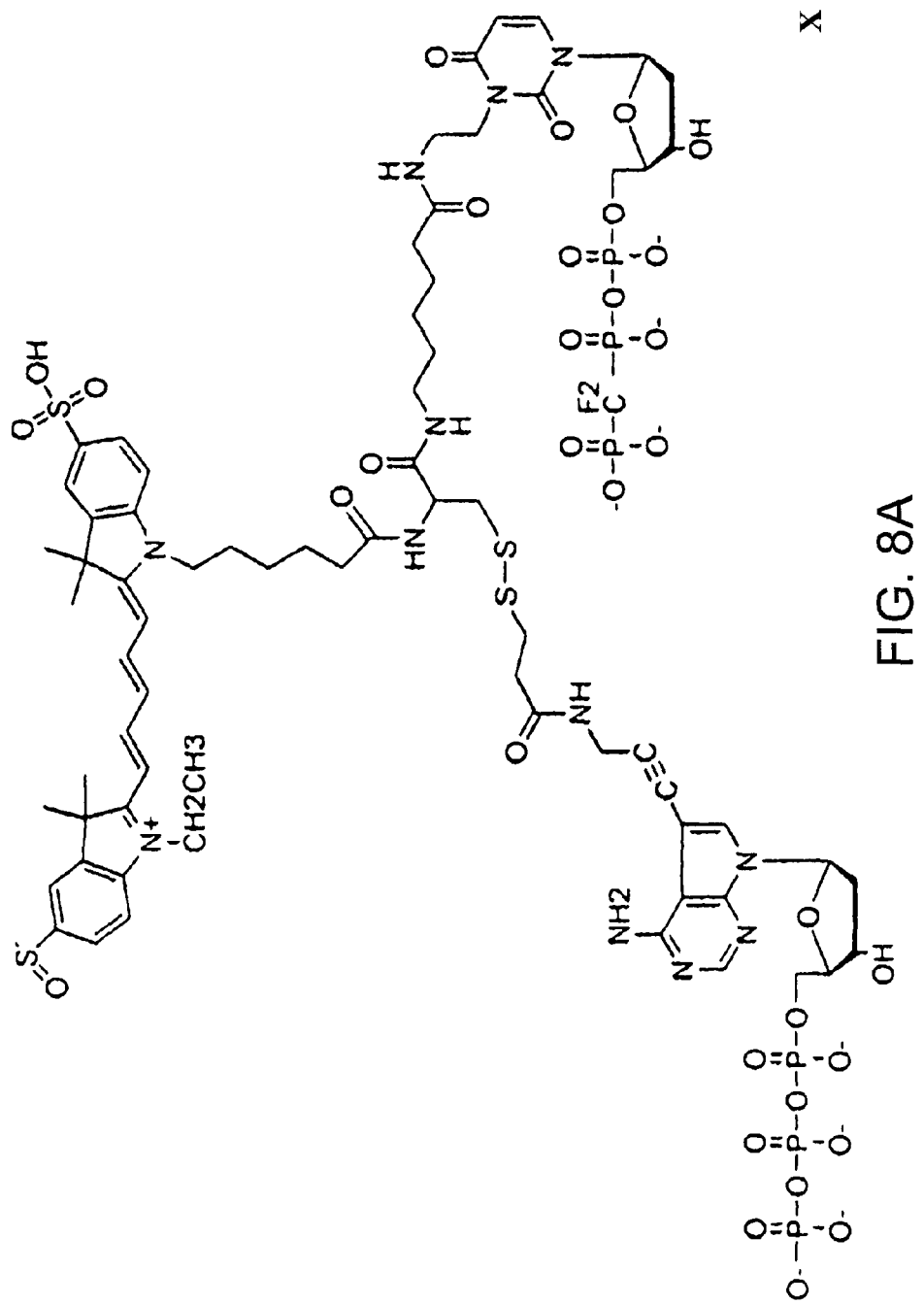
Figure 8B:
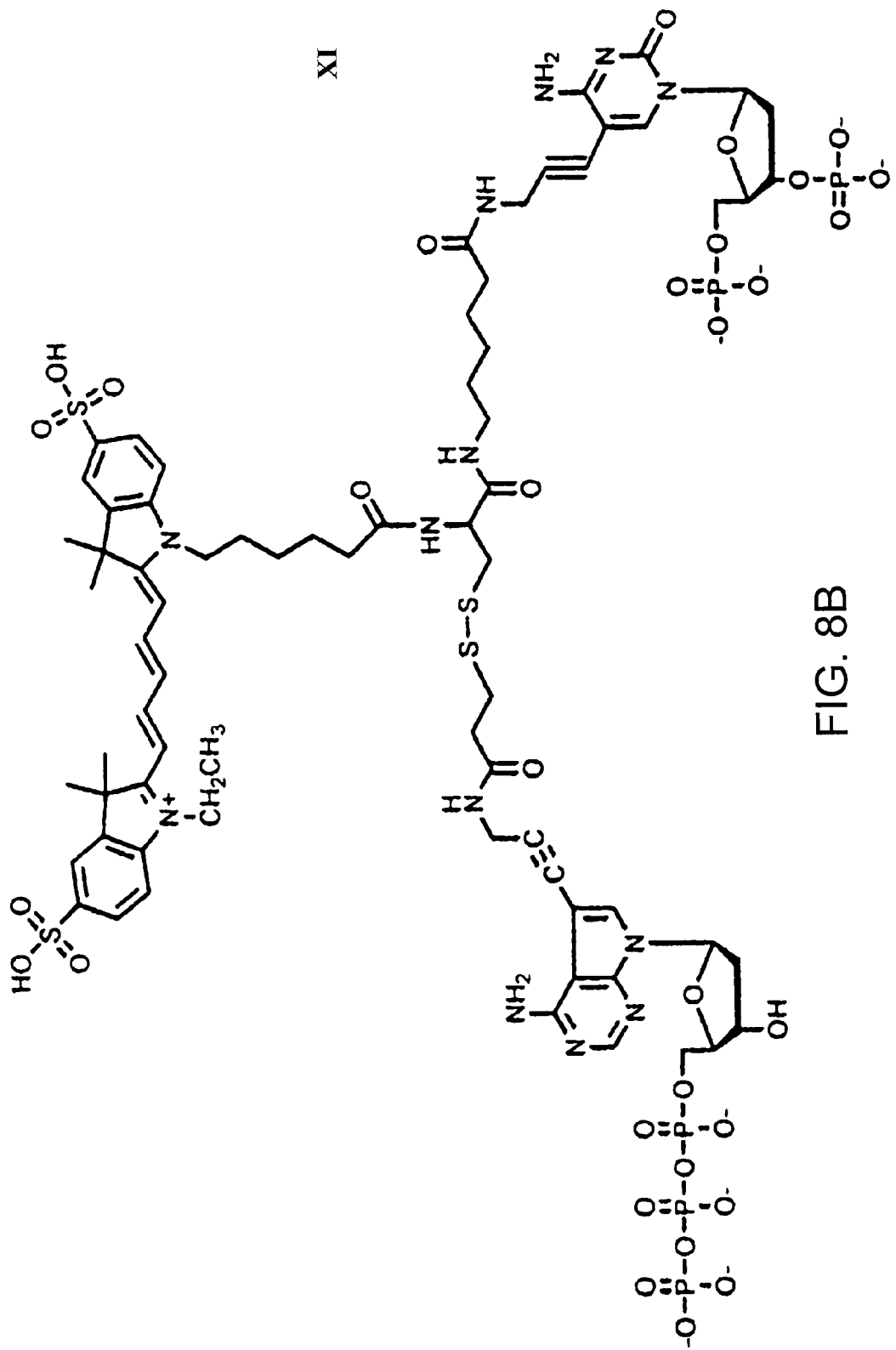
Figure 8C:
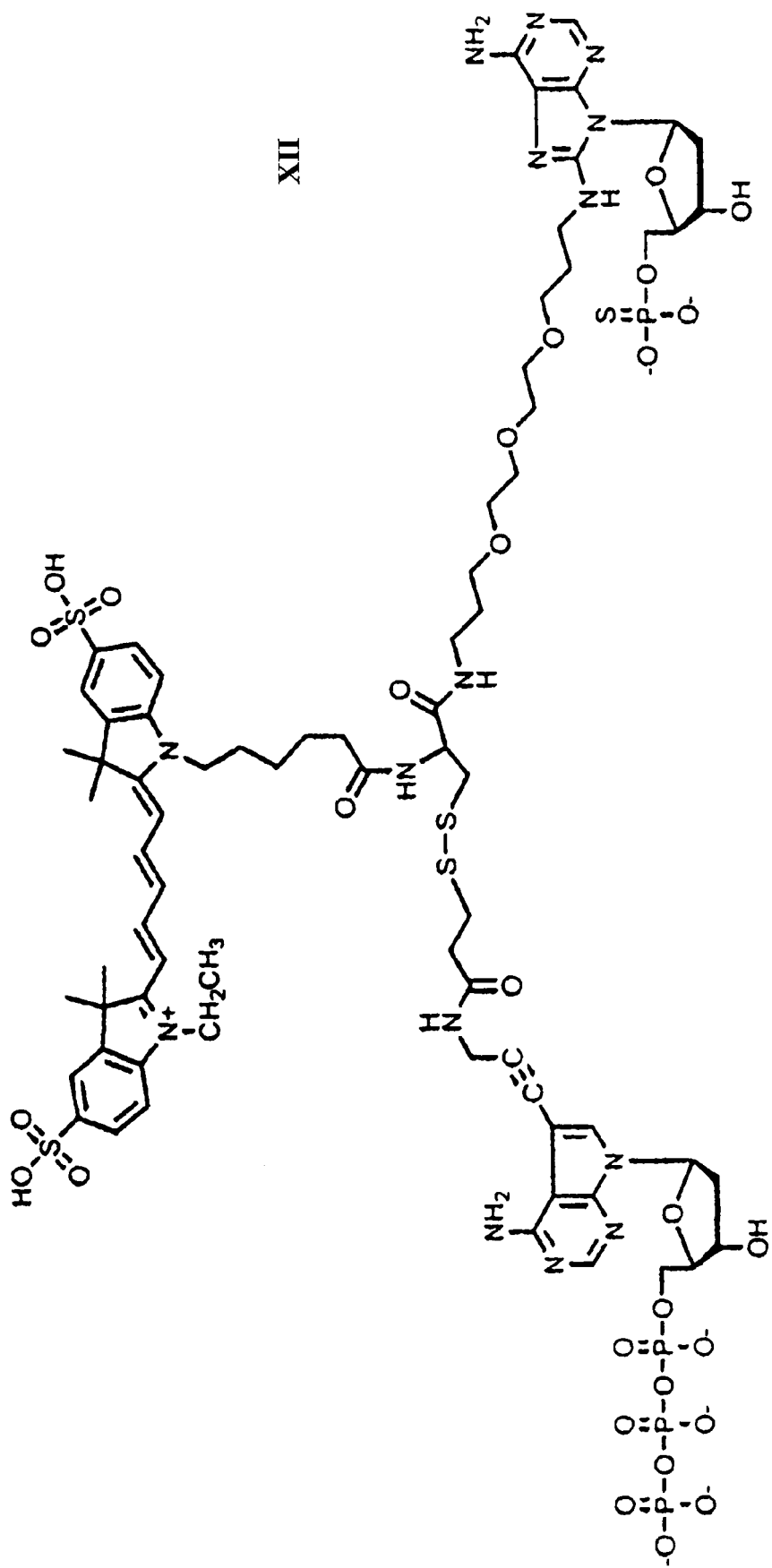
Figure 9A:
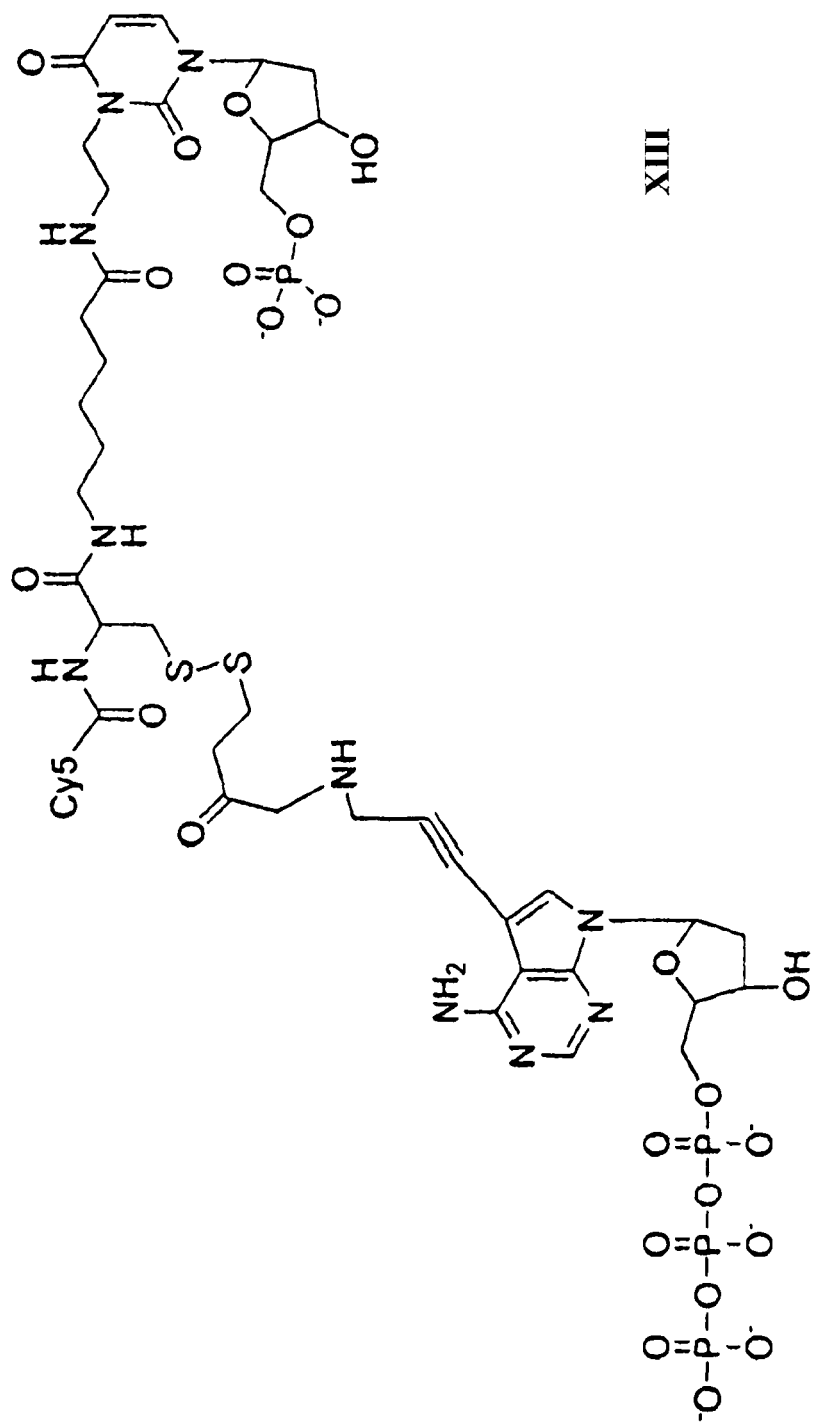
Figure 9B:
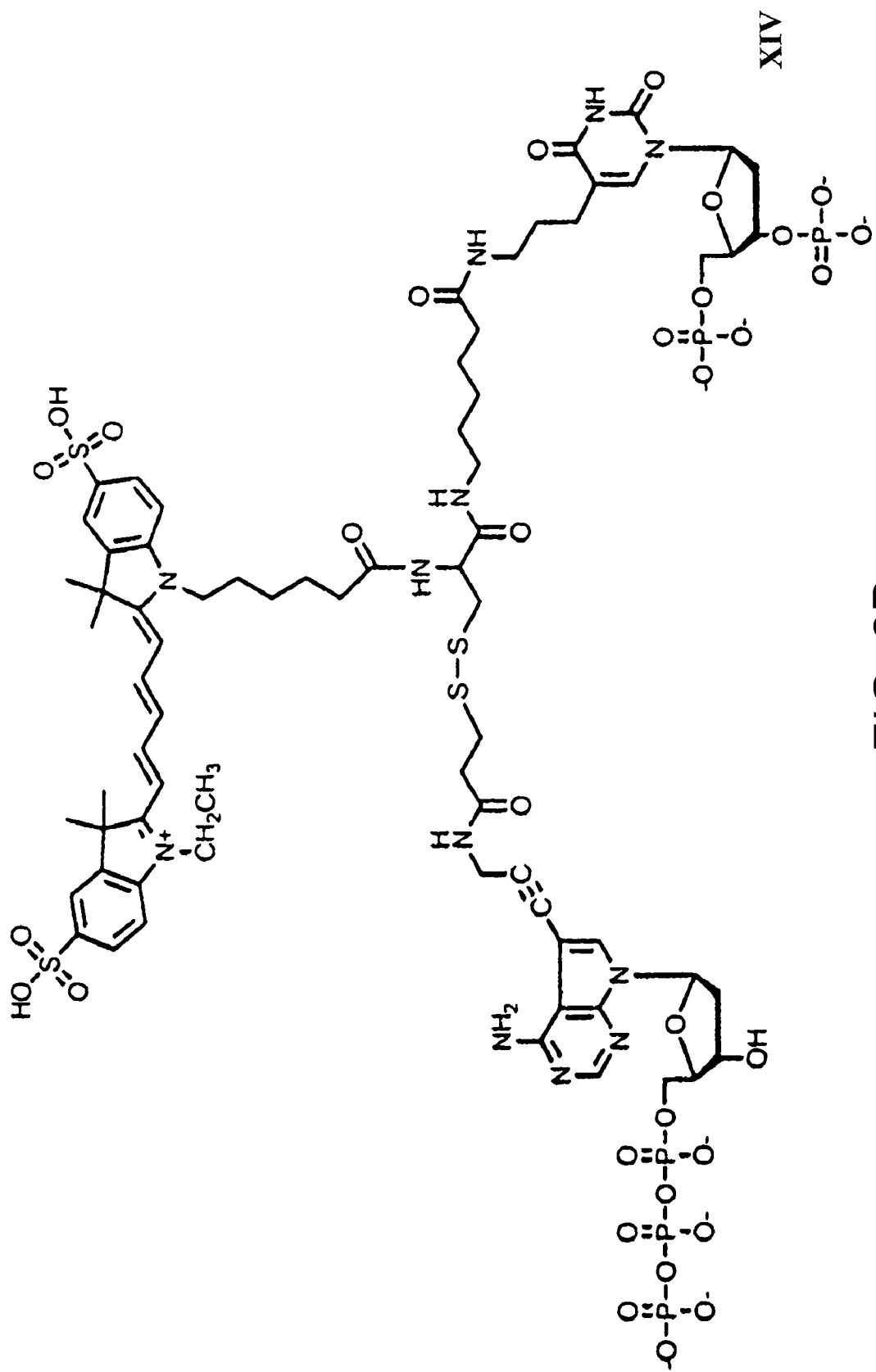
Figure 9C:
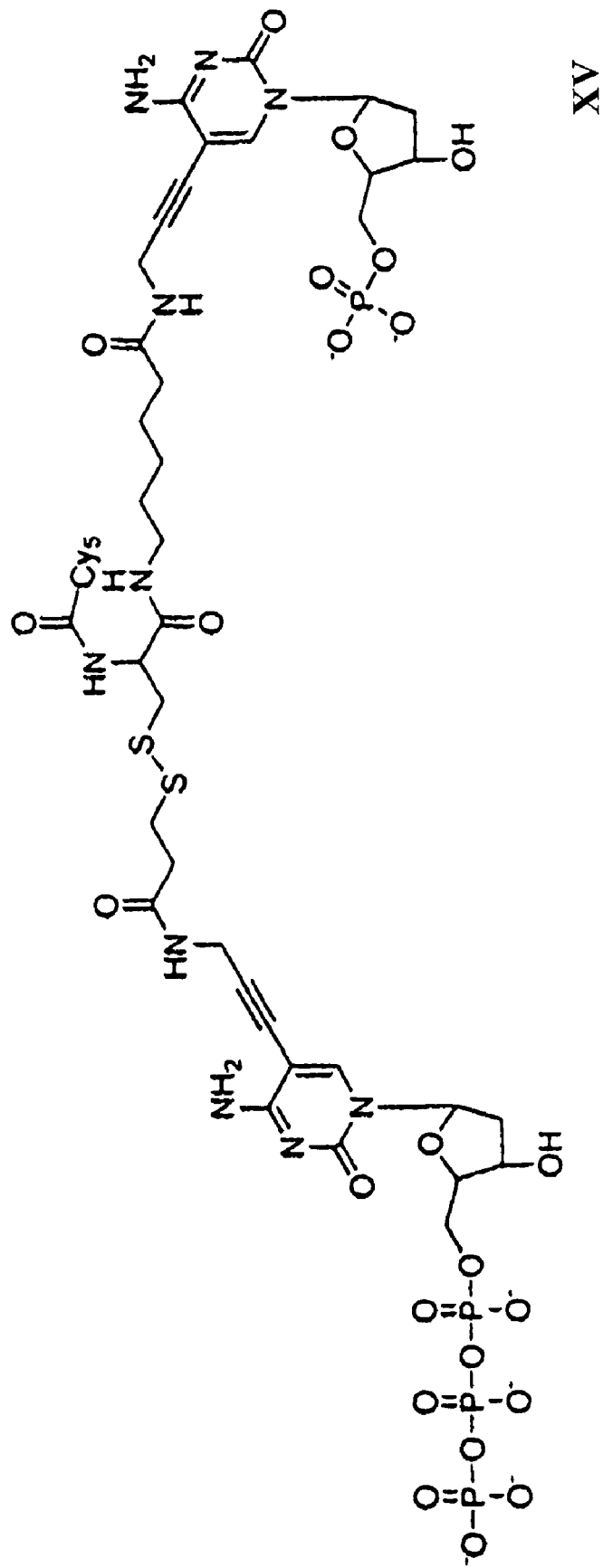
Figure 10:
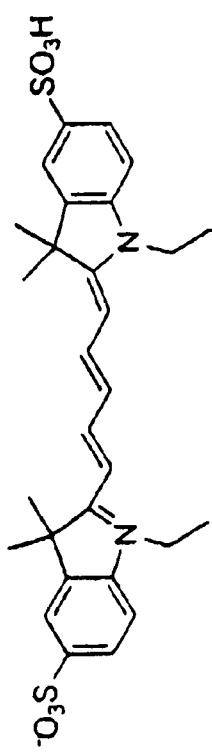
Figure 10A:
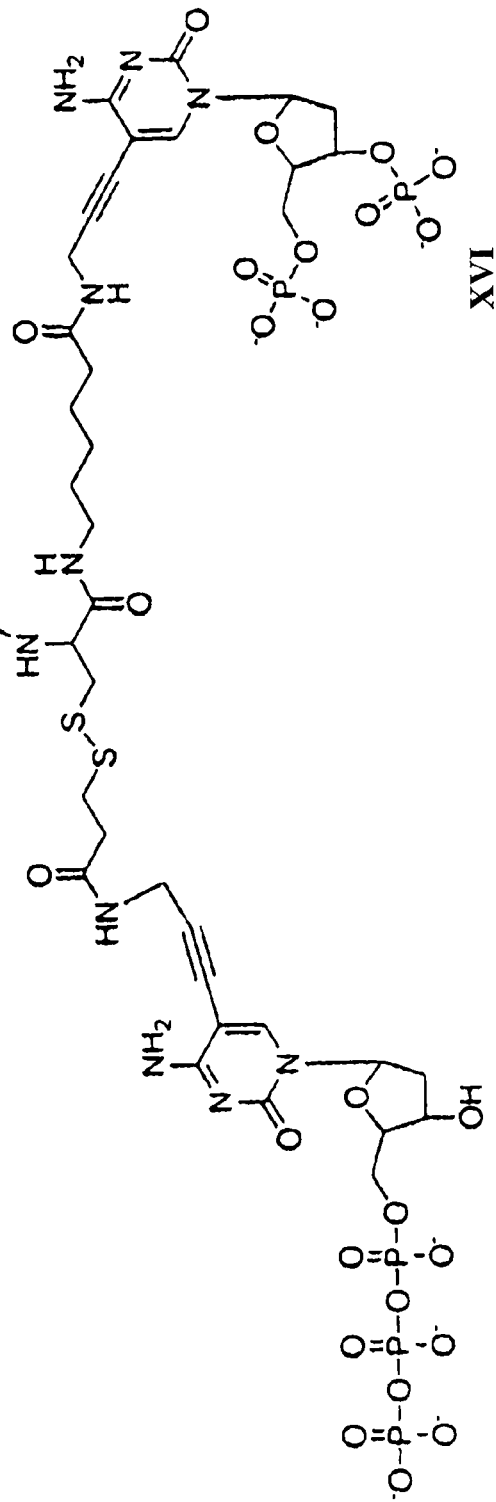
Figure 10B:
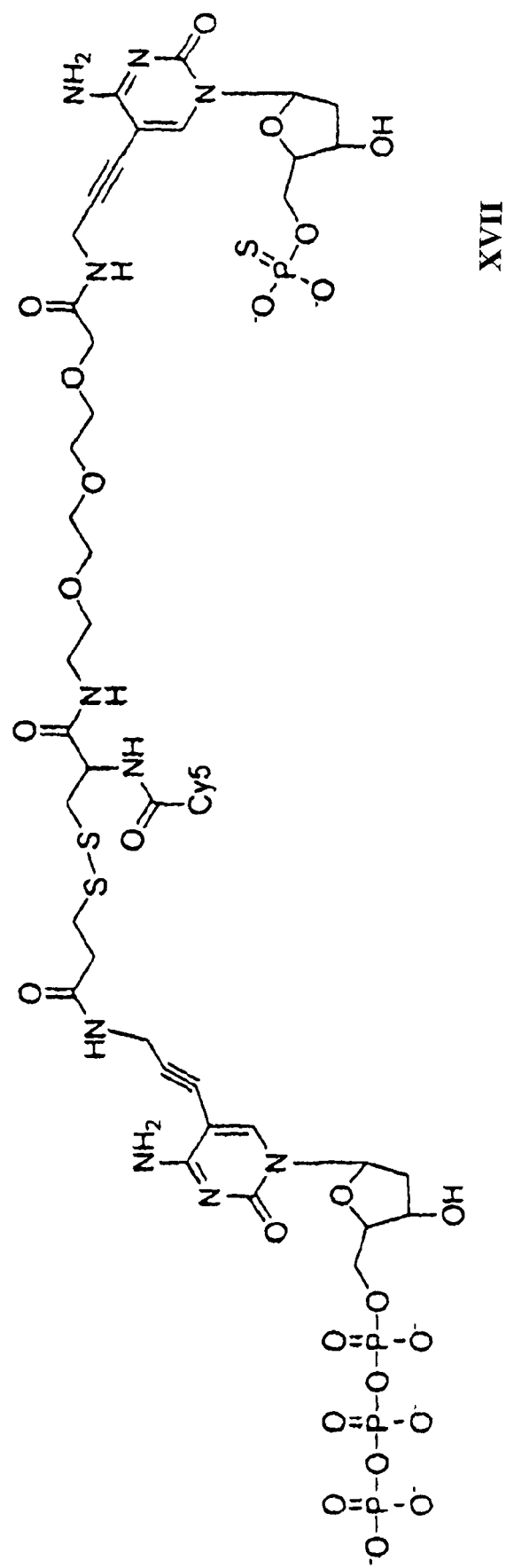
Figure 10C:
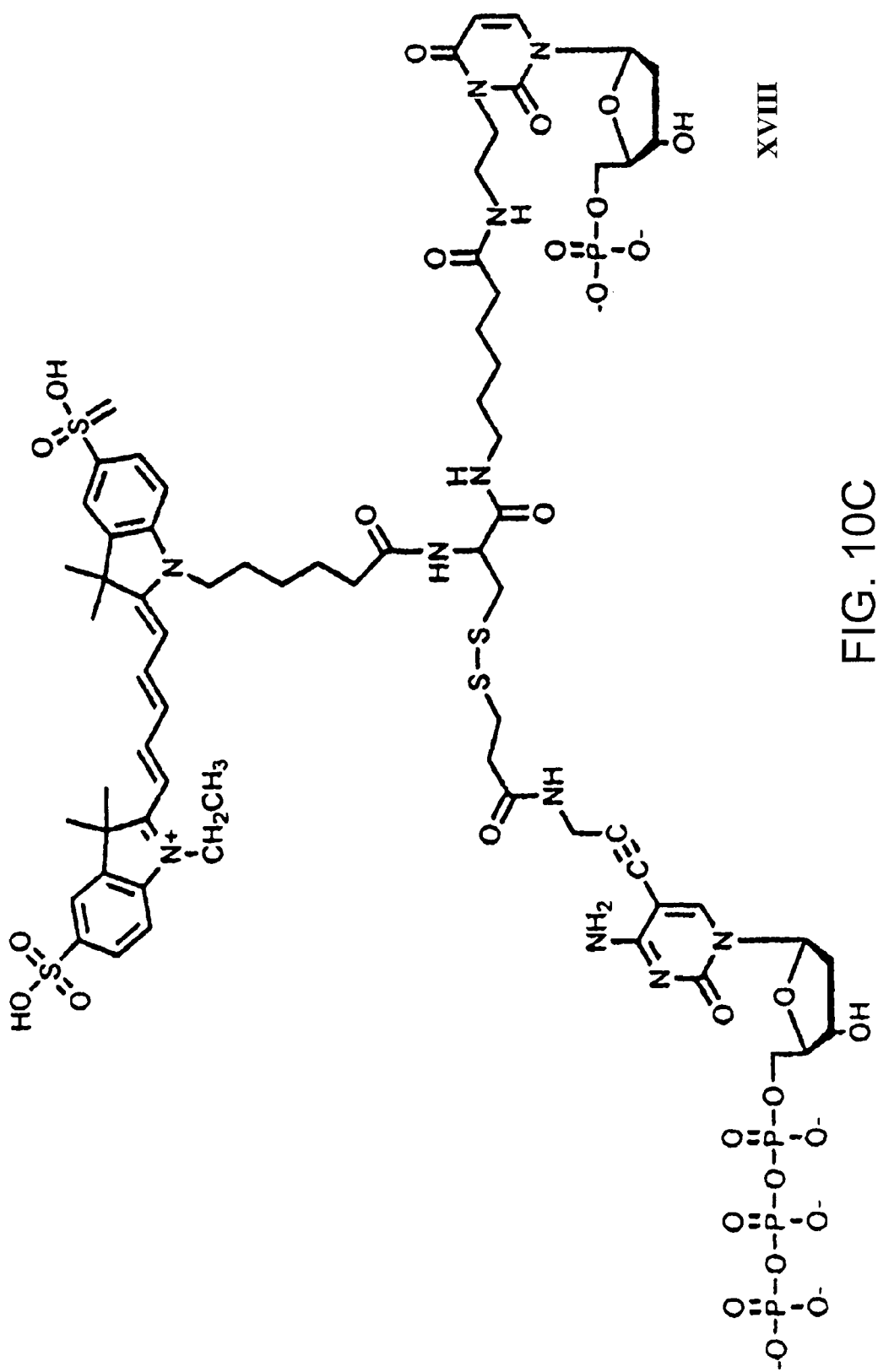
Figure 11A:
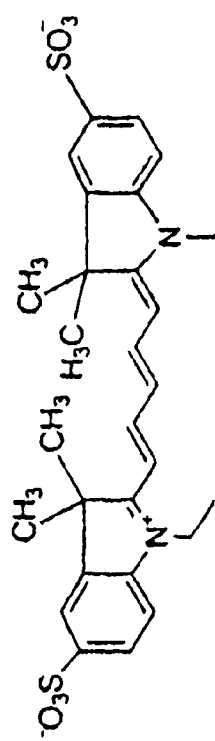
Figure 11A:
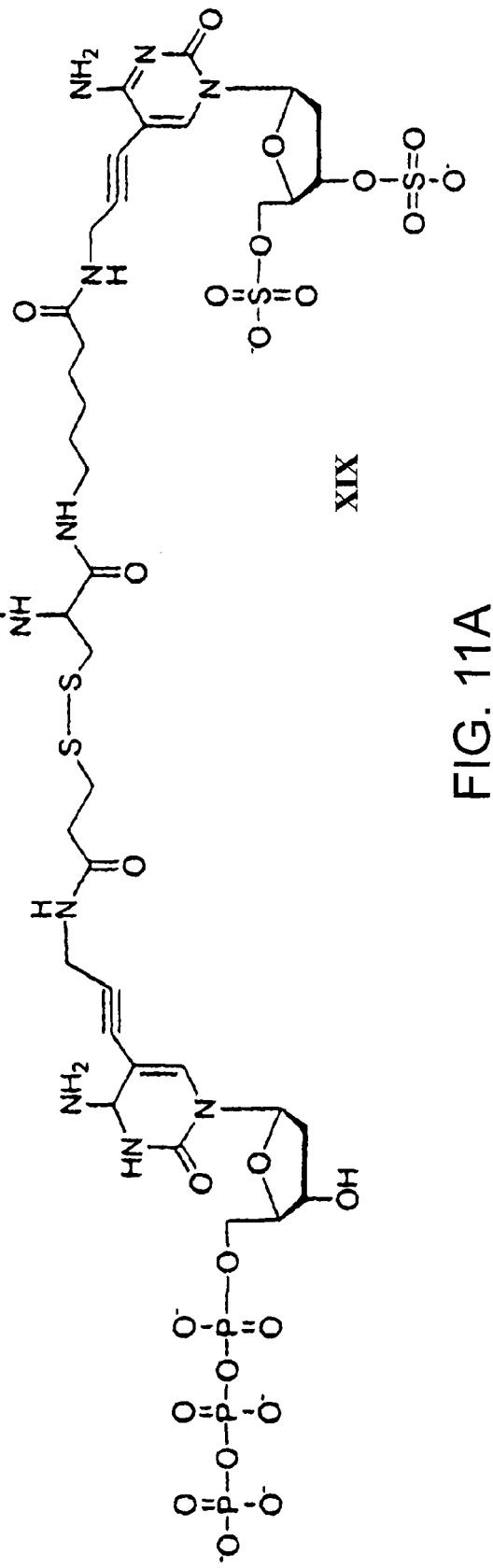
Figure 11B:
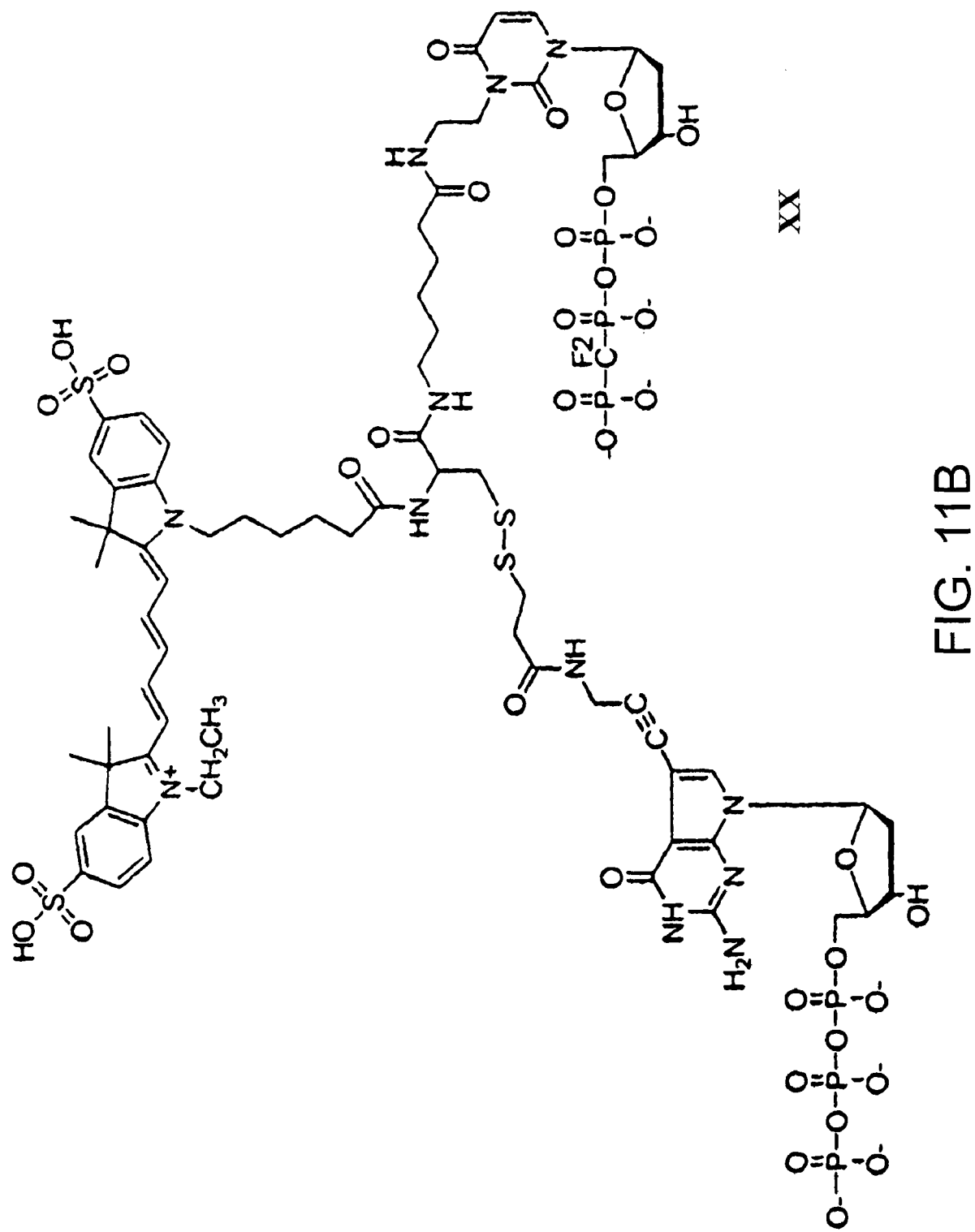
Figure 11C:
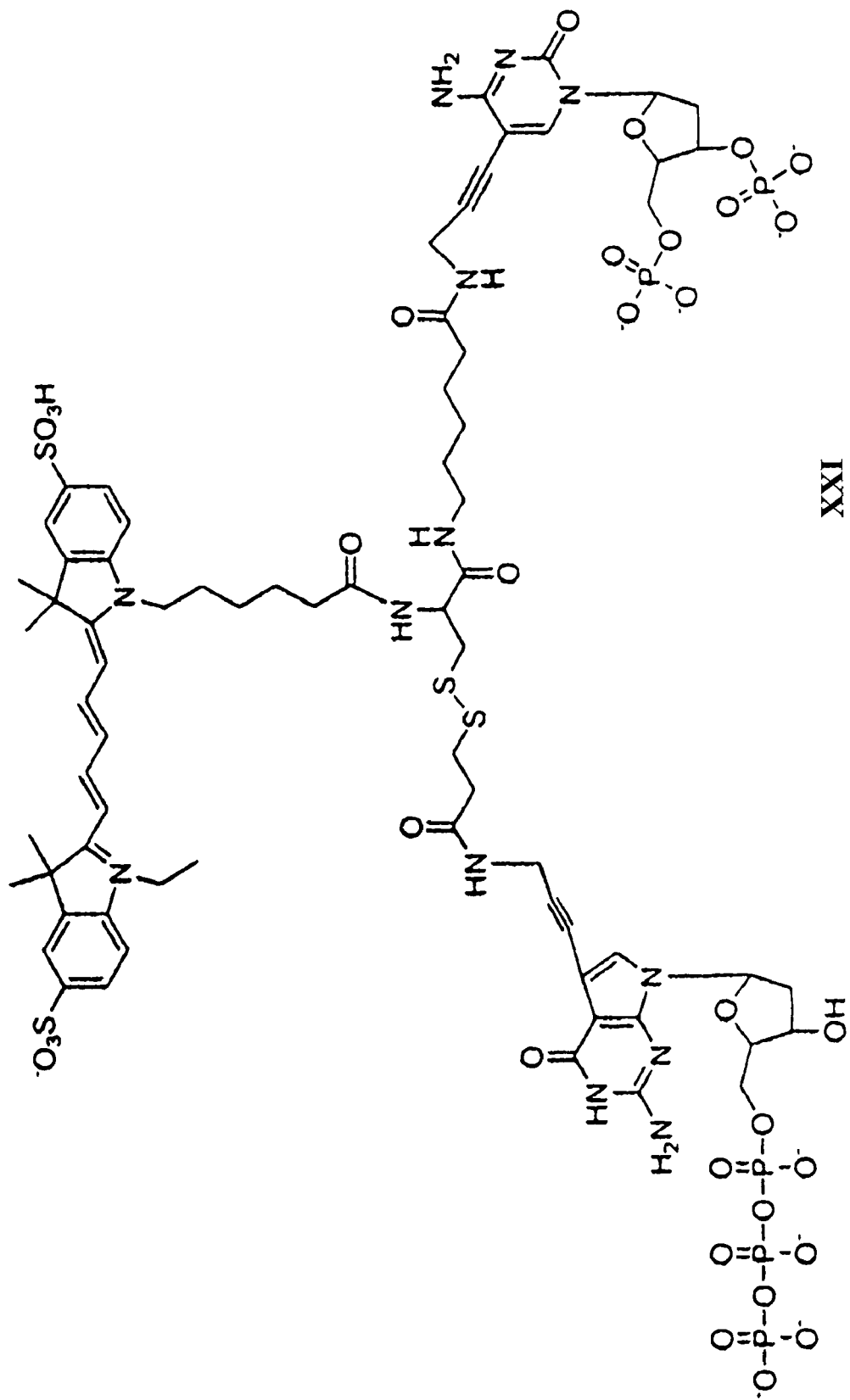
Figure 12A:
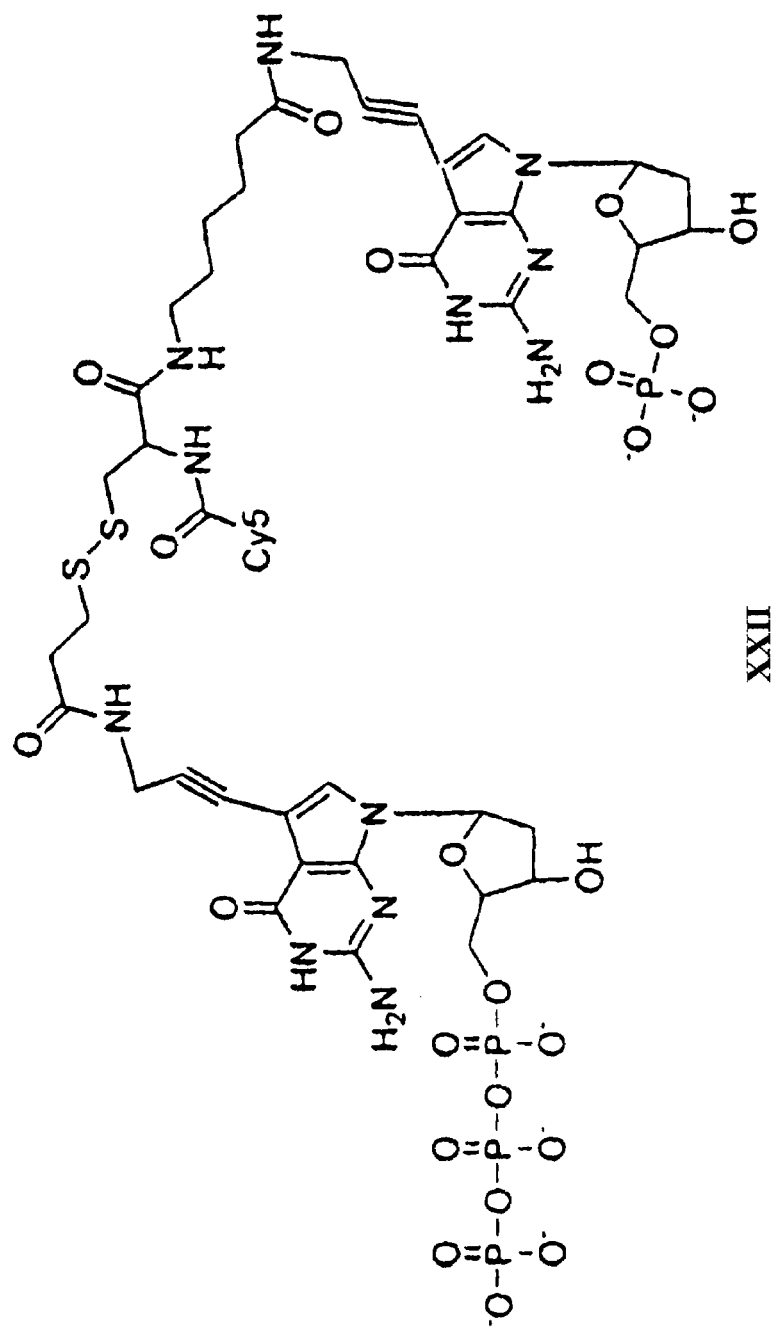
Figure 12B:
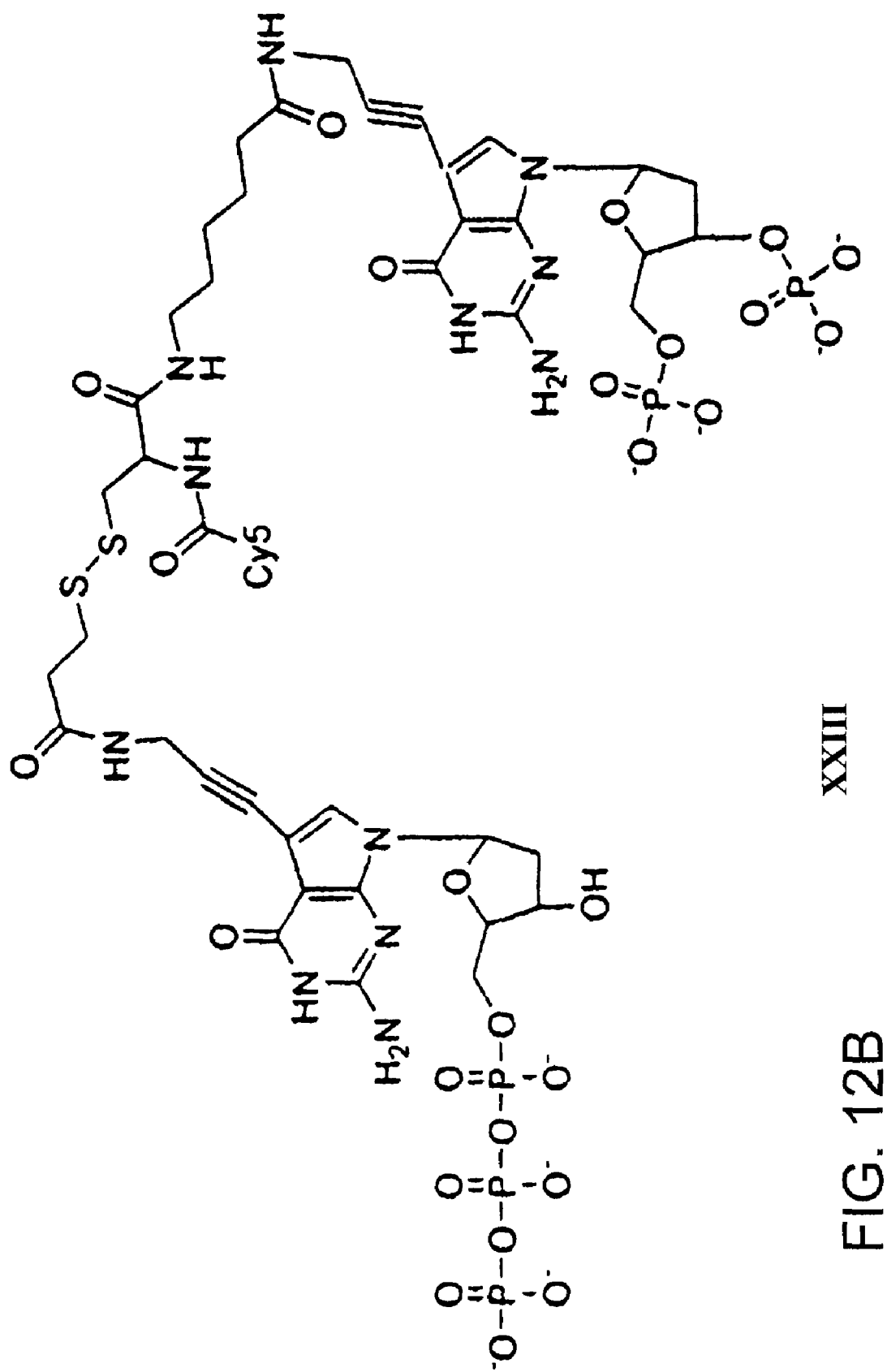
Figure 12C:
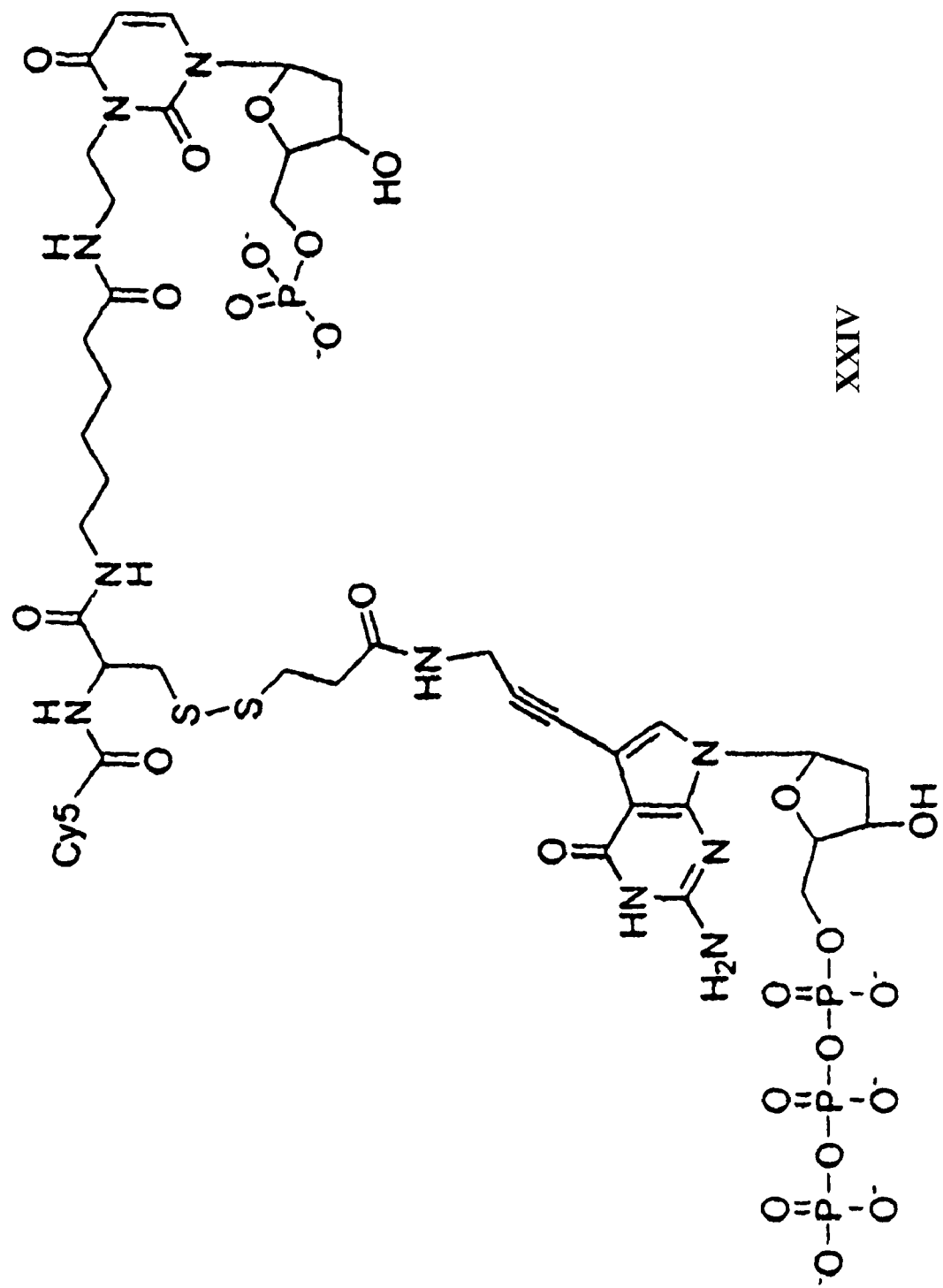
Figure 13:
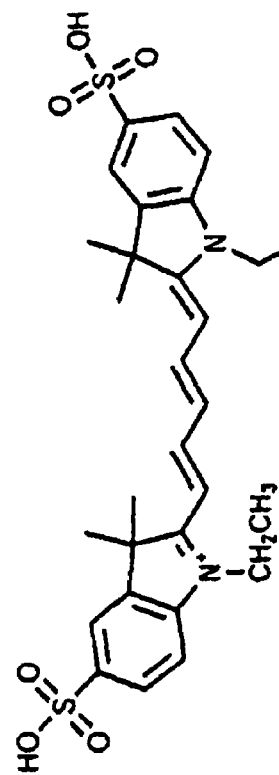
Figure 13A:
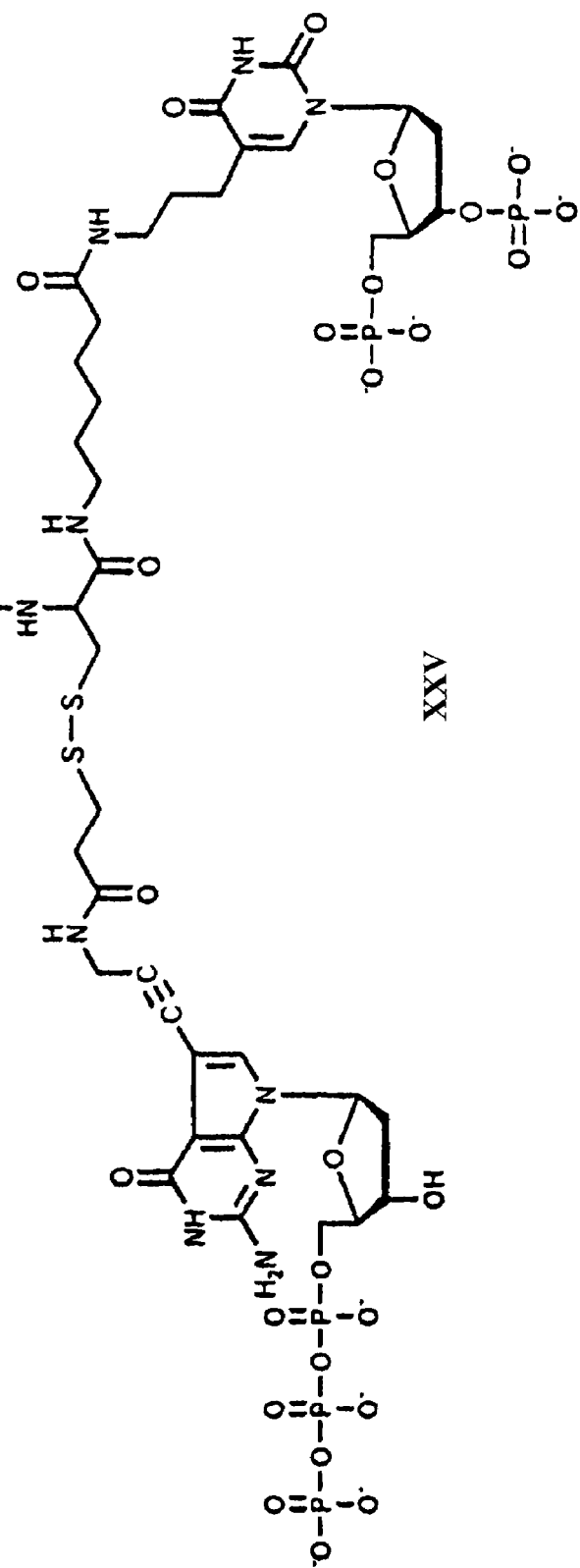
Figure 13B:
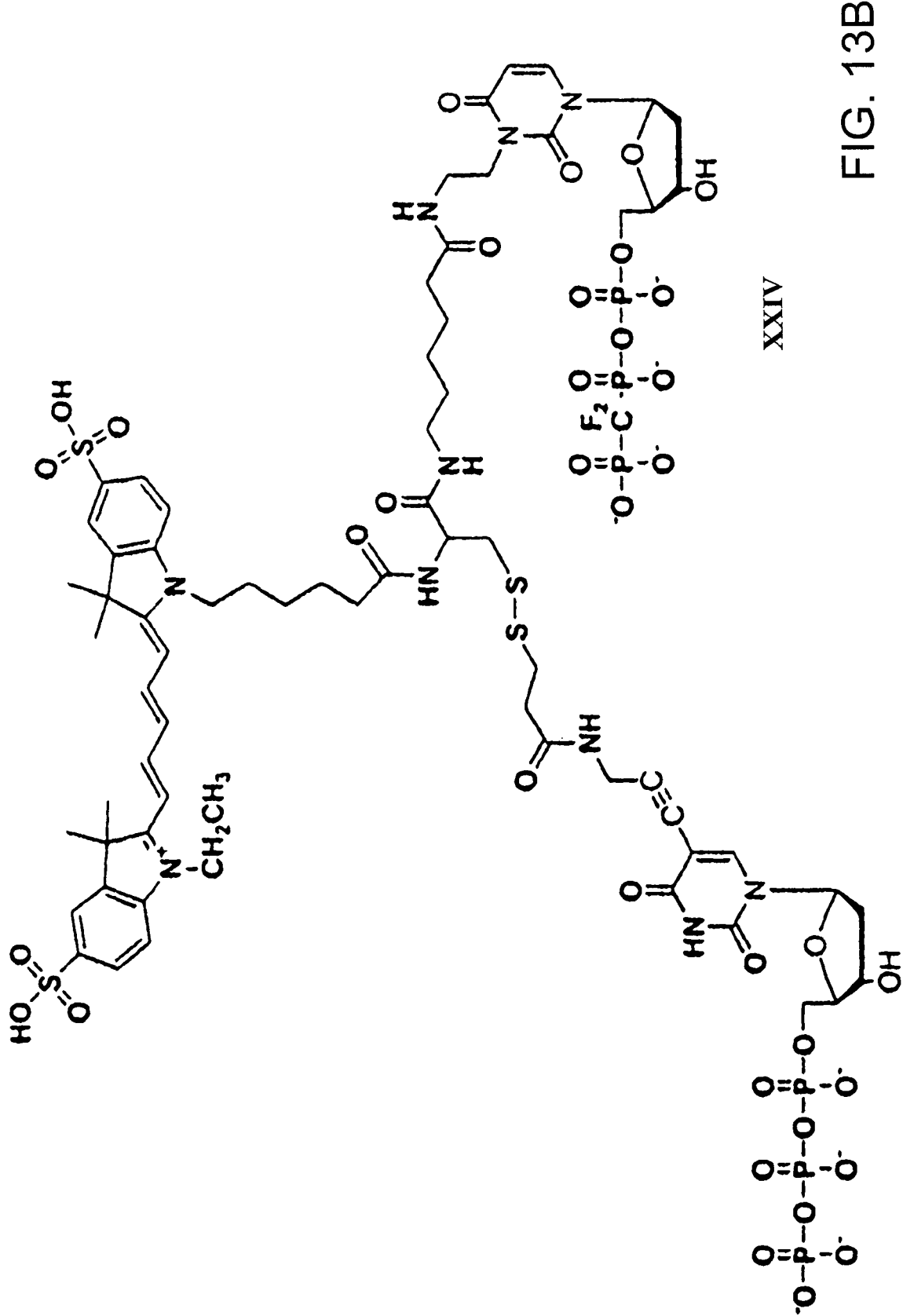
Figure 13C:
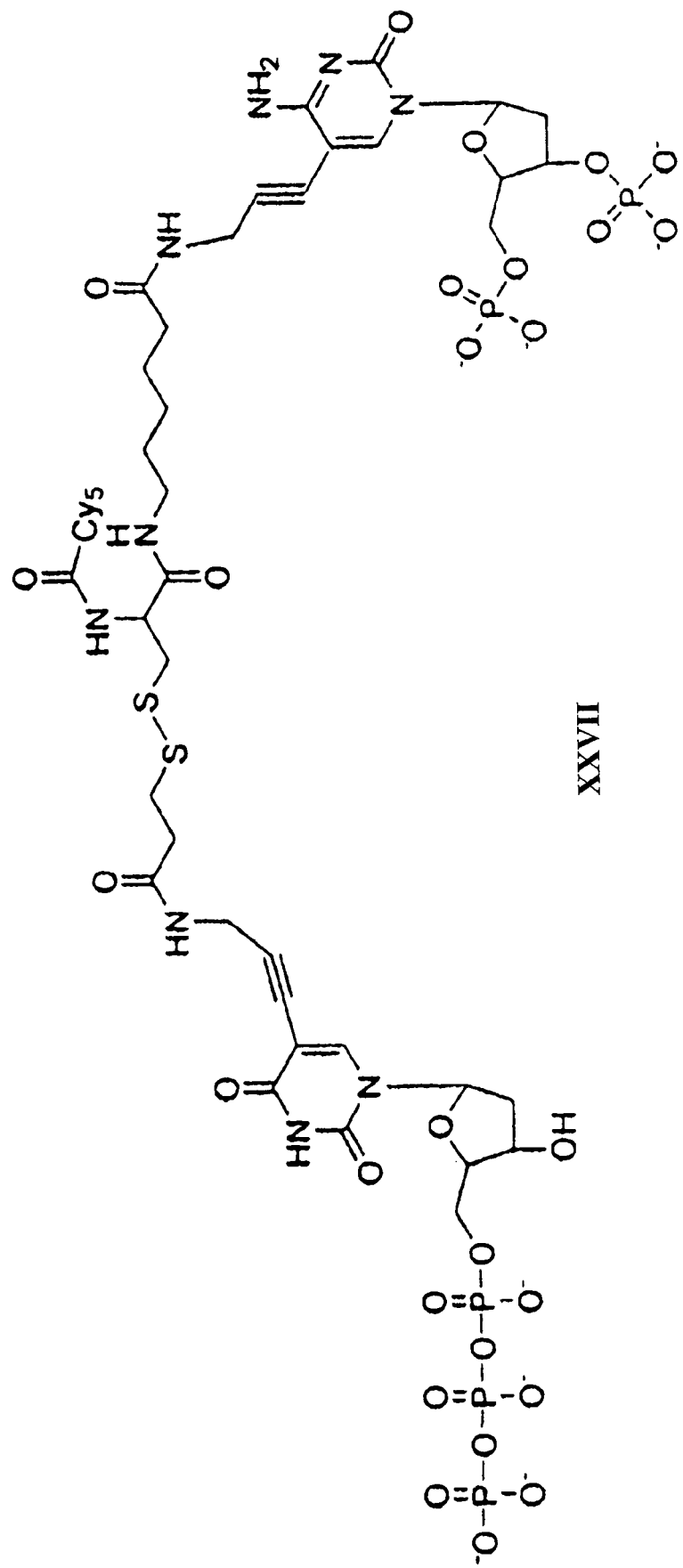
Figure 14A:
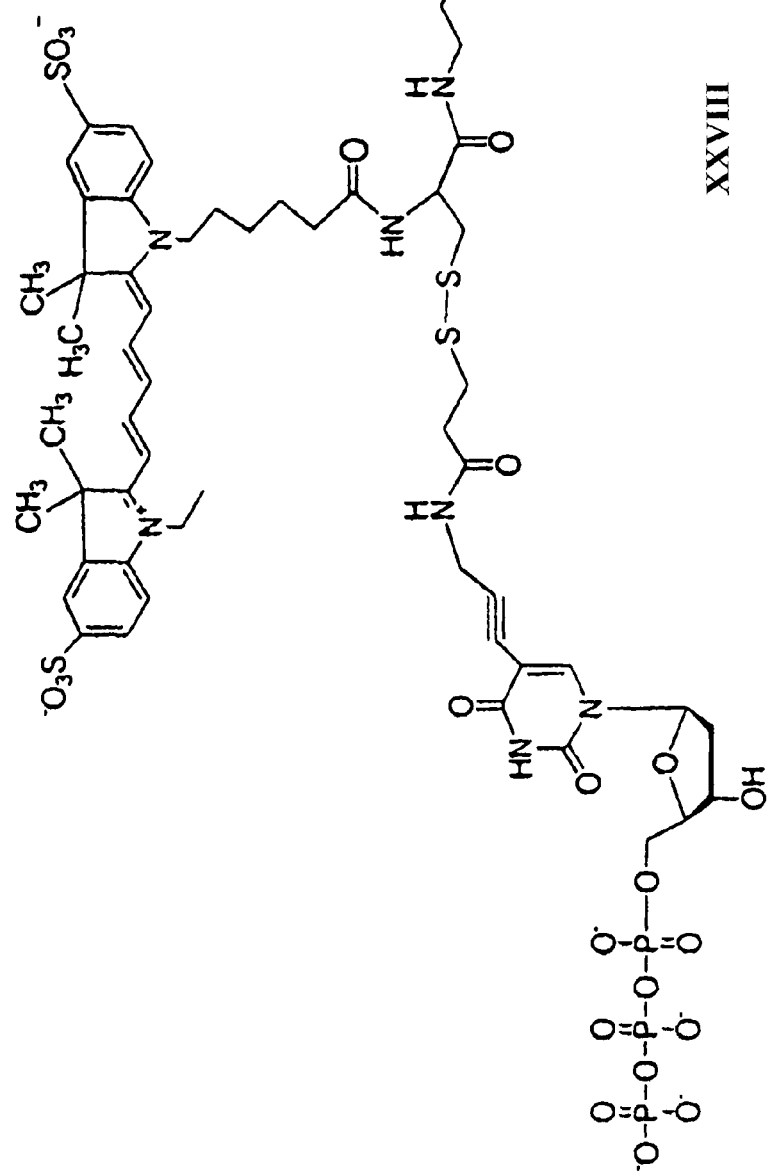
Figure 14B:
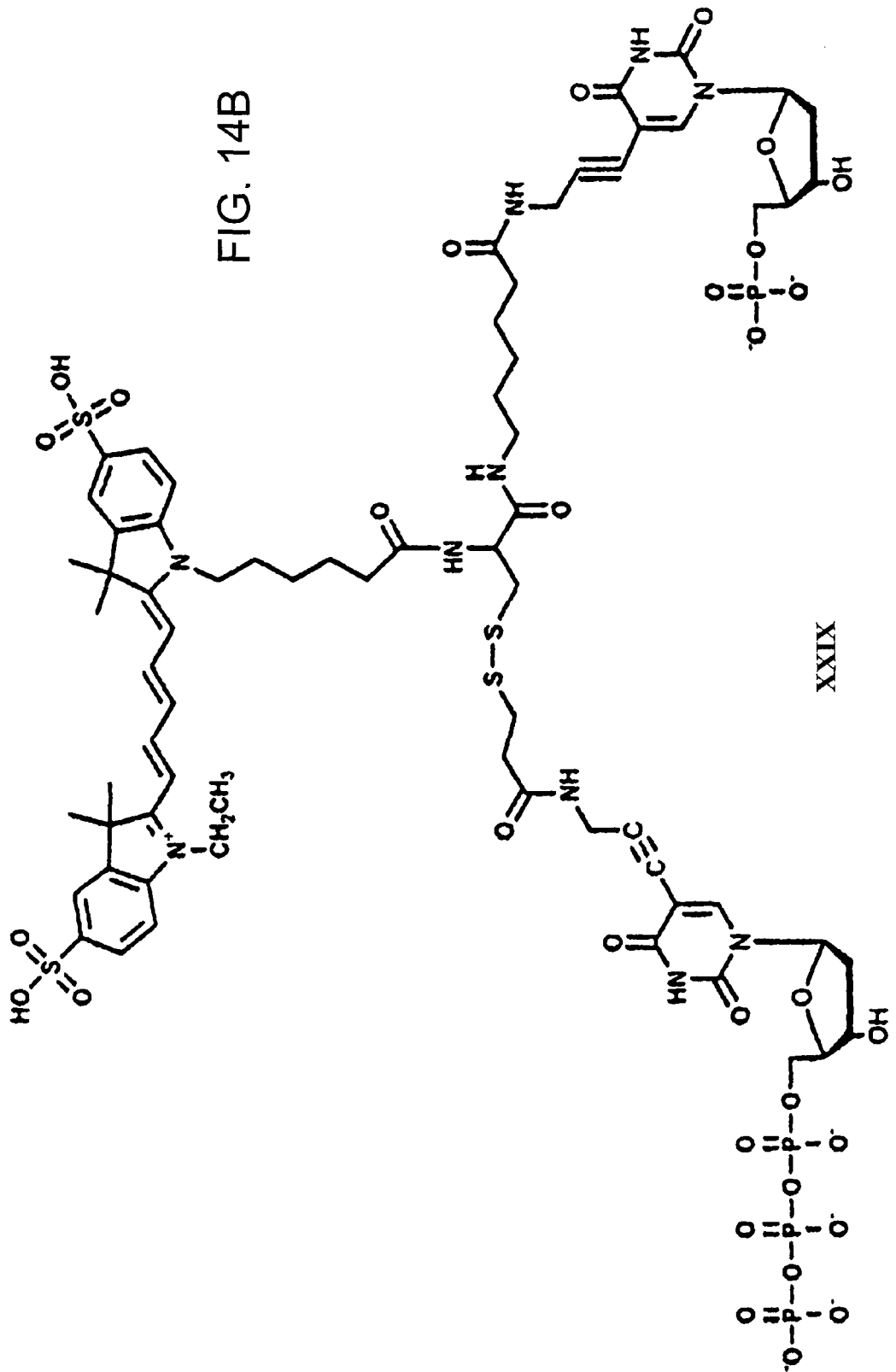
Figure 14C:
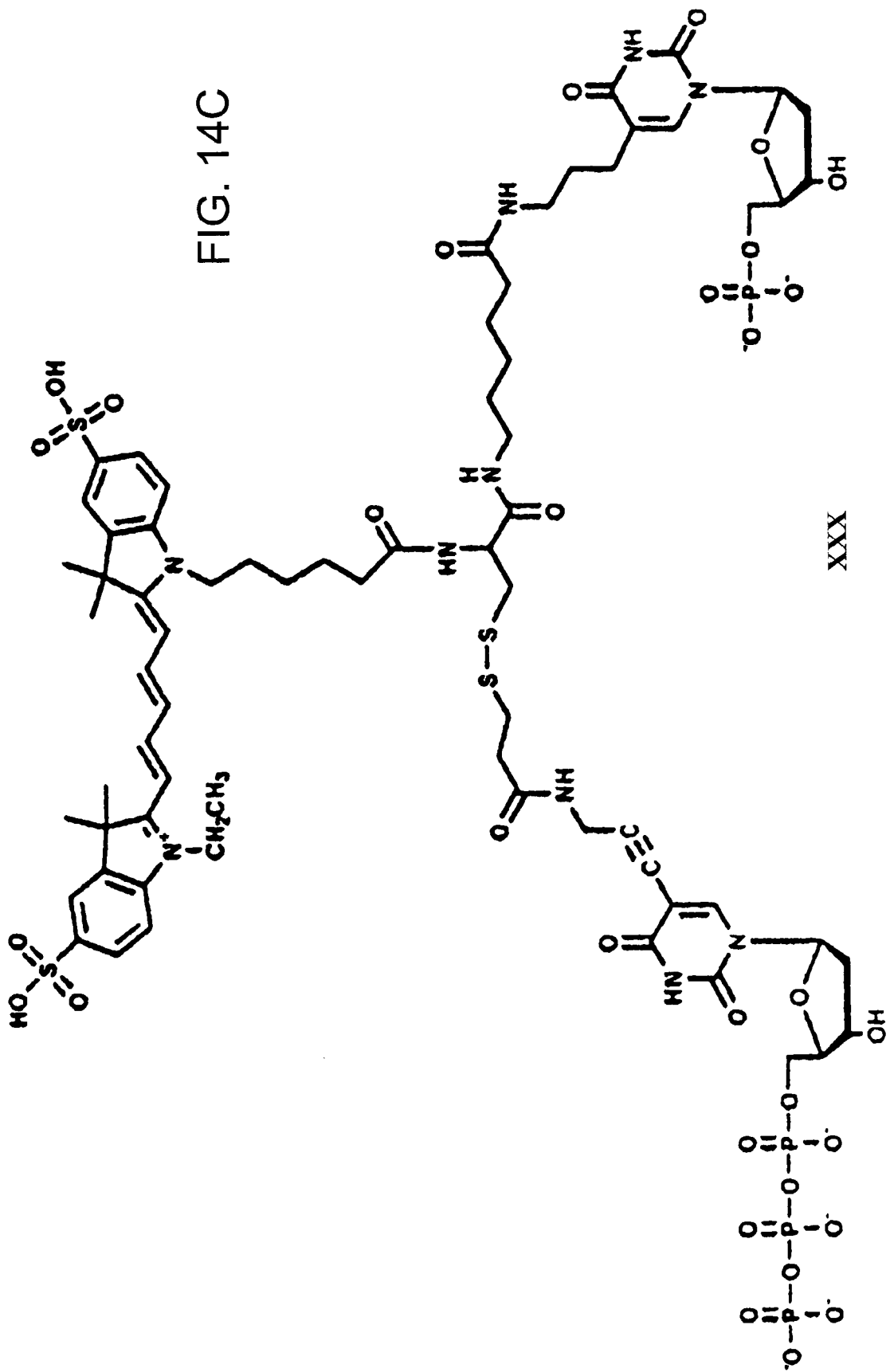
Figure 15A:
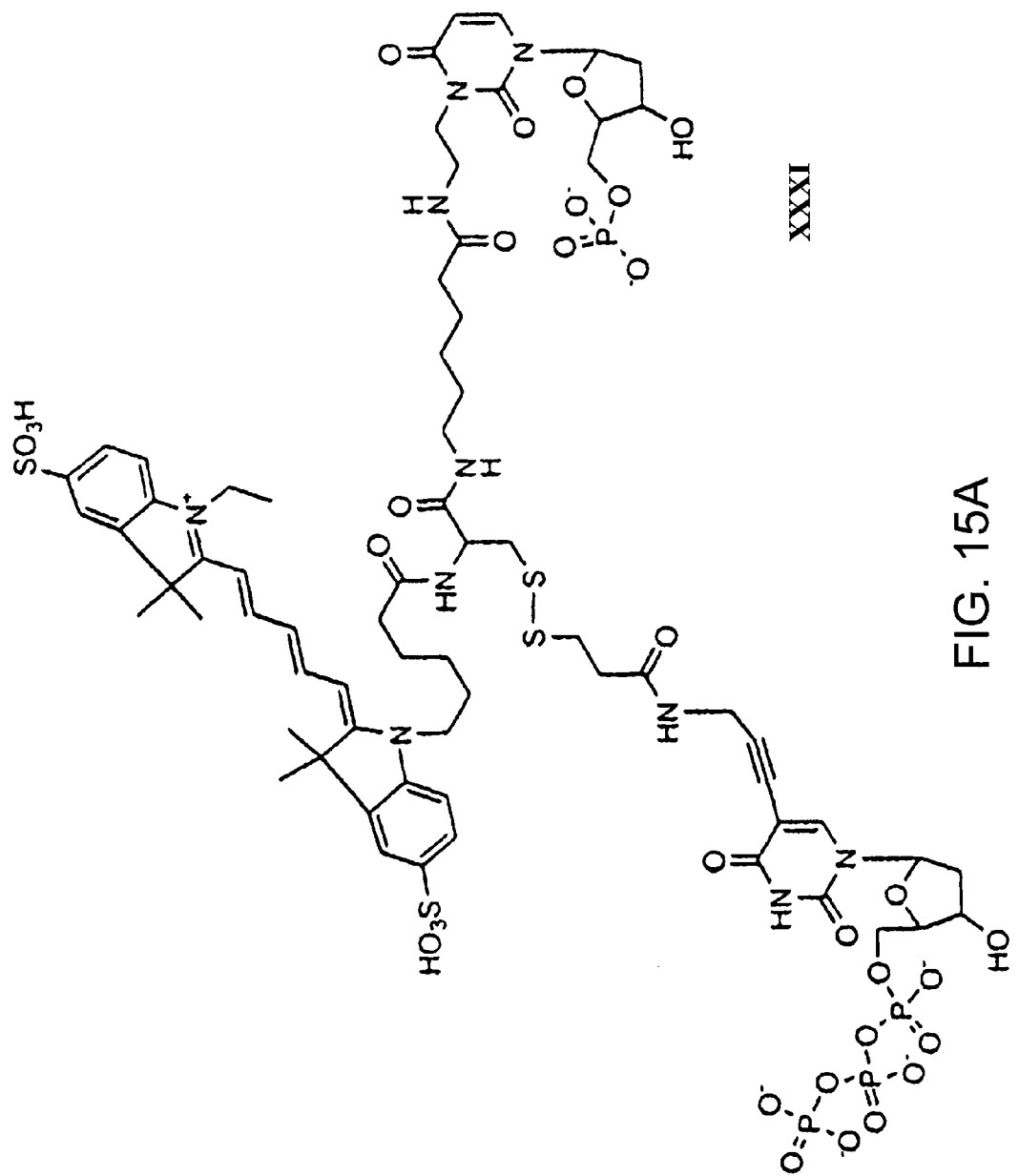
Figure 15B:
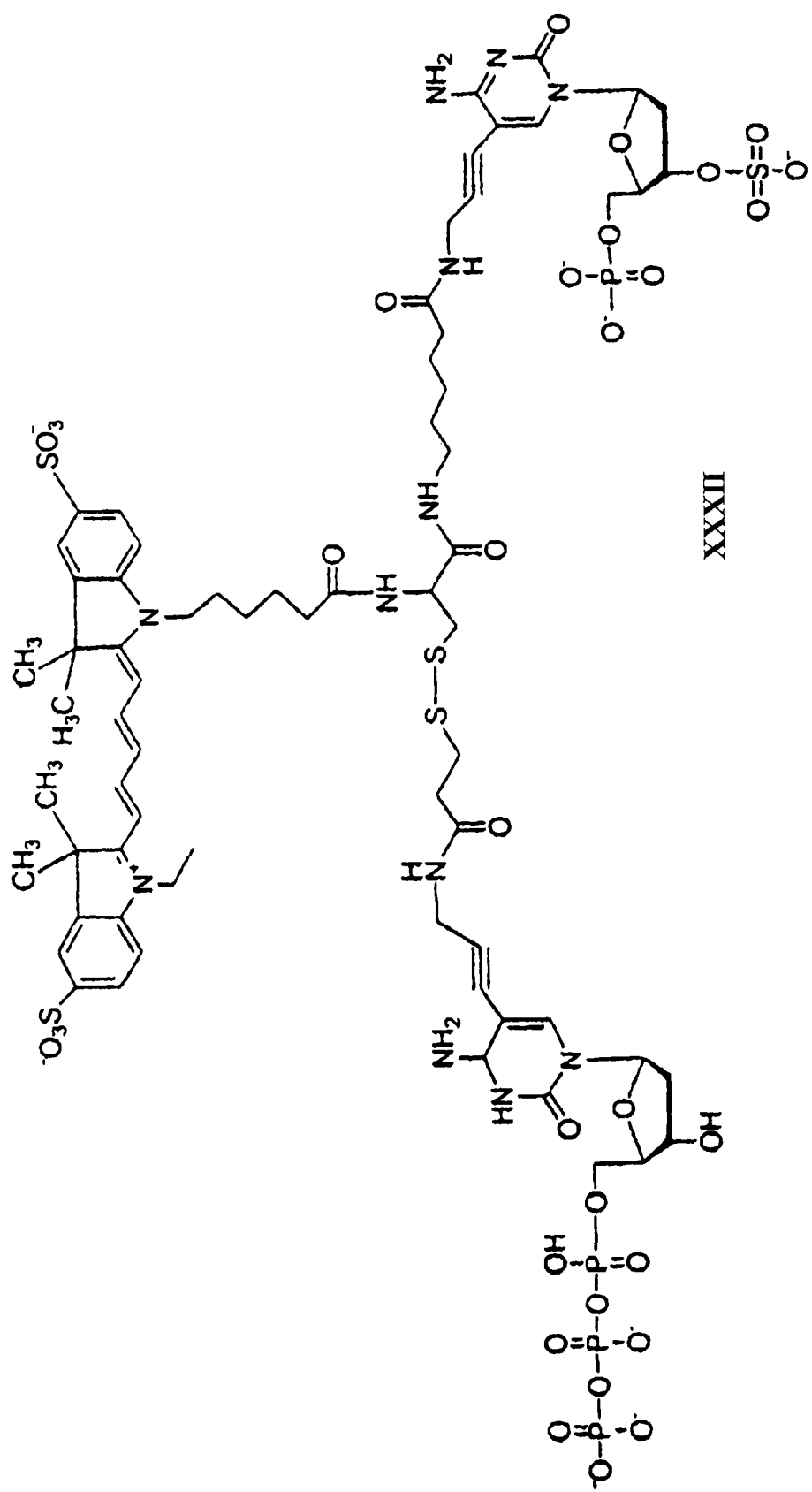
Figure 15C:
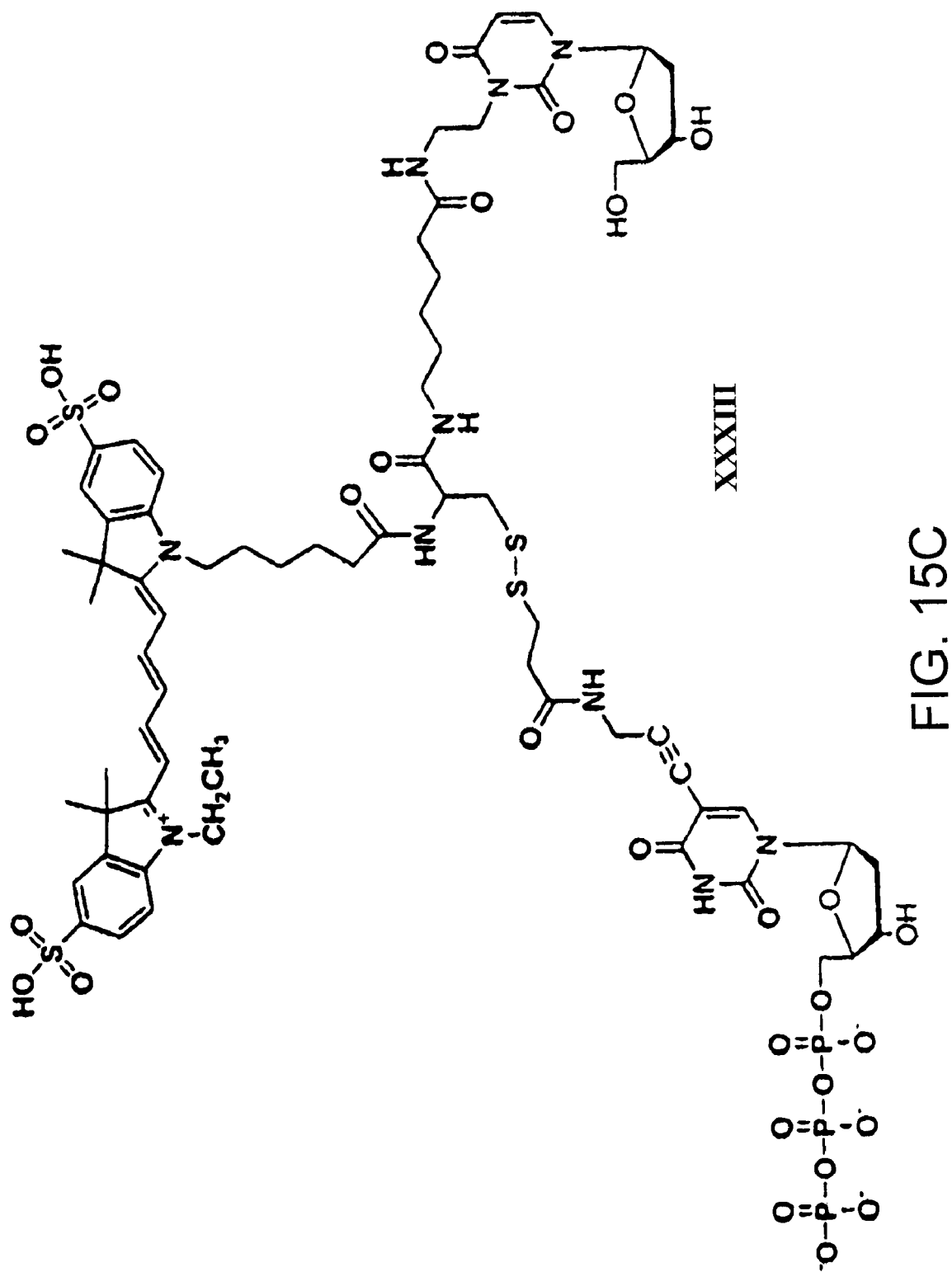
Figure 16A:
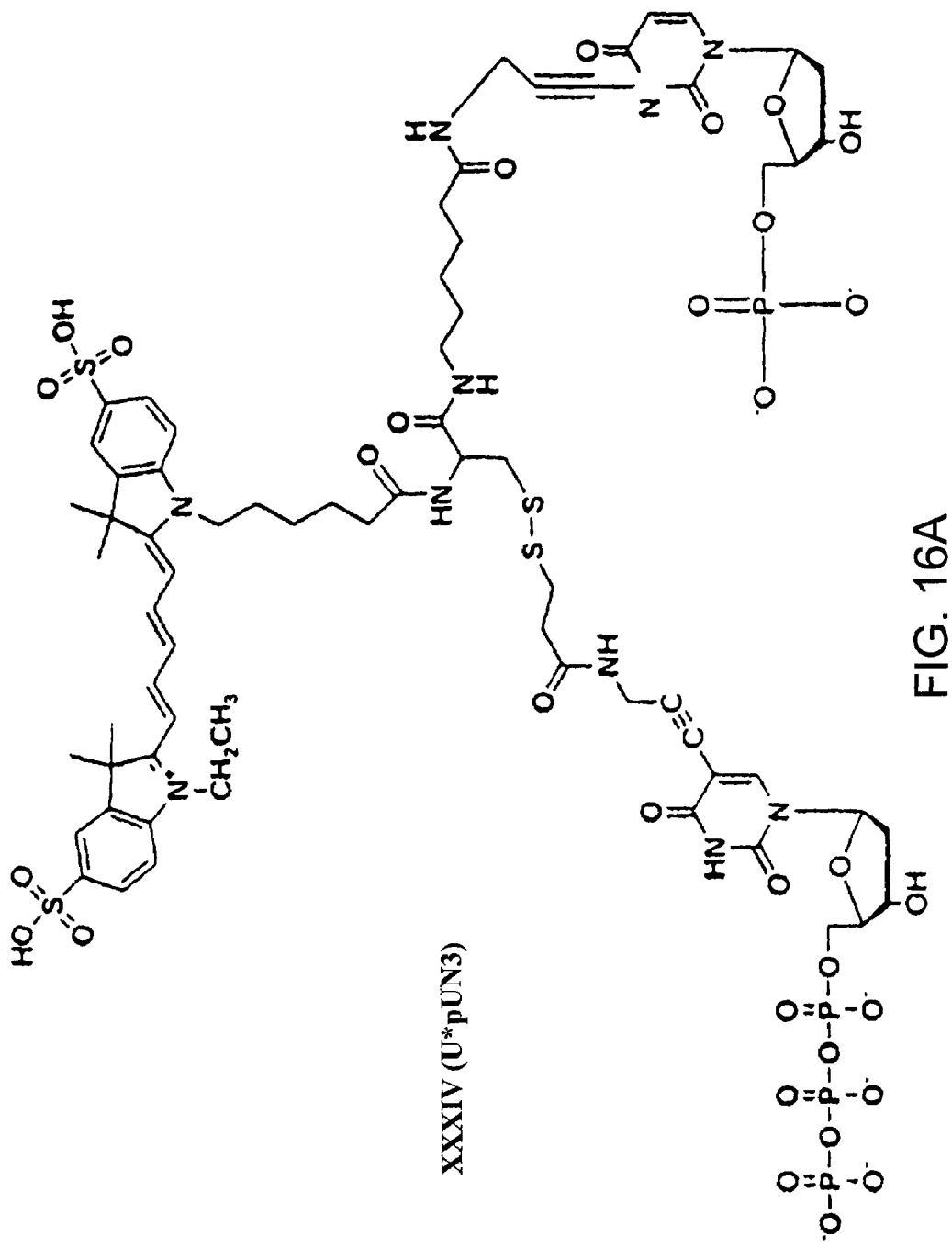
Figure 16C:
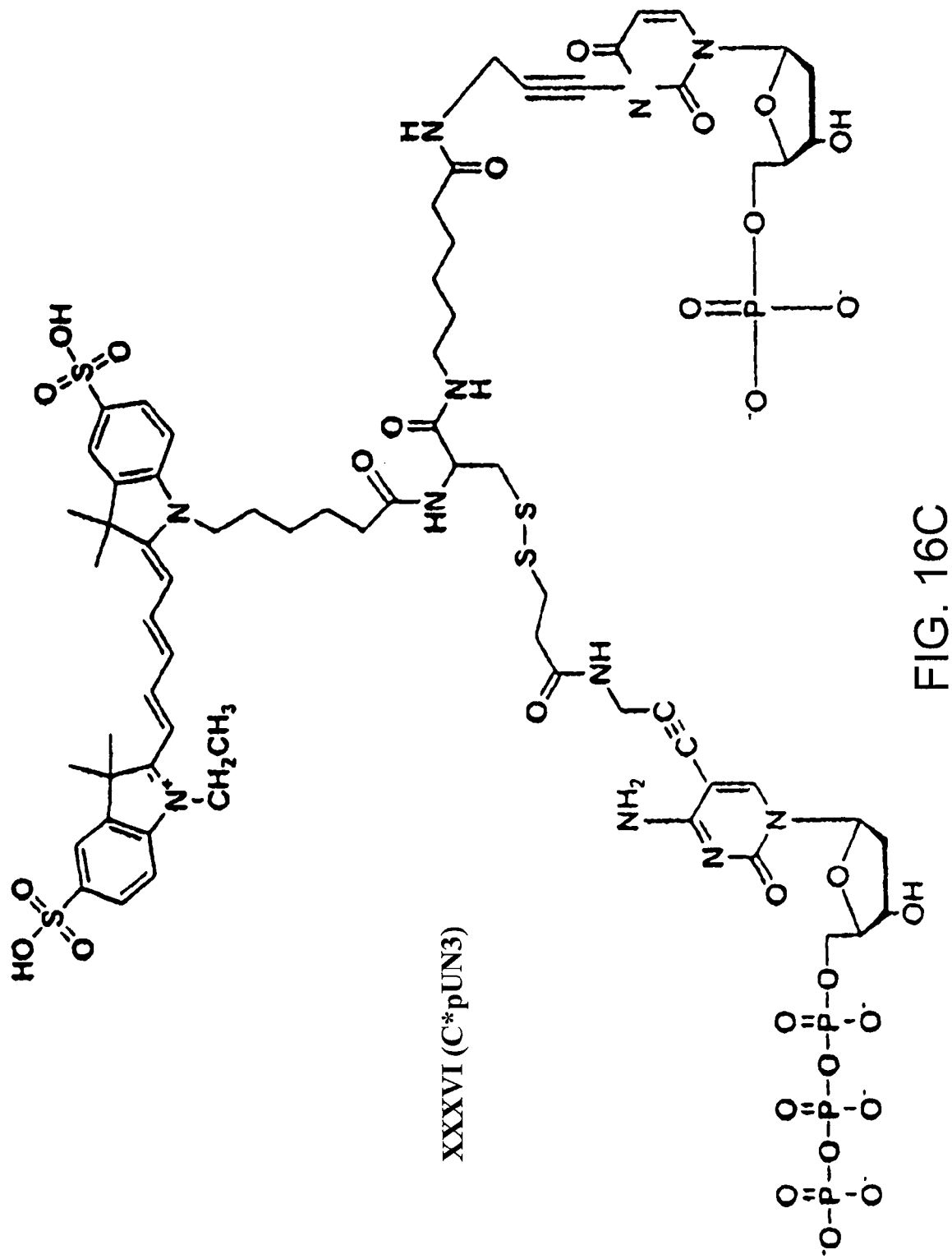
Figure 17B:
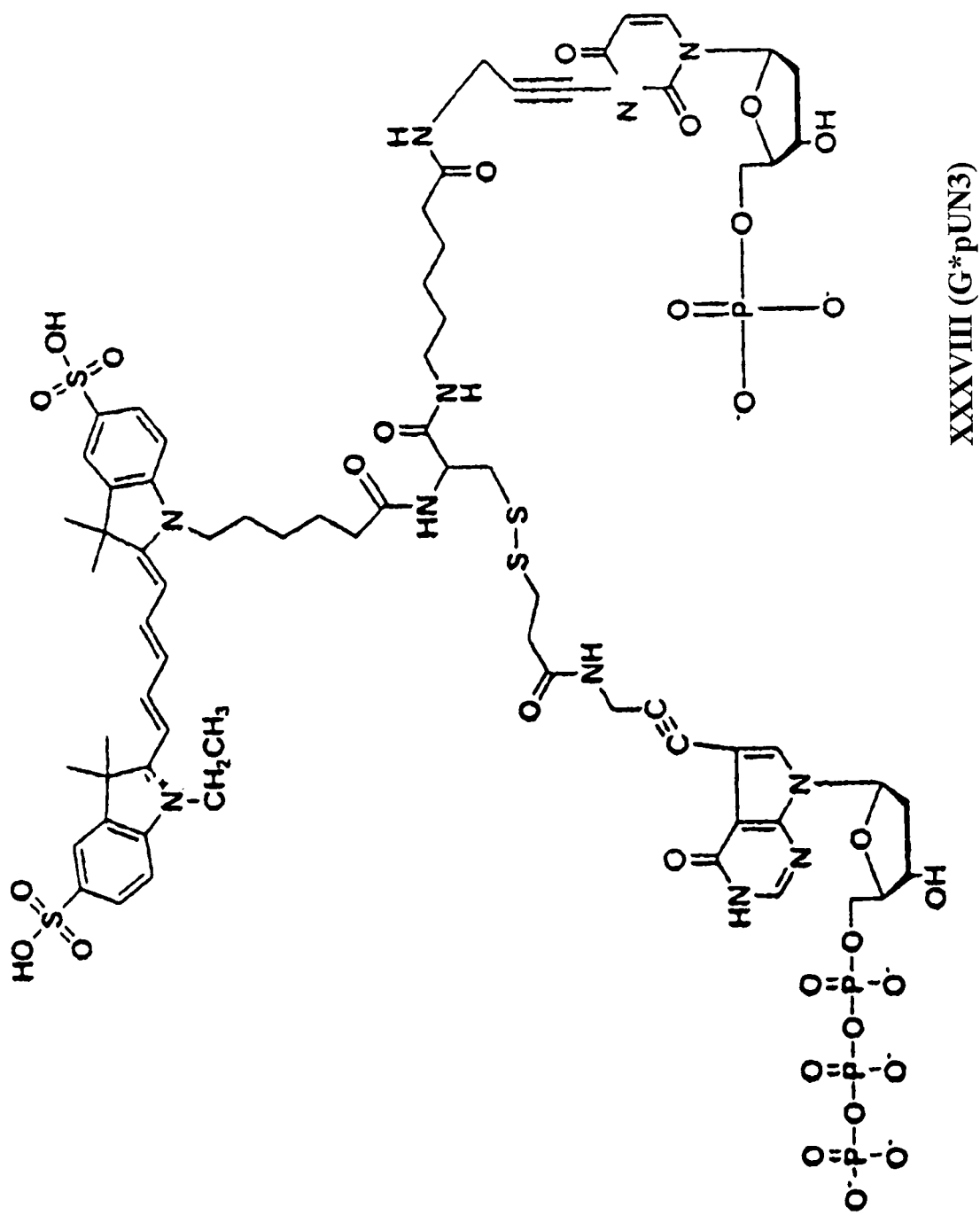
Figure 17C:
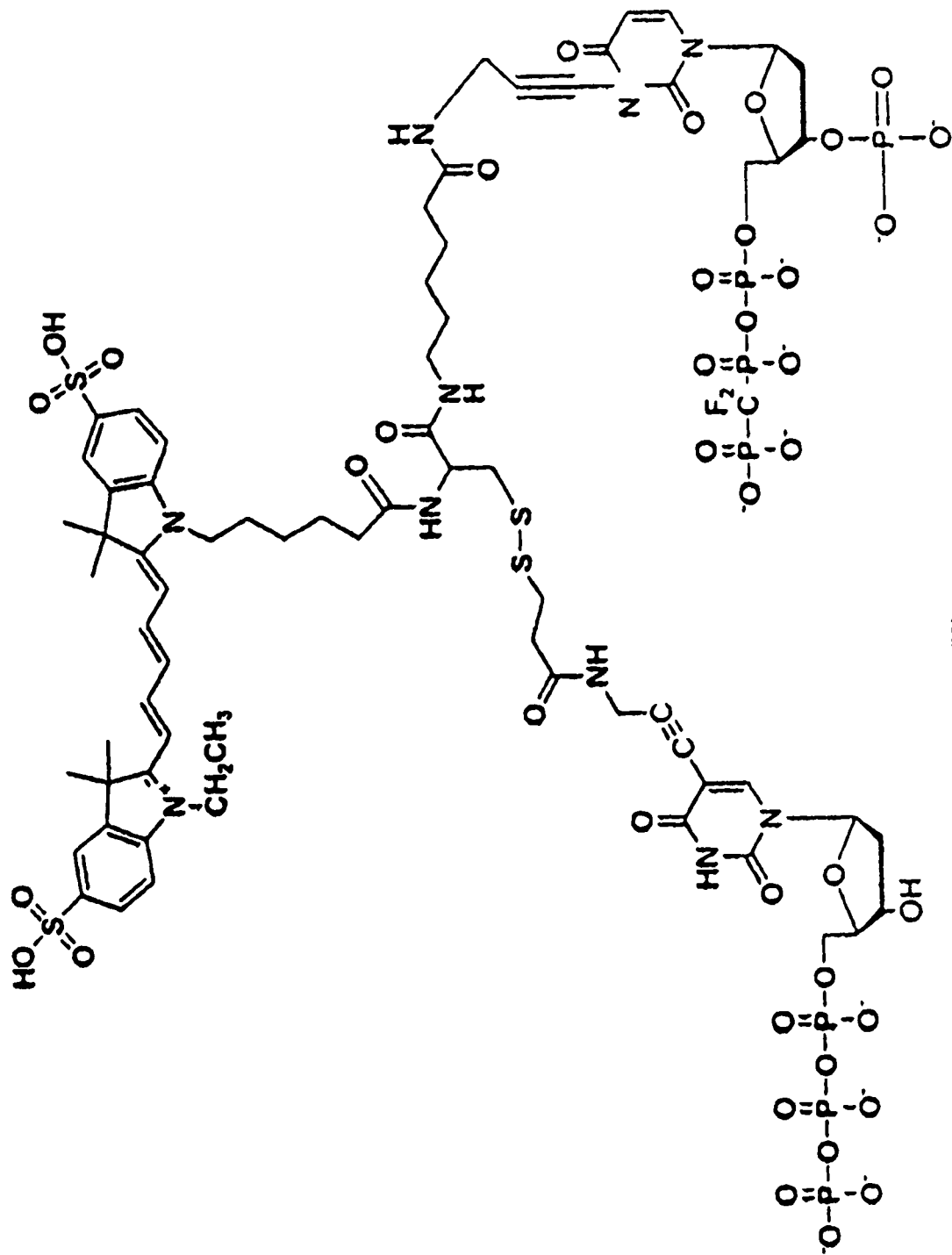
Figure 18A:
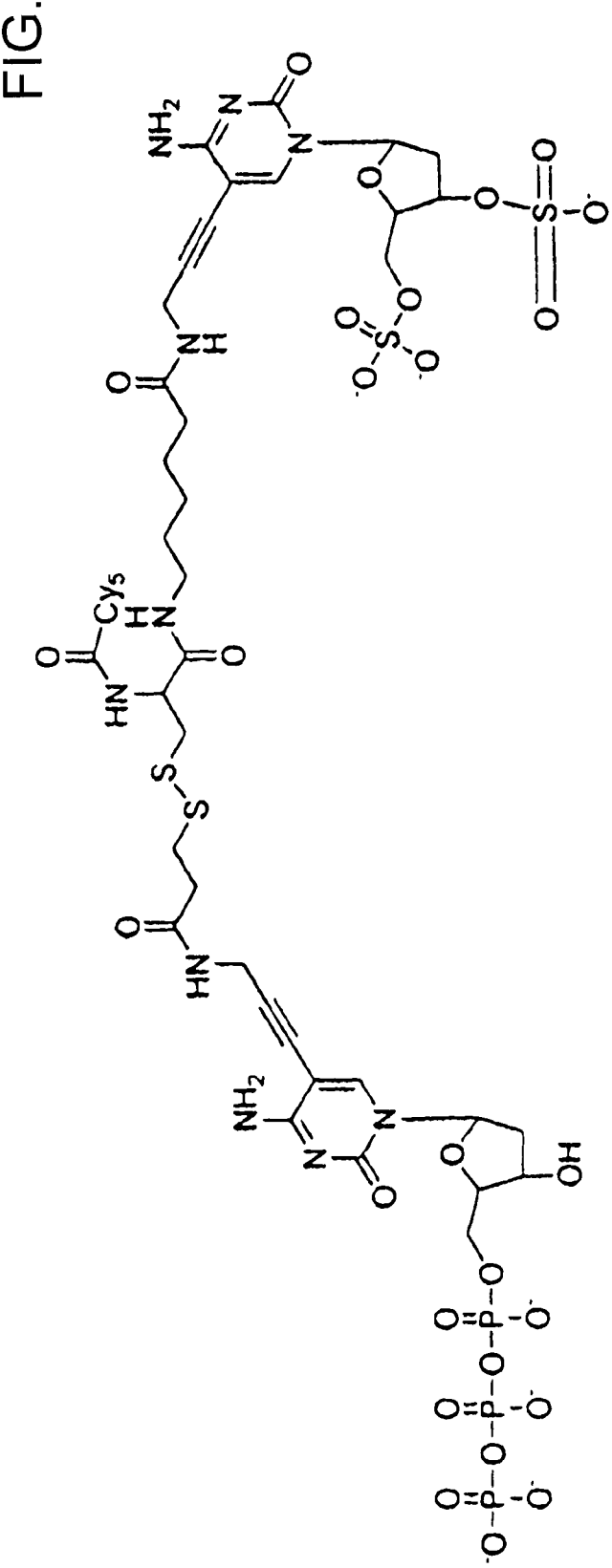
Figure 18B:
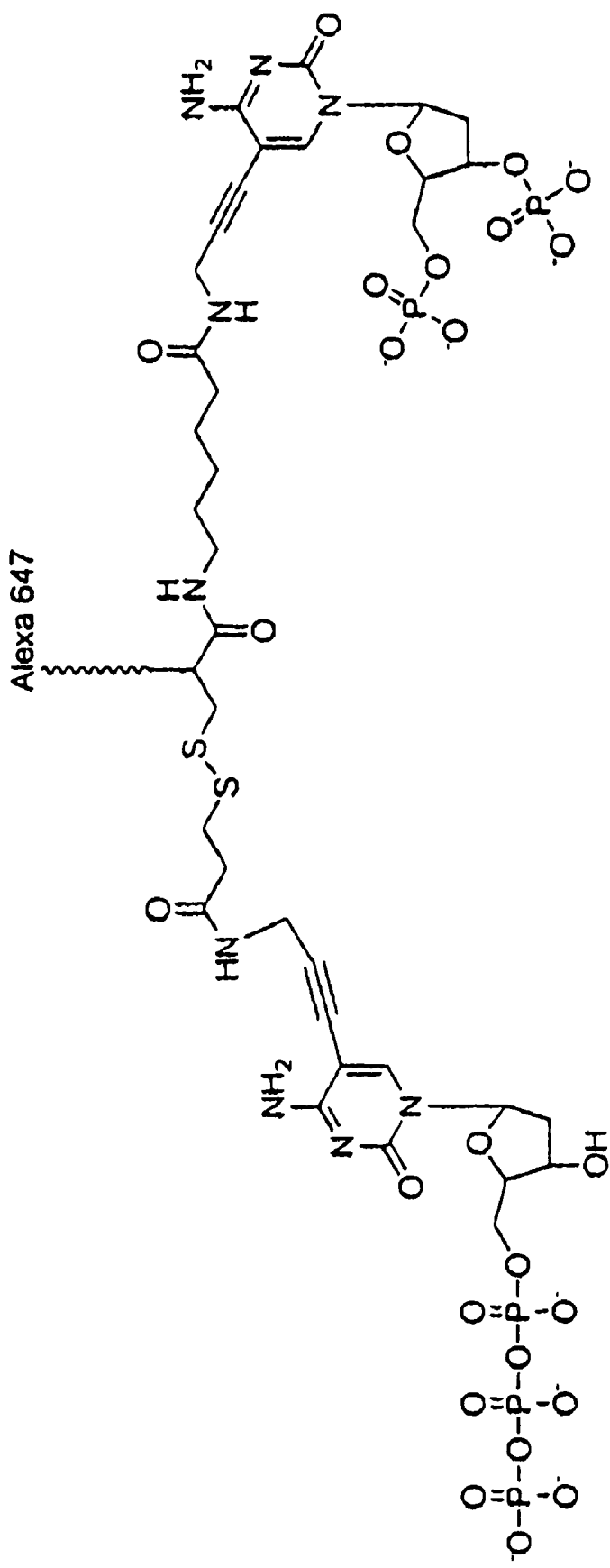

| Nucleotide Analog | Abbreviation |
|---|---|
| Compound II in FIG. 5 | C*pA C2 thiohexyl PEG |
| Compound III in FIG. 5 | A*pA C8 amido PEG5 |
| Compound IV in FIG. 6 | A*pAp C7 Parg3 |
| Compound V in FIG. 6 | A*psA C8 amido PEG5 |
| Compound VI in FIG. 6 | A*psC C5 PEG3 Parg |
| Compound VII in FIG. 7 | A*pA C6 amido PEG5 |
| Compound VIII in FIG. 7 | A*pA C8 amido PEG3 |
| Compound IX in FIG. 7 | A*pAp C5 Parg |
| Compound X in FIG. 8 | A*pCF2pp U N3 |
| Compound XI in FIG. 8 | A*pCp C5 Parg |
| Compound XII in FIG. 8 | A*psA C8 amido PEG3 |
| Compound XIII in FIG. 9 | A*pU N3 Pro |
| Compound XIV in FIG. 9 | A*pUp C5 Pro |
| Compound XV in FIG. 9 | C*pC C5 Parg |
| Compound XVI in FIG. 10 | C*pCp C5 Parg |
| Compound XVII in FIG. 10 | C*psC C5 PEG3 Parg |
| Compound XVIII in FIG. 10 | C*pU N3 Pro |
| Compound XIX in FIG. 11 | C*sCs C7 Parg |
| Compound XX in FIG. 11 | G*pCF2pp U N3 |
| Compound XXI in FIG. 11 | G*pCp C5 Parg |
| Compound XXII in FIG. 12 | G*pG C7 Parg |
| Compound XXIII in FIG. 12 | G*pGp C7 Parg |
| Compound XXIV in FIG. 12 | G*pU N3 Pro |
| Compound XXV in FIG. 13 | G*pUp C5 Pro |
| Compound XXVI in FIG. 13 | U*pCF2ppU N3 Pro |
| Compound XXVII in FIG. 13 | U*pCp C5 Parg |
| Compound XXVIII in FIG. 14 | U*pU C5 A1 |
| Compound XXIX in FIG. 14 | U*pU C5 Parg |
| Compound XXX in FIG. 14 | U*pU C5 Pro |
| Compound XXXI in FIG. 15 | U*pU N3 Pro |
| Compound XXXII in FIG. 15 | U*So 3Cp C5 Parg |
| Compound XXXIII in FIG. 15 | U U N3 Pro |
| Compound XXXIV in FIG. 16 | U*pUN3 |
| Compound XXXV in FIG. 16 | U*UN3 |
| Compound XXXVI in FIG. 16 | C*pUN3 |
| Compound XXXVII in FIG. 17 | A*pUN3 |
| Compound XXXVIII in FIG. 17 | G*pUN3 |
| Compound XXXIX in FIG. 17 | U*pCF2ppU N3 |
| Compound XL in FIG. 18 | C*sCsC5Parg |
| Compound XLI in FIG. 18 | C*pCpC5Parg Alexa 647 |

The following provides exemplary synthesis pathways used to create exemplary compounds of the invention. This is not intended to be limiting, but rather is exemplary of the breadth of analogs that fall within the broad scope of the invention.

Below is an exemplary analog of the invention and its method of synthesis. The product has the following structure:

The foregoing compound is made by a synthetic process that starts with phosphorylation of the following compound to yield the triphosphate:

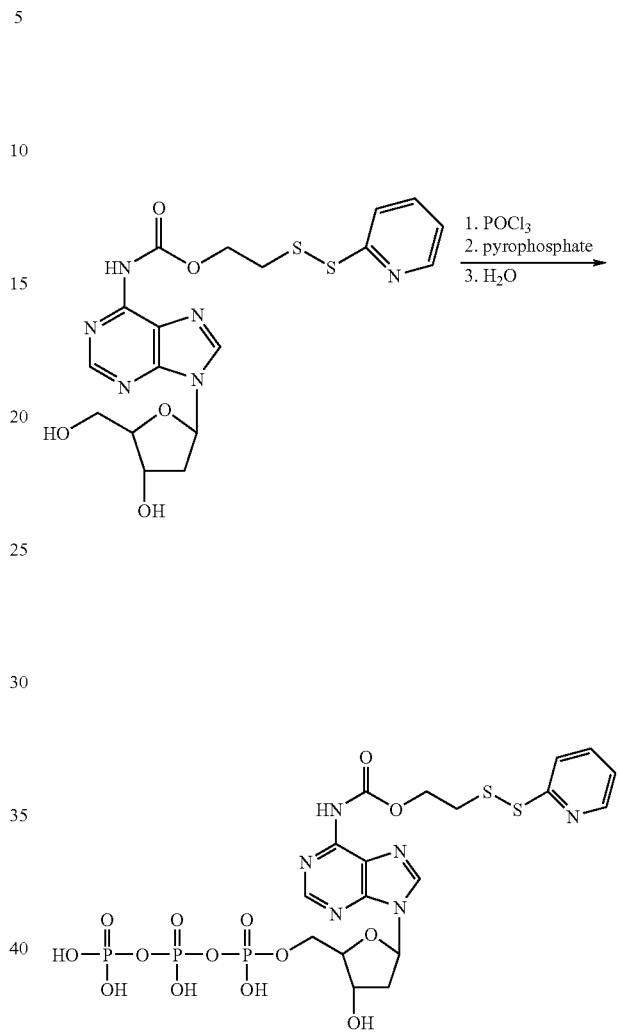

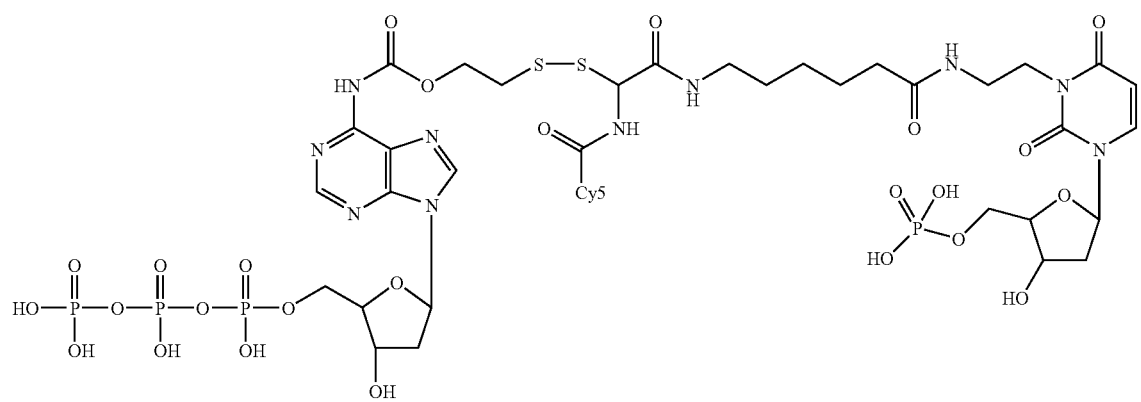

Then a displacement reaction is conducted as follows to yield the final product:
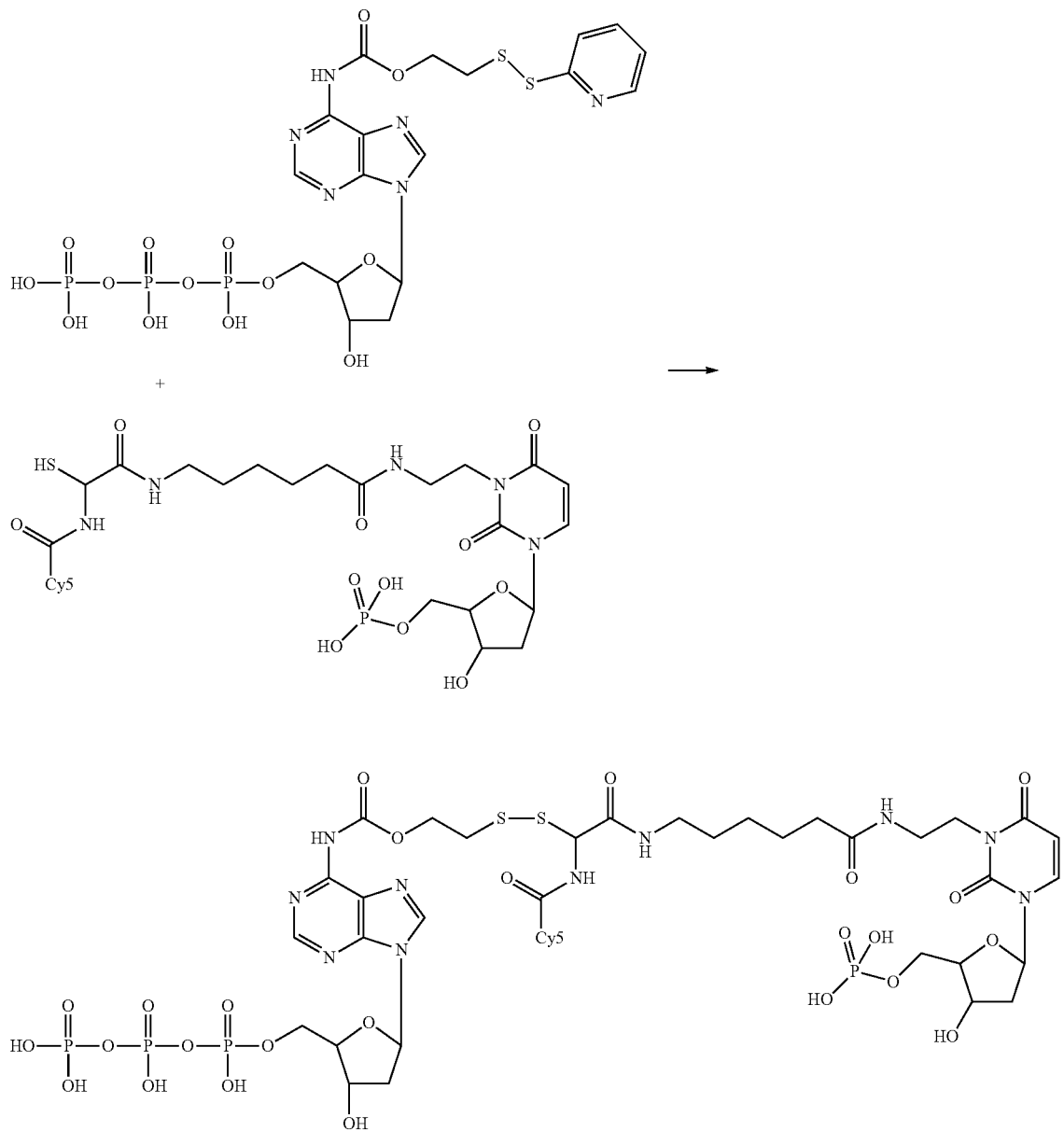
A second exemplary compound is shown below:
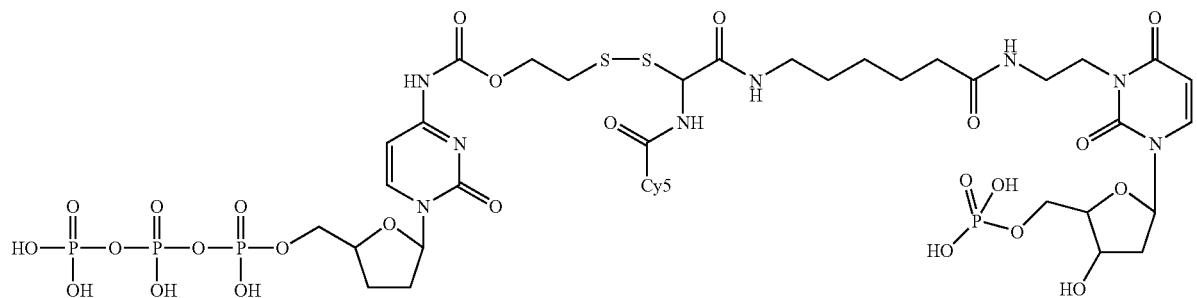

This compound is made via a disulfide cleavage step followed by a displacement reaction as follows:
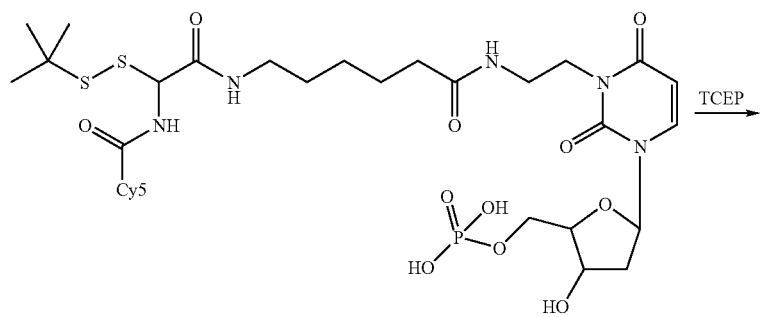
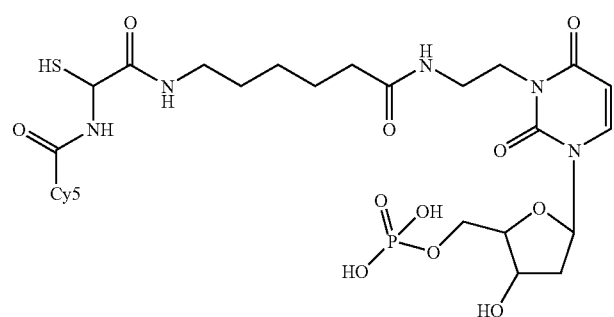
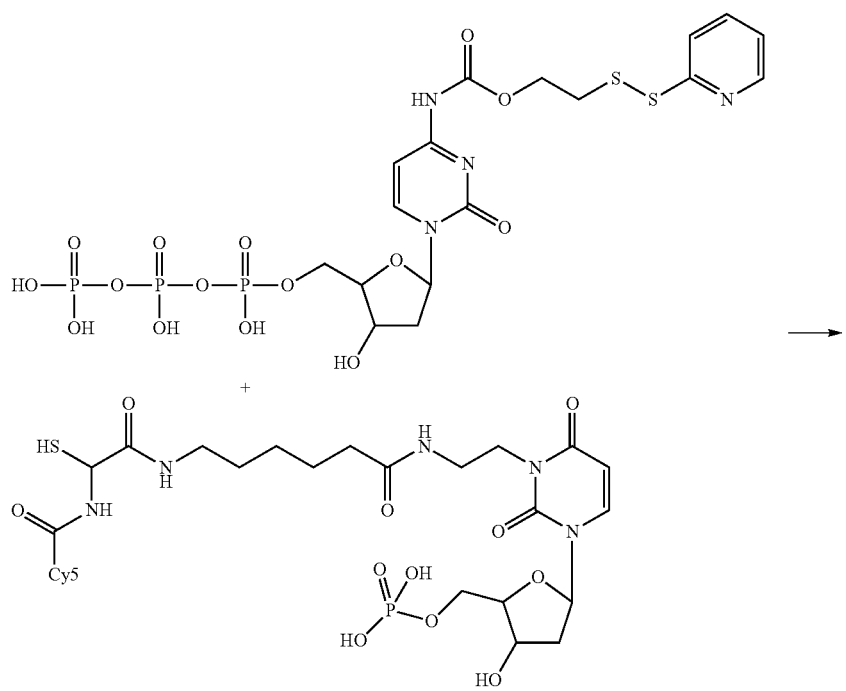

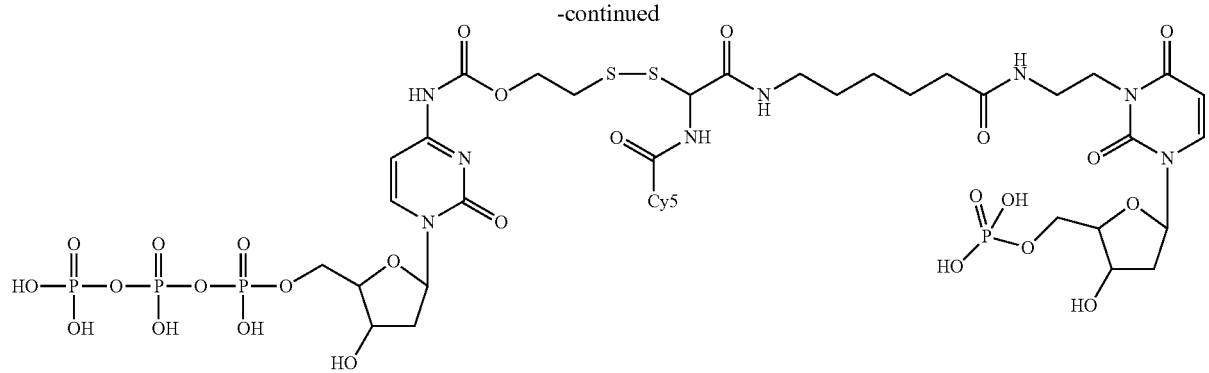
The synthesis of yet another exemplary analog of the invention is shown below:
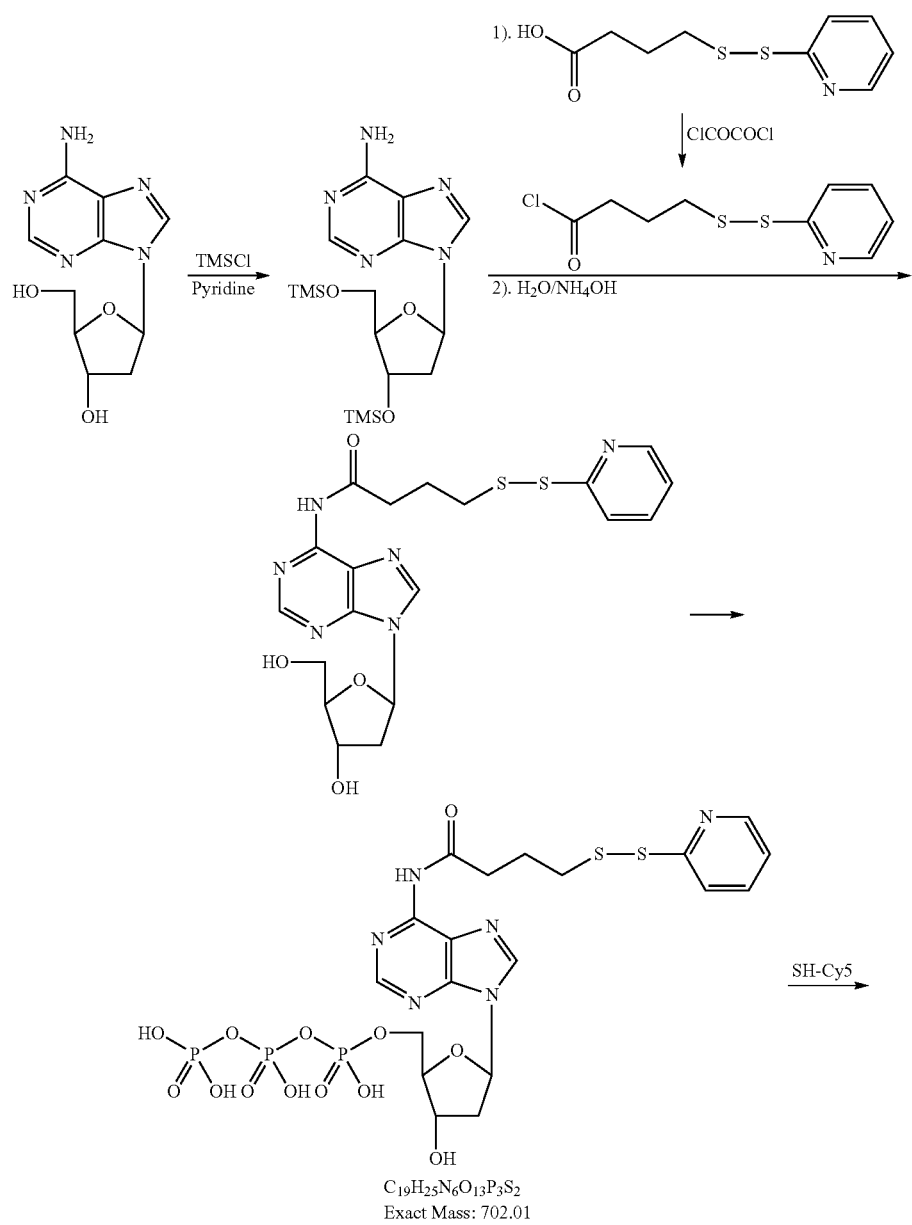

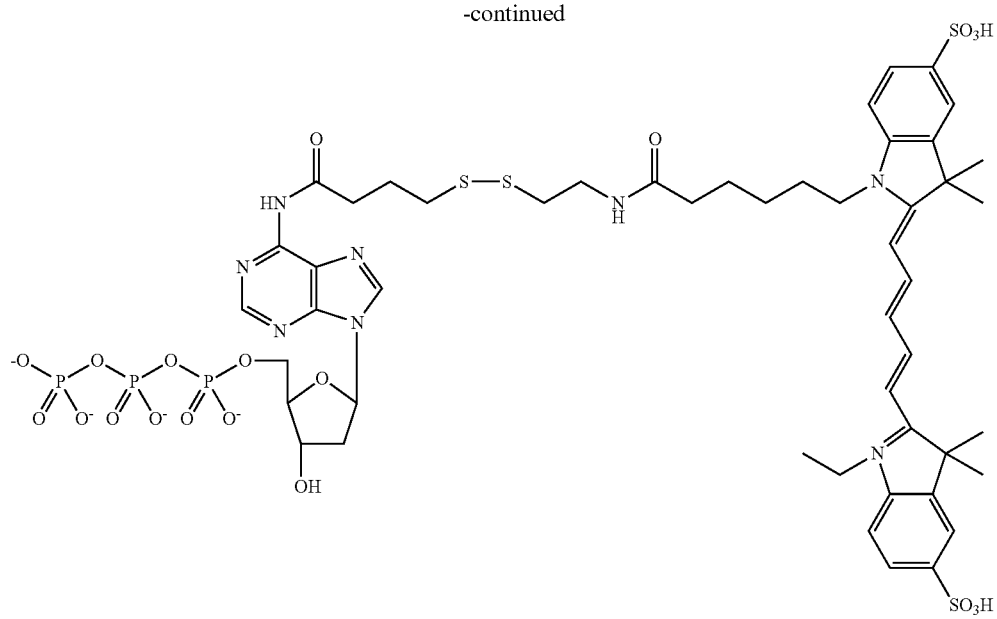
Another exemplary compound was made by the following synthesis route:
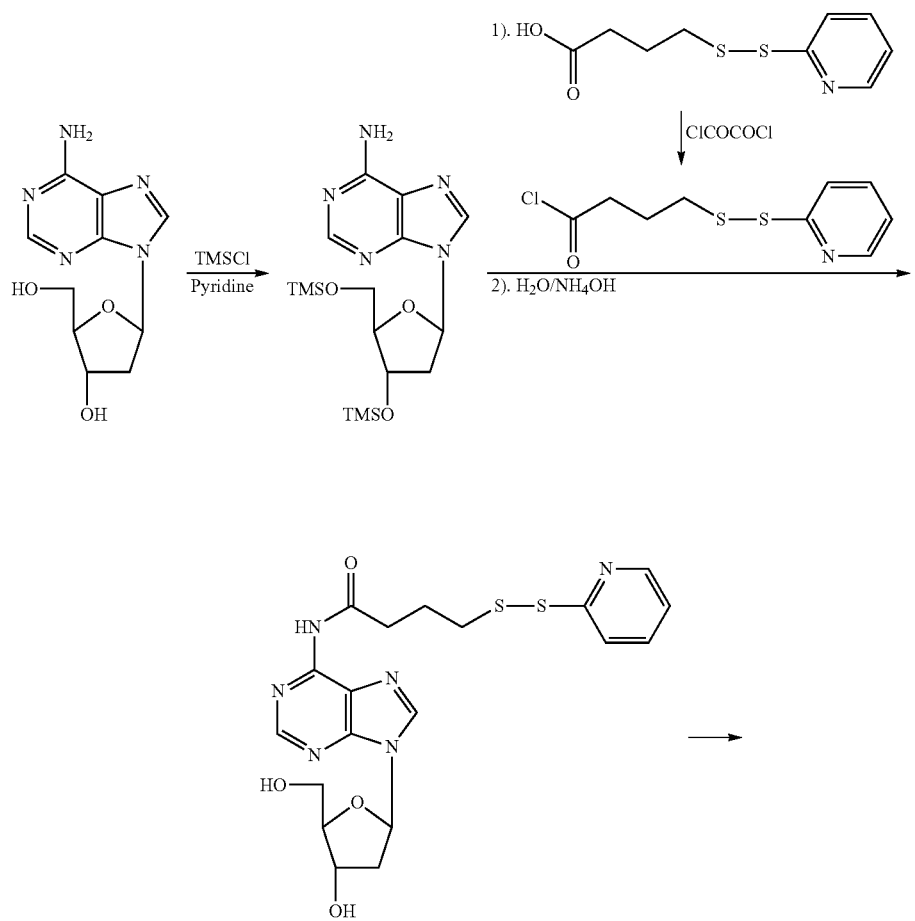

-continued
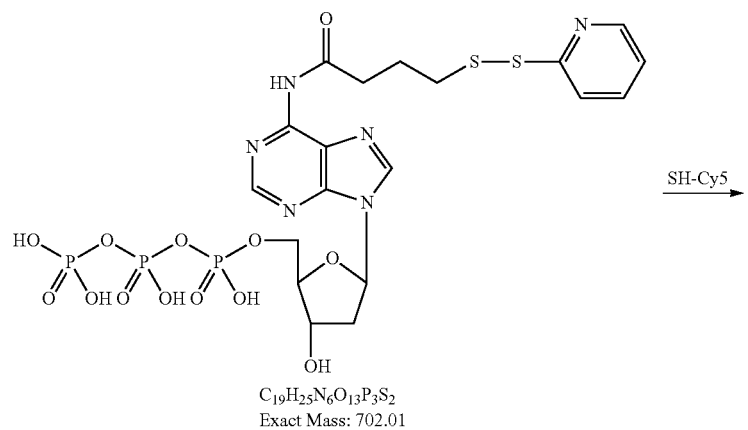
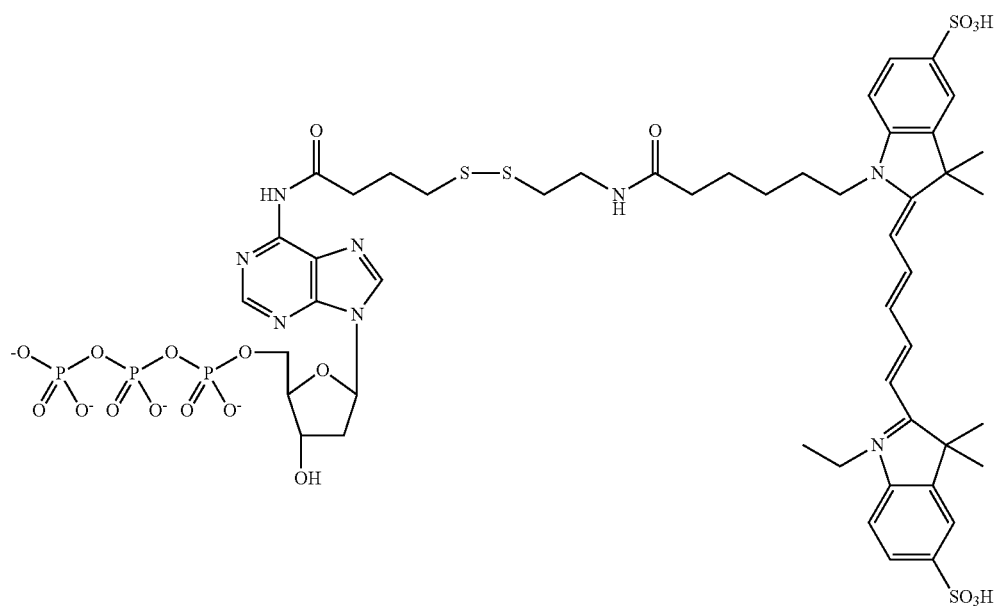
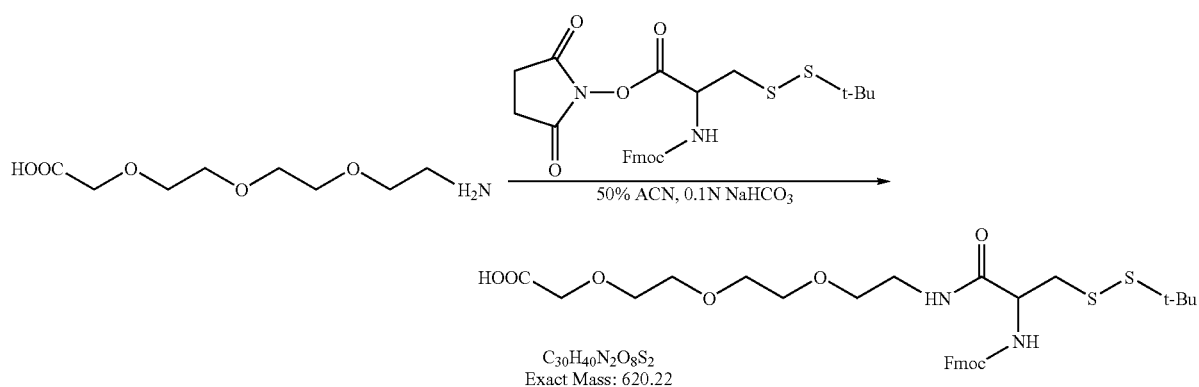

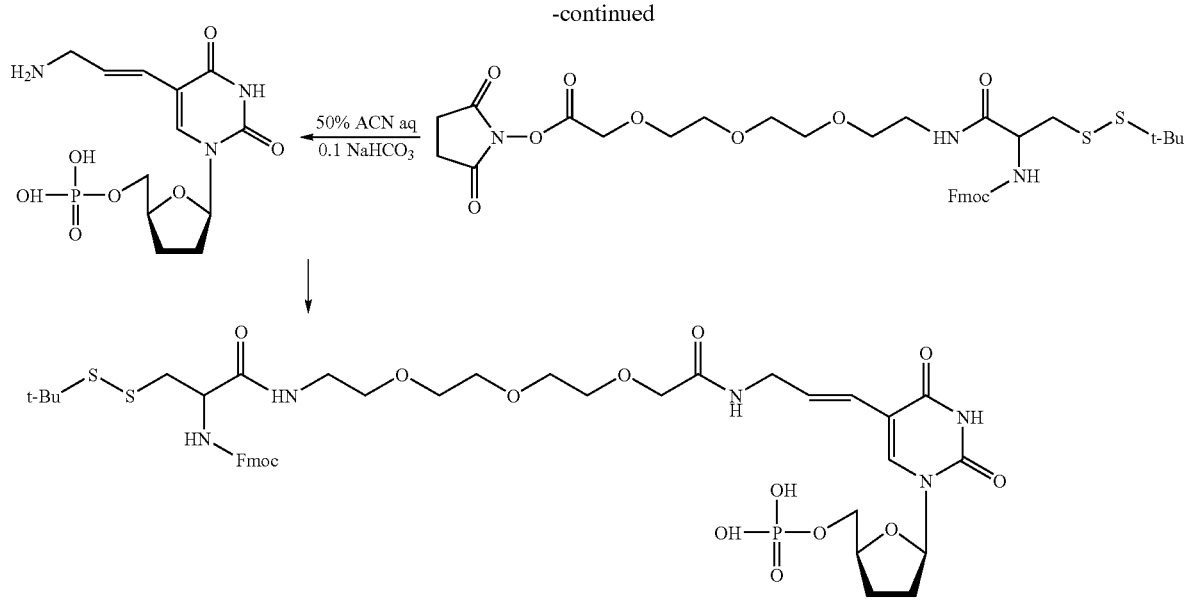

II. Template-Directed Sequencing-by-Synthesis

As discussed above, the invention provides improved methods for sequencing a nucleic acid containing a homopolymer region. The method comprises exposing a nucleic acid template/primer duplex to (i) a polymerase which catalyzes nucleotide addition to the primer, and (ii) a labeled nucleotide triphosphate analog comprising a first nucleotide or a first nucleotide analog covalently bonded through a tether to an inhibitor under conditions that permit the polymerase to add the labeled nucleotide triphosphate analog to the primer at a position complementary to the first base in the template while preventing another nucleotide or nucleotide analog from being added to the primer at a position complementary to the next downstream base. After the exposing step, the nucleotide triphosphate analog incorporated into the primer is detected. The inhibitor is removed to permit other nucleotides to be incorporated into the primer. It is contemplated that the label, for example, one of the optically detectable labels described herein, can be removed at the same time as the inhibitor. Any of the tethered nucleotide analogs described herein can be used in this type of sequencing protocol.

The following sections discuss general considerations for nucleic acid sequencing, for example, template considerations, polymerases useful in sequencing-by-synthesis, choice of surfaces, reaction conditions, signal detection and analysis.

Nucleic Acid Templates

Nucleic acid templates include deoxyribonucleic acid (DNA) and/or ribonucleic acid (RNA). Nucleic acid templates can be synthetic or derived from naturally occurring sources. In one embodiment, nucleic acid template molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. Biological samples for use in the present invention include viral particles or preparations. Nucleic acid template molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid template molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA.

Nucleic acid obtained from biological samples typically is fragmented to produce suitable fragments for analysis. In one embodiment, nucleic acid from a biological sample is fragmented by sonication. Nucleic acid template molecules can be obtained as described in U.S. Patent Application Publication Number US2002/0190663 A1, published Oct. 9, 2003. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Generally, individual nucleic acid template molecules can be from about 5 bases to about 20 kb. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In a preferred embodiment, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton® X series (Triton® X-100 t-Oct-$C_6H_4$—$(OCH_2$—$CH_2)_x$OH, x=9-10, Triton®X-100R, Triton® X-114 x=7-8), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulf-onate. It is contemplated also that urea may be added with or without another detergent or surfactant.

Lysis or homogenization solutions may further contain other agents, such as reducing agents. Examples of such reducing agents include dithiothreitol (DTT), β-mercaptoethanol, DTE, GSH, cysteine, cysteamine, tricarboxyethyl phosphine (TCEP), or salts of sulfurous acid.

Nucleic Acid Polymerases

Nucleic acid polymerases generally useful in the invention include DNA polymerases, RNA polymerases, reverse transcriptases, and mutant or altered forms of any of the foregoing. DNA polymerases and their properties are described in detail in, among other places, DNA Replication 2nd edition, Komberg and Baker, W. H. Freeman, New York, N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Ventm DNA polymerase, Cariello et al., 1991, Polynucleotides Res, 19: 4193, New England Biolabs), 9°Nm™ DNA polymerase (New England Biolabs), Stoffel fragment, ThermoSequenase® (Amersham Pharmacia Biotech UK), Therminator™ (New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacterioril, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO 0132887), *Pyrococcus* GB-D (PGB-D) DNA polymerase (also referred as Deep Ventm DNA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al., 1981, J. Biol. Chem. 256:3112), and archaeal DP1I/DP2 DNA polymerase II (Cann et al., 1998, Proc. Natl. Acad. Sci. USA 95:14250).

Both mesophilic polymerases and thermophilic polymerases are contemplated. Thermophilic DNA polymerases include, but are not limited to, ThermoSequenase®, 9°Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. A highly-preferred form of any polymerase is a 3' exonuclease-deficient mutant.

Reverse transcriptases useful in the invention include, but are not limited to, reverse transcriptases from HIV, HTLV-1, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al., CRC Crit. Rev Biochem. 3:289-347 (1975)).

Surfaces

In a preferred embodiment, nucleic acid template molecules are attached to a substrate (also referred to herein as a surface) and subjected to analysis by single molecule sequencing as described herein. Nucleic acid template molecules are attached to the surface such that the template/primer duplexes are individually optically resolvable. Substrates for use in the invention can be two- or three-dimensional and can comprise a planar surface (e.g., a glass slide) or can be shaped. A substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a nucleic acid. Substrates can include planar arrays or matrices capable of having regions that include populations of template nucleic acids or primers. Examples include nucleoside-derivatized CPG and polystyrene slides; derivatized magnetic slides; polystyrene grafted with polyethylene glycol, and the like.

Substrates are preferably coated to allow optimum optical processing and nucleic acid attachment. Substrates for use in the invention can also be treated to reduce background. Exemplary coatings include epoxides, and derivatized epoxides (e.g., with a binding molecule, such as an oligonucleotide or streptavidin).

Various methods can be used to anchor or immobilize the nucleic acid molecule to the surface of the substrate. The immobilization can be achieved through direct or indirect bonding to the surface. The bonding can be by covalent linkage. See, Joos et al., Analytical Biochemistry 247:96-101, 1997; Oroskar et al., *Clin. Chem.* 42:1547-1555, 1996; and Khandjian, *Mol. Bio. Rep.* 11:107-115, 1986. A preferred attachment is direct amine bonding of a terminal nucleotide of the template or the 5' end of the primer to an epoxide integrated on the surface. The bonding also can be through non-covalent linkage. For example, biotin-streptavidin (Taylor et al., *J. Phys. D. Appl. Phys.* 24:1443, 1991) and digoxigenin with anti-digoxigenin (Smith et al., *Science* 253:1122, 1992) are common tools for anchoring nucleic acids to surfaces and parallels. Alternatively, the attachment can be achieved by anchoring a hydrophobic chain into a lipid monolayer or bilayer. Other methods for known in the art for attaching nucleic acid molecules to substrates also can be used.

Detection

Any detection method can be used that is suitable for the type of label employed. Thus, exemplary detection methods include radioactive detection, optical absorbance detection, e.g., UV-visible absorbance detection, optical emission detection, e.g., fluorescence or chemiluminescence. For example, extended primers can be detected on a substrate by scanning all or portions of each substrate simultaneously or serially, depending on the scanning method used. For fluorescence labeling, selected regions on a substrate may be serially scanned one-by-one or row-by-row using a fluorescence microscope apparatus, such as described in Fodor (U.S. Pat. No. 5,445,934) and Mathies et al. (U.S. Pat. No. 5,091, 652). Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993), such as described in Yershov et al., Proc. Natl. Acad. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc. Such detection methods are particularly useful to achieve simultaneous scanning of multiple attached template nucleic acids.

A number of approaches can be used to detect incorporation of fluorescently-labeled nucleotides into a single nucleic acid molecule. Optical setups include near-field scanning microscopy, far-field confocal microscopy, wide-field epi-illumination, light scattering, dark field microscopy, photoconversion, single and/or multiphoton excitation, spectral wavelength discrimination, fluorophor identification, evanescent wave illumination, and total internal reflection fluorescence (TIRF) microscopy. In general, certain methods involve detection of laser-activated fluorescence using a microscope equipped with a camera. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

Some embodiments of the present invention use TIRF microscopy for imaging. TIRF microscopy uses totally internally reflected excitation light and is well known in the art. See, e.g., the World Wide Web at nikon-instrumentsjp/eng/page/products/tirf.aspx. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. The optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths.

The evanescent field also can image fluorescently-labeled nucleotides upon their incorporation into the attached template/primer complex in the presence of a polymerase. Total internal reflectance fluorescence microscopy is then used to visualize the attached template/primer duplex and/or the incorporated nucleotides with single molecule resolution.

Analysis

Alignment and/or compilation of sequence results obtained from the image stacks produced as generally described above utilizes look-up tables that take into account possible sequences changes (due, e.g., to errors, mutations, etc.). Essentially, sequencing results obtained as described herein are compared to a look-up type table that contains all possible reference sequences plus 1 or 2 base errors.

EXAMPLES

The invention is further illustrated by the following non-limiting examples.

Example 1

Figure 2:
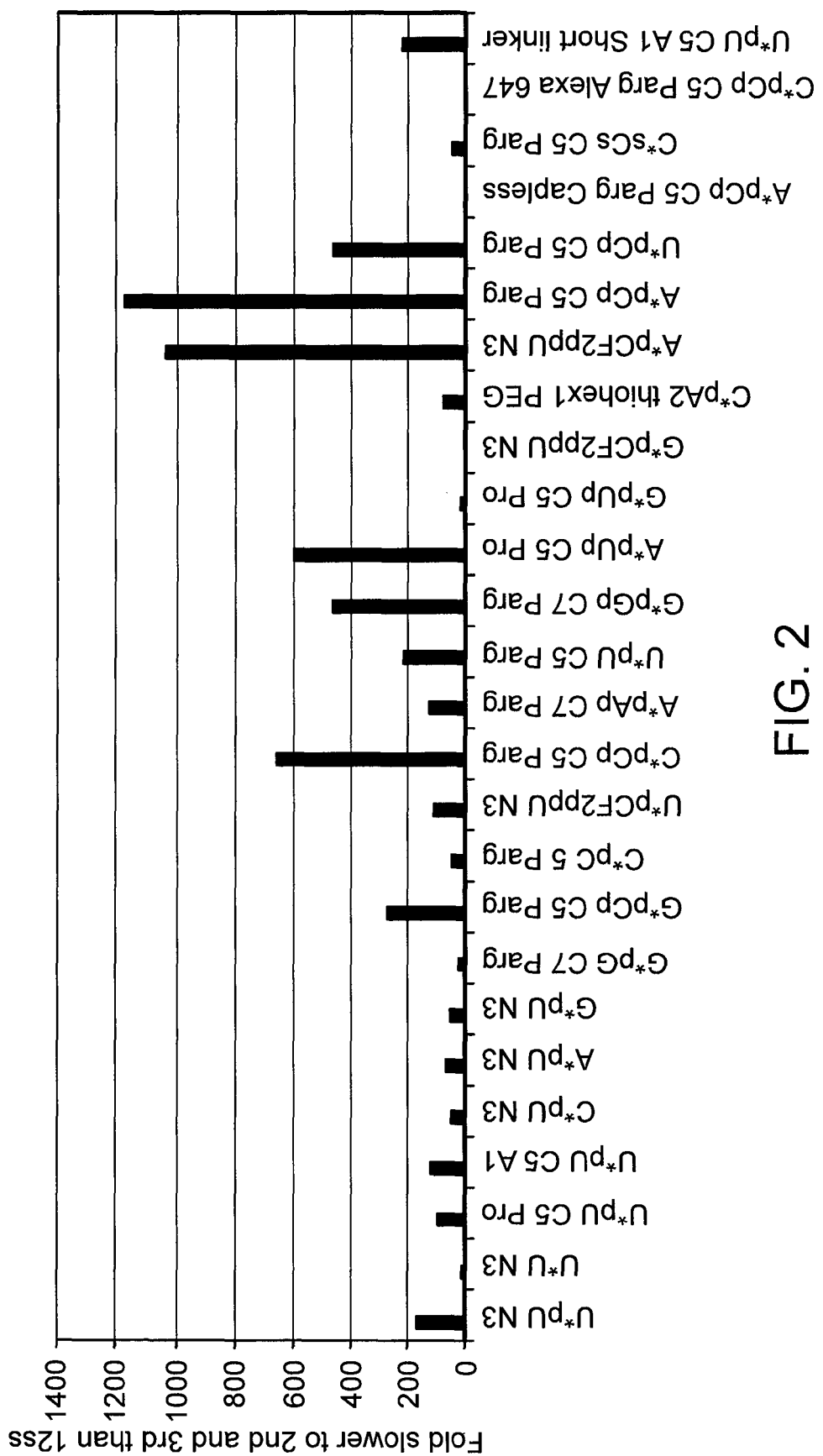
FIG. 2 depicts the kinetic properties of nucleotide analogs of the invention, compared to a control dye-labeled nucleotide analog that is not of the tethered class of analogs (Cy5-12SS-dNTP), of read through to a second or subsequent base after adding to first of a series of repeating bases in a template, e.g. a value of 100 is 100 times slower at adding $2^{nd}$ and $3^{rd}$ bases in a homopolymer relative to the control.

26 different tethered nucleotide analogs of the invention were tested for their ability to be incorporated during a template-dependent sequencing reaction and to inhibit next base (or N+1) incorporation when sequencing through a homopolymer region. FIG. 2 illustrates the kinetic performance of various tethered nucleotide analogs with respect to their propensity to not read through to second and subsequent bases after adding to the first of a series of repeating bases in a template. As depicted in FIG. 2, various novel tethered analogs identified above and disclosed herein (see Table 1), exhibit a decrease in homopolymer read-through, e.g. are slower at adding a second base over a first base, as compared with the conventional fluorophore labeled analog shown below. The tethered analog identified as C*pCpC5 Parg exhibits about 630 fold improvement in ability to avoid double incorporation in a single base addition step as compared to the control; the tethered analog identified as U*pU C5 Parg exhibits about a 200 fold improvement; and the tethered analog identified as A*pCpC5 Parg exhibits an improvement of more than three orders of magnitude.

The control analog has the following structure:

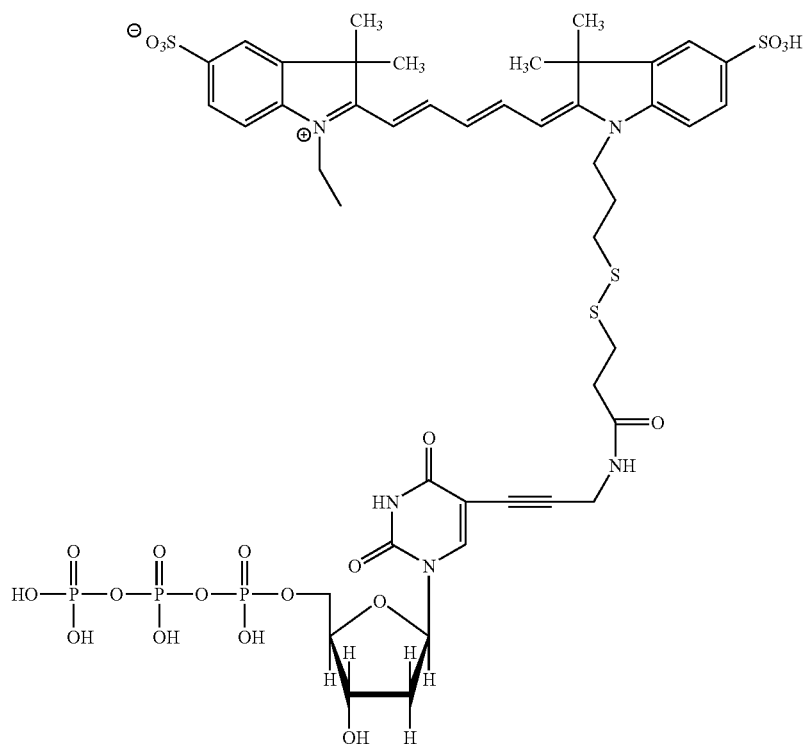

Example 2

Figure 3:
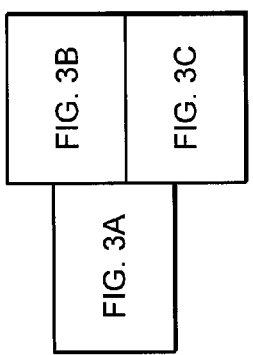
FIG. 3 depicts capillary electrophoresis data reflecting the ability of analog G*pCpC5 Parg (Compound XVI) to be incorporated once for each of 5 cycles of polymerization on a 5G-containing template as compared to the control compound, Cy5-12 SS-dCTP.
Figure 3A:
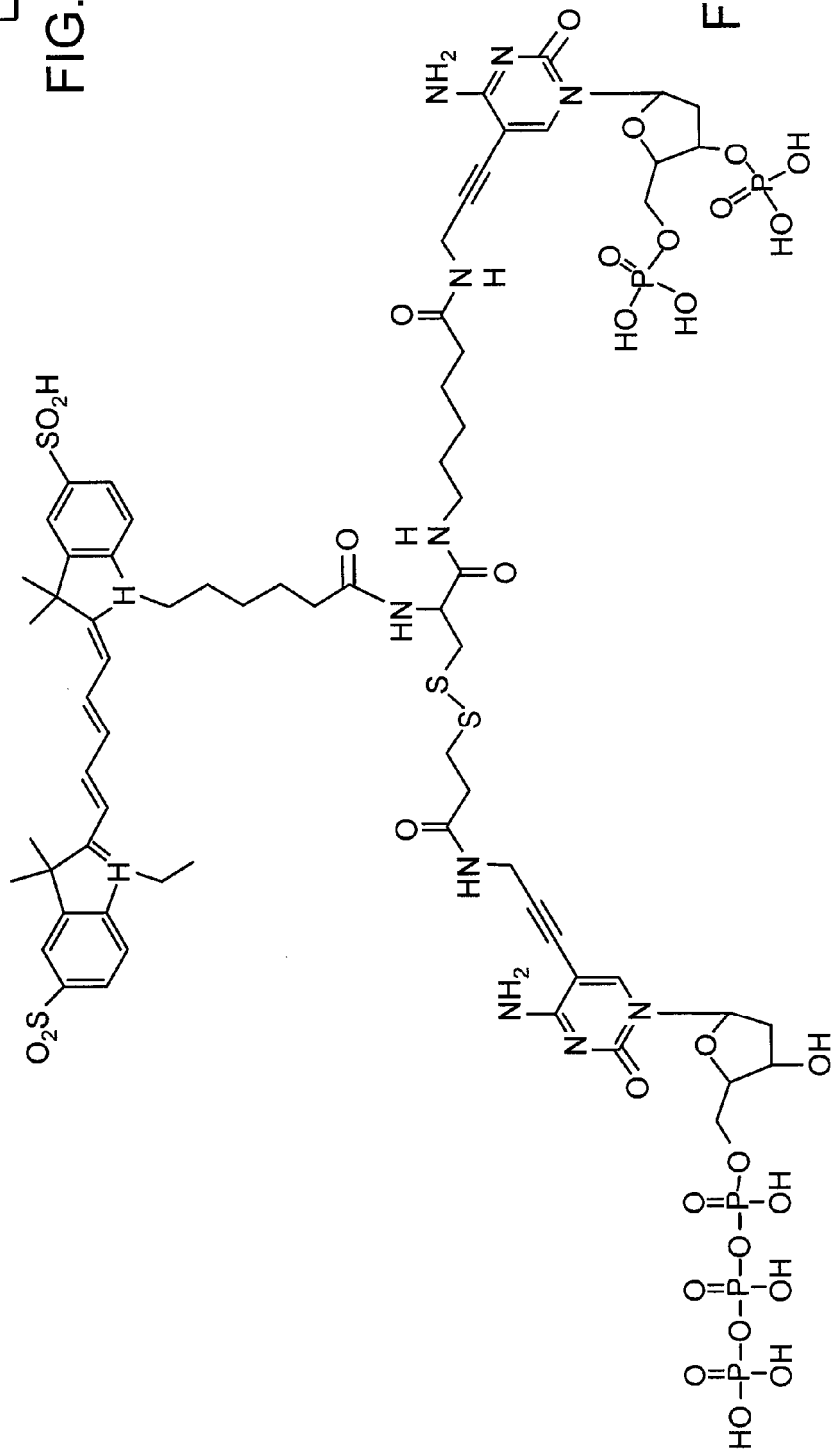
Figure 3B:
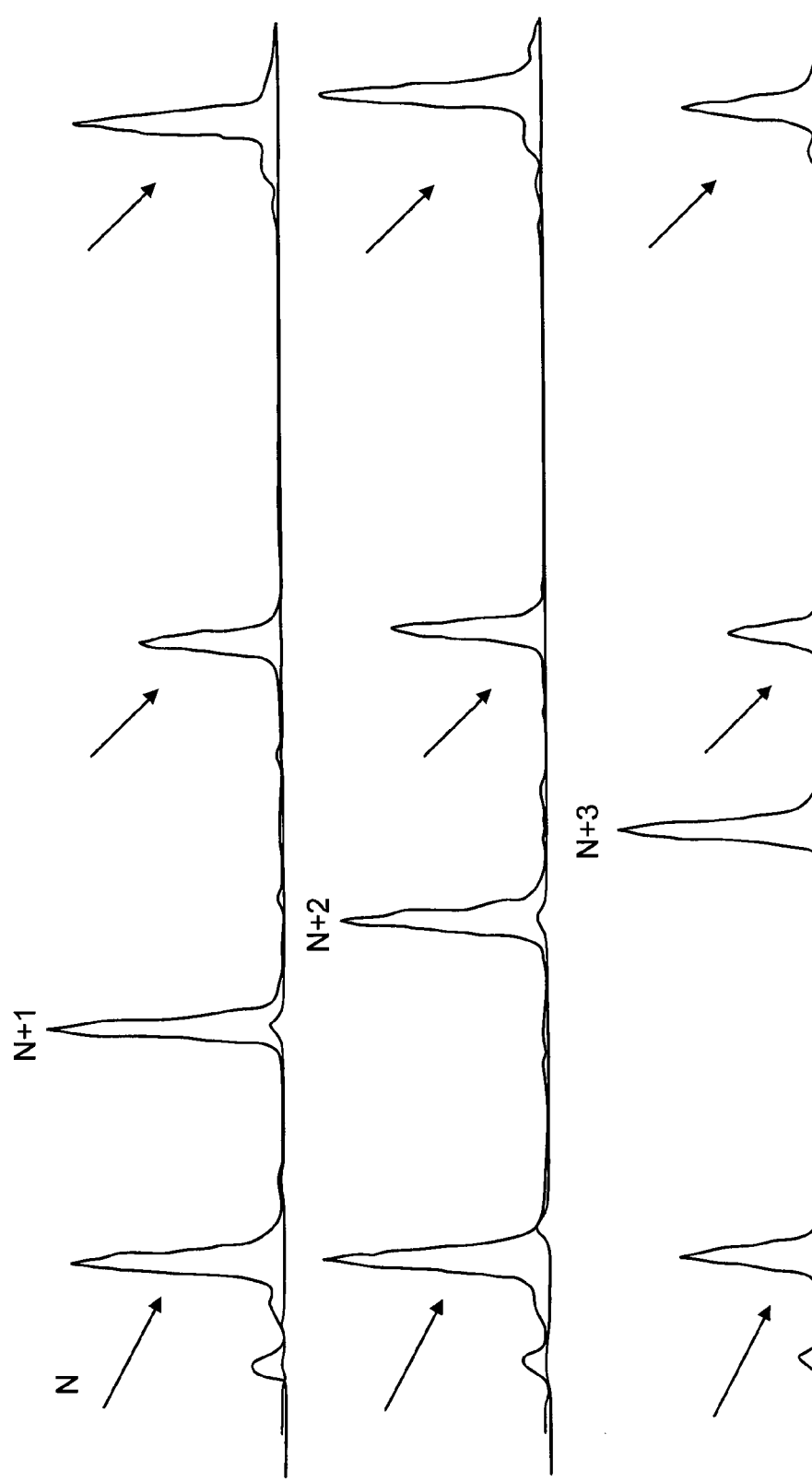
Figure 3C:
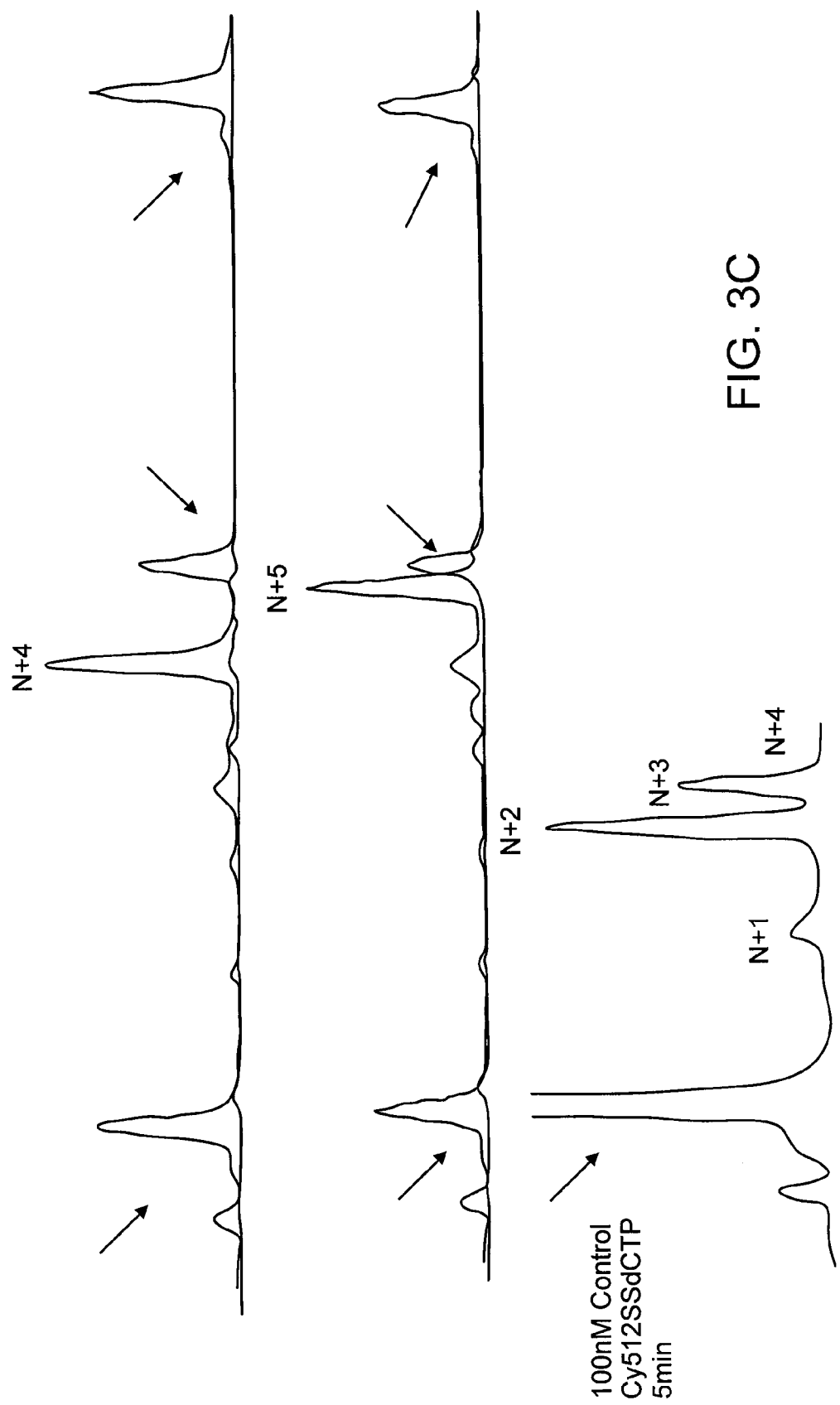

A tethered nucleotide analog of the invention was tested for the ability to be incorporated once for each cycle of polymerization during a template-dependent sequencing reaction. The capillary electrophoresis data in shown in FIG. 3 shows the ability of analog C*pCpC5 Parg to be incorporated once for each of 5 cycles of polymerization on a 5G-containing template as compared to the performance of 12SS. Each test cycle exposed 100 nM analog to the templates for five minutes. The signals identified with arrows are molecular weight standards. FIG. 3 depicts distinct, major peaks representing template plus 1, 2, 3, 4, and 5 added Cytosine analog bases, with only small amounts of lower addition products contaminating the +4 and +5 products. In contrast, a single cycle with the control analog shown above produced a mixture of +1, +2, +3, and +4 products, obscuring the length of the homopolymeric portion of the template and the true sequence.

Example 3

Figure 4:
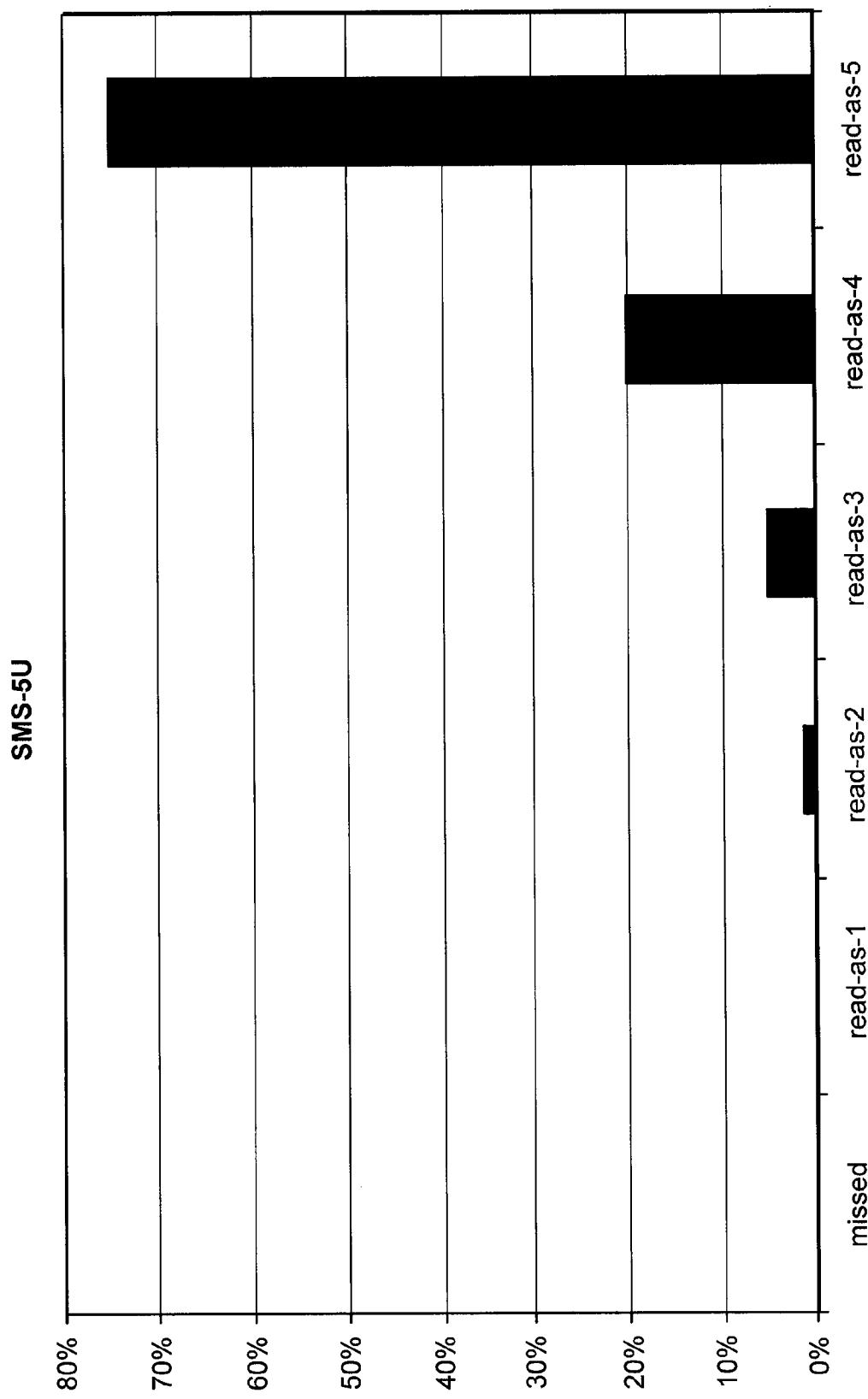
FIG. 4 shows results of a sequencing experiment in which an analog of the invention allowed substantially single base incorporation.

The performance of a nucleotide analog was conducted on a field of single molecule templates comprising 5 consecutive A's. FIG. 4 shows the results of nucleotide analog U*pU C5 allyl (See FIG. 14, XXVIII) on such a template. After five cycles of incorporation of the uracil analog, essentially none of the templates were read as having no A's or one A, approximately 5% of the templates were read as having 3 A's, 20% as having 4 A's, and 75% as having 5 A's.

Example 4

This example shows a novel synthesis for one of the exemplary compositions of the invention.

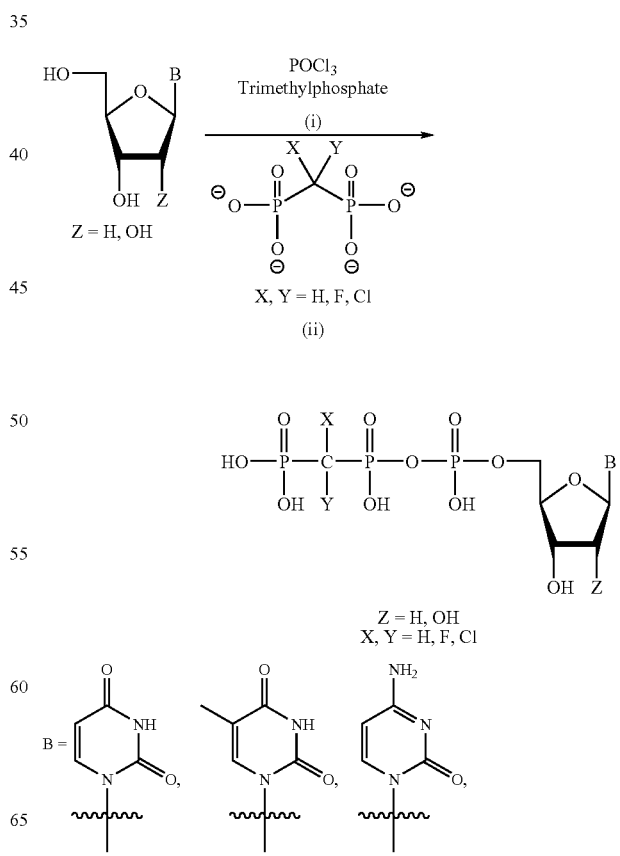

-continued

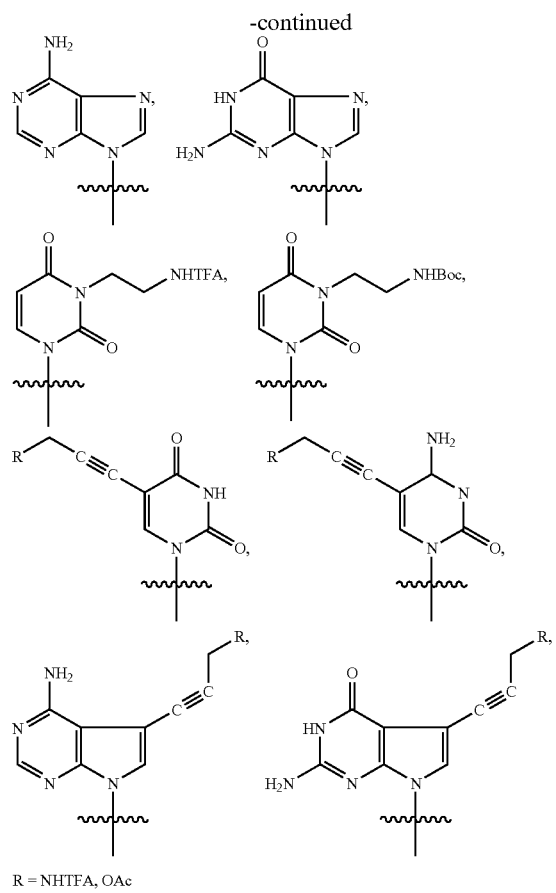

R = NHTFA, OAc

Synthesis of Tris(tetra-n-butylammonium)difluoromethylenediphosphonate

INCORPORATION BY REFERENCE

All publications, patents, and patent applications cited herein are hereby expressly incorporated by reference in their entirety and for all purposes to the same extent as if each was so individually denoted.

EQUIVALENTS

While specific embodiments of the subject invention have been discussed, the above specification is illustrative and not restrictive. Many variations of the invention will become apparent to those skilled in the art upon review of this specification. Contemplated equivalents of the nucleotide analogs disclosed here include compounds which otherwise correspond thereto, and which have the same general properties thereof, wherein one or more simple variations of substituents or components are made which do not adversely affect the characteristics of the nucleotide analogs of interest. In general, the components of the nucleotide analogs disclosed herein may be prepared by the methods illustrated in the general reaction schema as described herein or by modifications thereof, using readily available starting materials, reagents, and conventional synthesis procedures. The full scope of the invention should be determined by reference to the claims, along with their full scope of equivalents, and the specification, along with such variations.

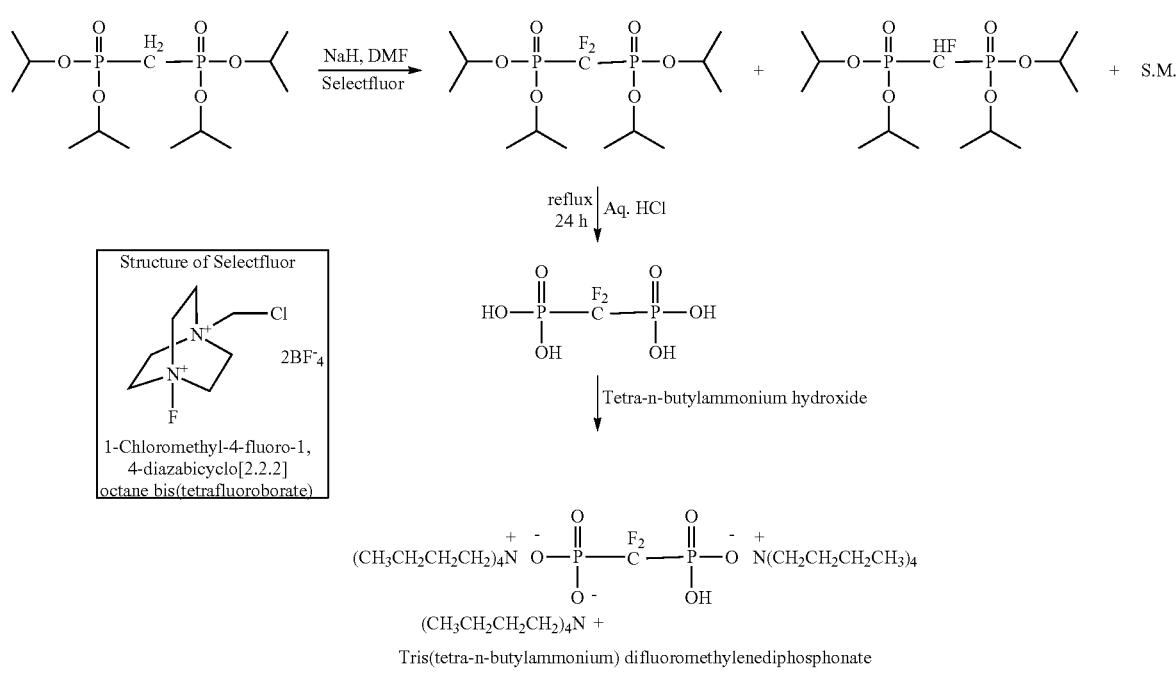

What is claimed is:

1. A nucleoside triphosphate analog comprising a chemical structure within the following formula:

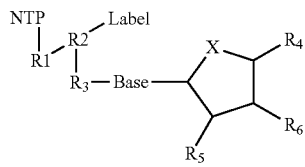

I wherein:
NTP is a nucleoside triphosphate or analog thereof capable of incorporating onto the 3' end of a polynucleotide strand hybridized to a template presenting the complement of said NTP;
R1 is an alkyl, alkenyl, alkynyl amide, or alkyl amide;
R2 is a cleavable bond or group;
R3 is an alkyl, alkenyl, alkyl amide, alkynyl amide, aryl, ether, or ester;
R4 is selected from the group consisting of: OH, phosphoryl, sulfate, $NH_2$, SH, an amino acid, a peptide comprising 1 to 12 amino acids,

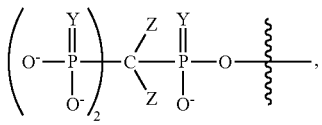

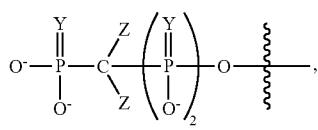

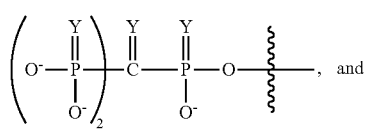
and

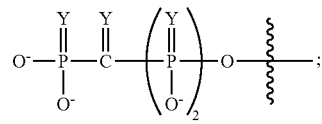

Y, at each occurrence, independently is O or S;
Z represents H or a halogen;
R5 and R6 are independently selected from the group consisting of: H, OH, phosphoryl, $P_2O_7^{-3}$, sulfate, $NH_2$, SH, or a halogen; and
X is selected from the group consisting of: O, S, or $CH_2$.

2. The analog of claim 1 wherein said cleavable bond is selected from: a disulfide bond, an ester, an azo bond, and an amido bond.

3. The analog of claim 1 wherein said Base and the nitrogenous base of said NTP are different bases.

4. The analog of claim 1, wherein said Base and the nitrogenous base of said NTP are each independently selected from the group consisting of: cytosine, uracil, thymine, adenine, guanine, and analogs thereof.

5. The analog of claim 1 wherein R6 is selected from the group consisting of $PO_4^{-2}$ and $SO_4^-$.

6. The analog of claim 1 wherein R4 is selected from the group consisting of $PO_4^{-2}$, $SO_4^-$, $P_2O_7^{-3}$, $PO_3S^{-2}$, and $P_2O_6S_2^{3-}$.

7. The analog of claim 1 wherein Z is fluorine.

8. The analog of claim 1 wherein R5 is H or OH, and R4 and R6 are each independently $PO_4^{-2}$ or $SO_4^-$.

9. The analog of claim 1 wherein R3 comprises ethylene glycol or propylene glycol.

10. The analog of claim 1 wherein R3 comprises a diethylene glycol or dipropylene glycol.

11. The analog of claim 10 wherein R3 is polyethylene glycol.

12. The analog of claim 1 wherein R3 comprises at least one of: ester, amide, ether, divalent alkyl, divalent alkenyl, or divalent alkynyl.

13. The analog of claim 1 wherein said Base is deaza adenine or deaza guanine and R3 is linked to the C-7 or C-8 position of said deaza adenine or deaza guanine.

14. The analog of claim 1 wherein said base is thymine, cytosine, or uracil and R3 is linked to the N-3 or C-5 positions of said thymine, cytosine, or uracil.

15. The analog of claim 1, wherein said Label is an optically-detectable label.

16. The analog of claim 15, wherein said optically-detectable label is a fluorophore.

17. The analog of claim 16, wherein said fluorophore is selected from the group consisting of: Cy5 and Cy3.

18. A molecule having a structure selected from the group consisting of:
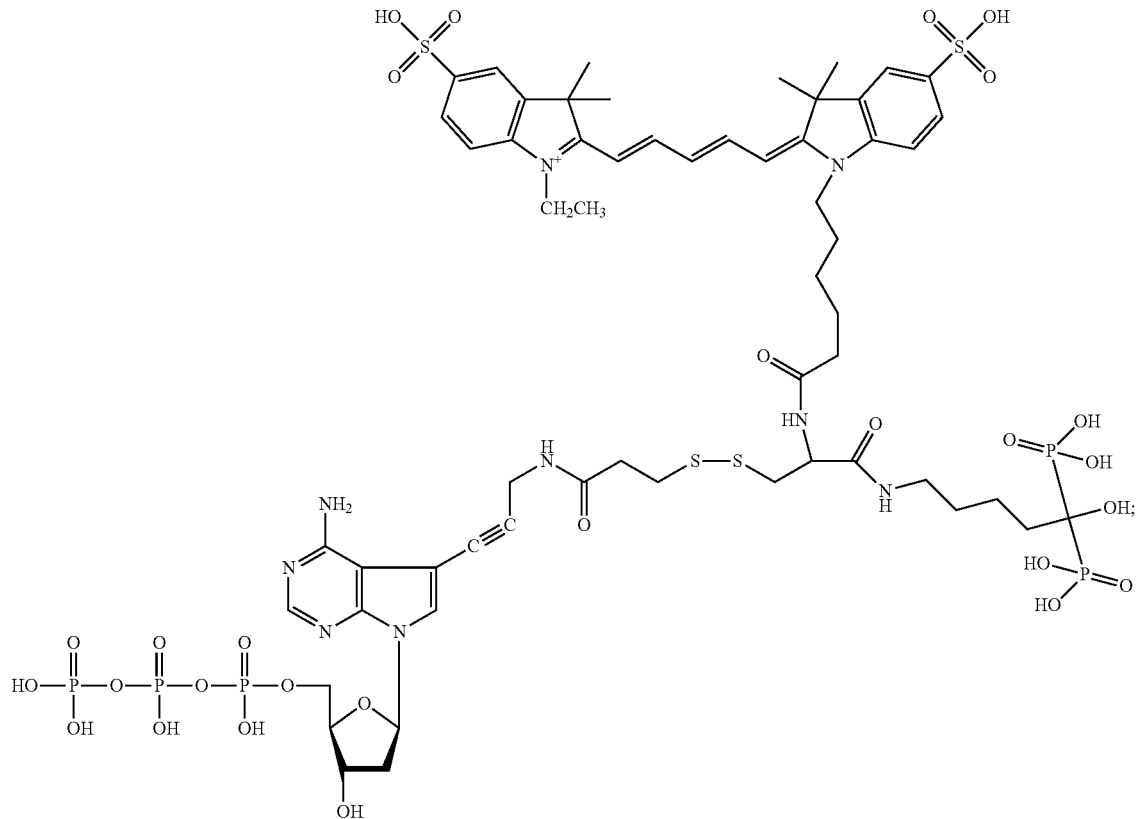
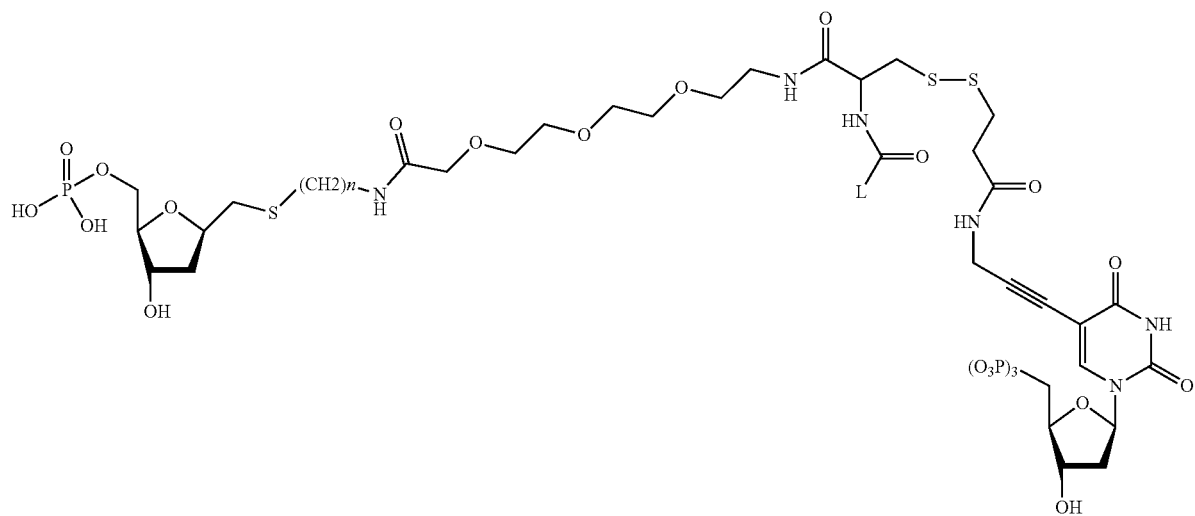

Wherein L is a detectable label and n is from 1 to 10;

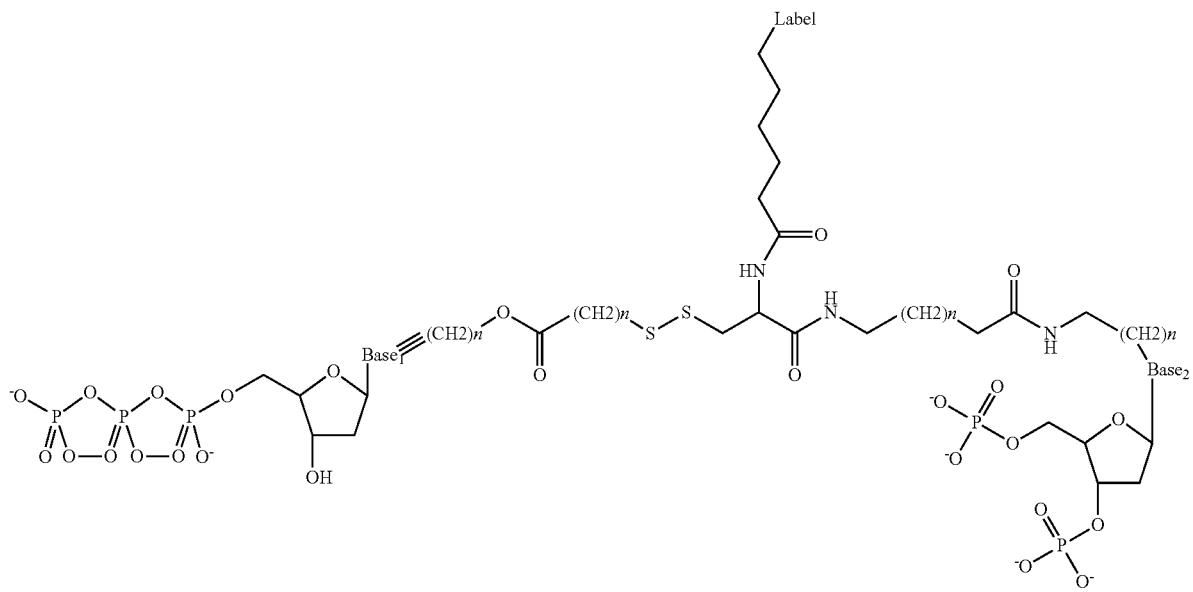

Wherein L is a detectable label, Base₁ and Base₂ are independently selected from adenine, thymine, guanine, cytosine, uracil and derivatives of the foregoing, and n is from 1 to 10;

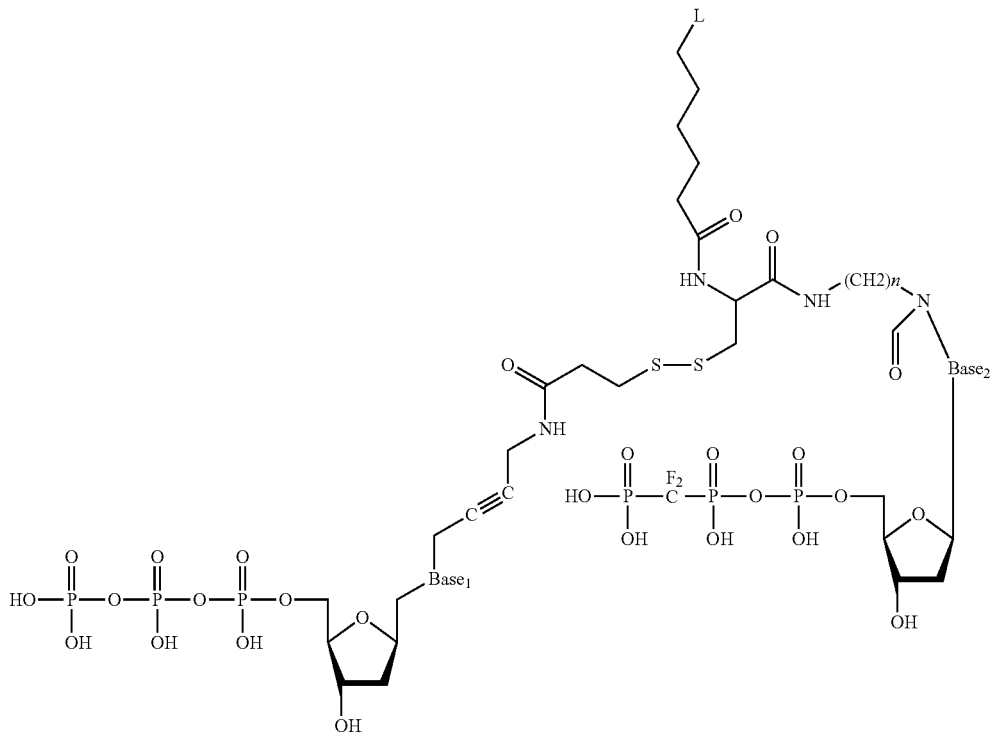

Wherein L is a detectable label, Base₁ and Base₂ are independently selected from adenine, thymine, guanine, cytosine, uracil and derivatives of the foregoing, and n is from 1 to 10.

19. A molecule having the following structure:

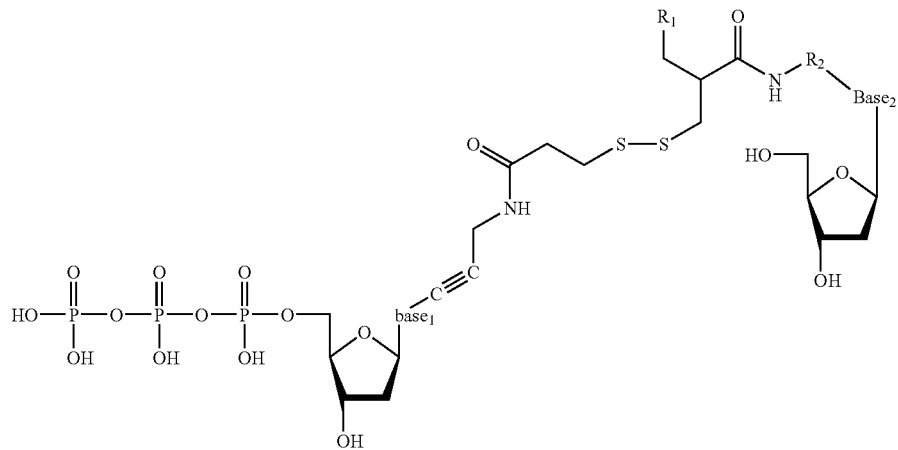

Wherein, $R_1$ is a dectable label, $R_2$ is an alkyl, alkenyl, amide, or ether, and $Base_1$ and $Base_2$ are independently selected from adenine, thymine, guanine, cytosine, uracil and derivatives of the foregoing.

20. A molecule having the following structure:

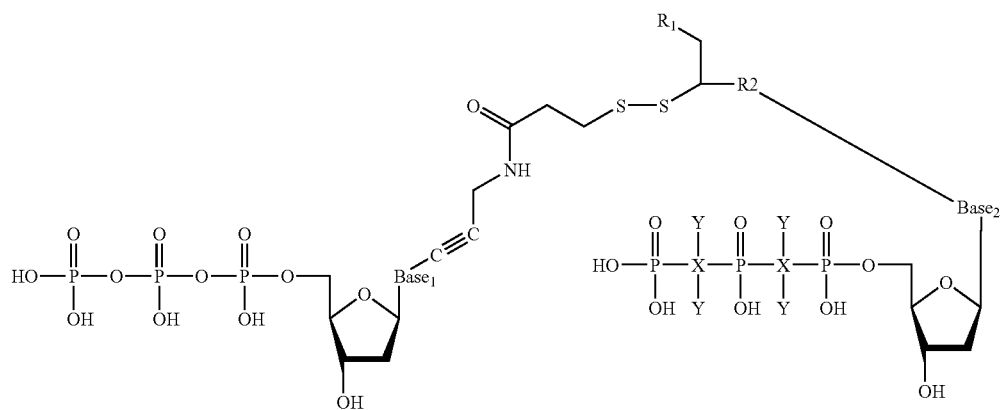

Wherein $Base_1$ and $Base_2$ are independently is selected from adenine, thymine, guanine, cytosine, uracil and derivatives of the foregoing; R1 is a detectable label; and R2 is an alkyl, alkenyl, amide, or ether.

21. A molecule having the following structure:

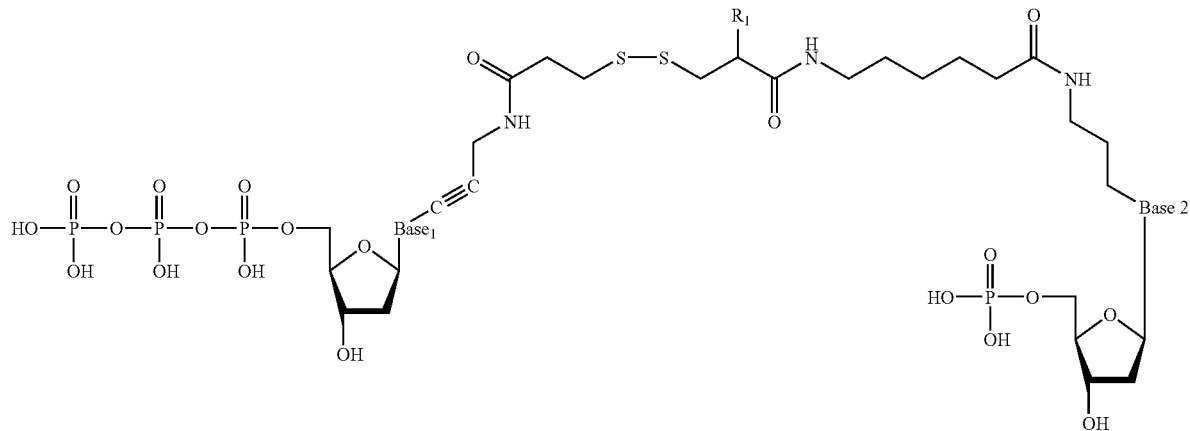

Wherein Base$_1$ and Base$_2$ are independently is selected from adenine, thymine, guanine, cytosine, uracil and derivatives of the foregoing; and R1 is a detectable label.

22. A molecule having the following structure:

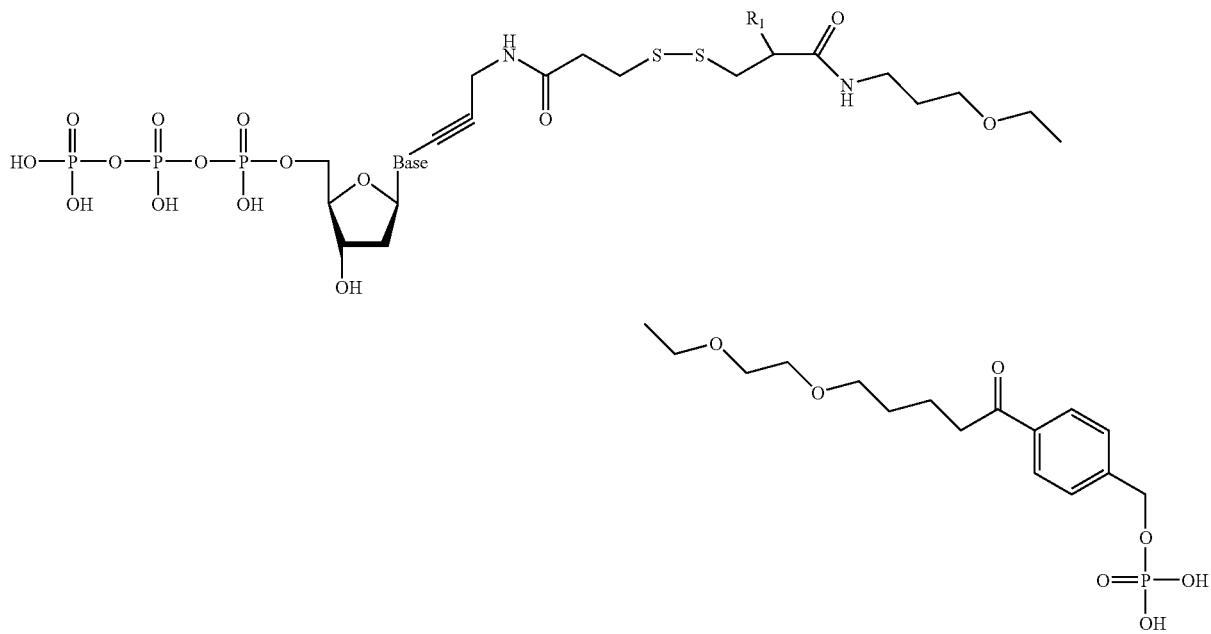

Wherein Base is selected from adenine, thymine, guanine, cytosine, uracil and derivatives of the foregoing and R1 is a detectable label.

23. A molecule having the following structure:

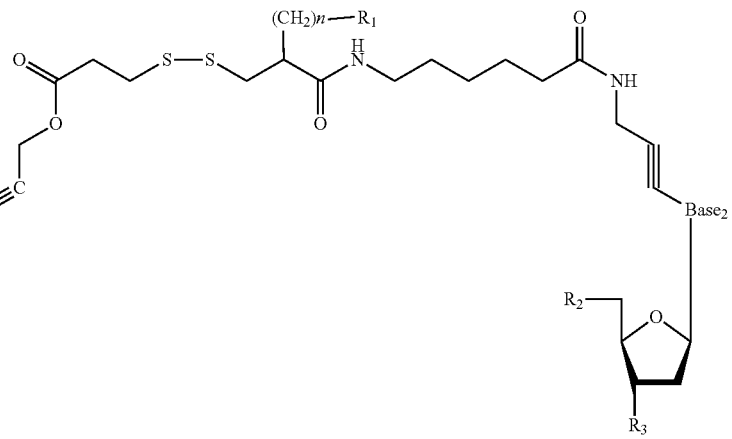
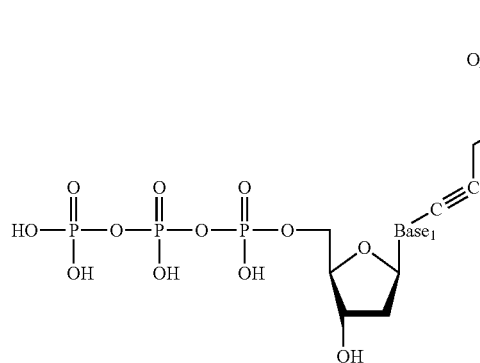

Wherein Base₁ and Base₂ are independently is selected from adenine, thymine, guanine, cytosine, uracil and derivatives of any of the foregoing; R1 is a detectable label, R2 is selected from OH and $PO_3^-$, R3 is selected from a monophosphate, a diphosphate, a triphosphate, and OH, and n is from about 1 to about 10 atoms in length.

24. A method of sequencing a nucleic acid , the method comprising the steps of:
 a) contacting a field of template molecules and primers annealed thereto with an analog of any of claims 1-23 in the presence of a polymerase to extend said primers by covalent attachment of one analog in a template-dependent manner;
 b) washing the field to remove non-covalently attached analog;
 c) detecting signal from label bound to said attached analog;
 d) cleaving said cleavable bond thereby separating said label from said NTP; and
 e) repeating steps a) through d).

* * * * *